(12) United States Patent
Rahilly et al.

(10) Patent No.: US 12,079,772 B2
(45) Date of Patent: Sep. 3, 2024

(54) INTERACTIVE INVENTORY STORAGE DEVICE, SYSTEM, AND METHOD

(71) Applicant: CareFusion 303, Inc., San Diego, CA (US)

(72) Inventors: Michael K. Rahilly, Encinitas, CA (US); Brendan John Burgess, Poway, CA (US); Ramkumar Subramanian, San Diego, CA (US); Mustafa Yusufi, Escondido, CA (US); Monica Wyly, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/211,188

(22) Filed: Jun. 16, 2023

(65) Prior Publication Data

US 2023/0410045 A1 Dec. 21, 2023

Related U.S. Application Data

(60) Continuation of application No. 17/343,636, filed on Jun. 9, 2021, now Pat. No. 11,681,985, which is a
(Continued)

(51) Int. Cl.
*G06Q 10/0875* (2023.01)
*G06K 19/07* (2006.01)
(Continued)

(52) U.S. Cl.
CPC ..... *G06Q 10/0875* (2013.01); *G06K 19/0728* (2013.01); *G06N 3/08* (2013.01);
(Continued)

(58) Field of Classification Search
CPC ............... G06Q 10/0875; G06Q 20/12; G06K 19/0728; G06N 3/08; G07C 9/00896;
(Continued)

(56) References Cited

U.S. PATENT DOCUMENTS

| 7,479,877 B2 * | 1/2009 | Mortenson | G06Q 10/047 |
| | | | 340/545.6 |
| 7,564,350 B2 * | 7/2009 | Boman | G06Q 10/047 |
| | | | 340/545.6 |

(Continued)

FOREIGN PATENT DOCUMENTS

CN 102473254 A 5/2012

OTHER PUBLICATIONS

Chinese Office Action for Application No. 202080062117.6, dated Nov. 17, 2023, 6 pages including machine translation.
(Continued)

*Primary Examiner* — Garcia Ade
(74) *Attorney, Agent, or Firm* — Morgan, Lewis & Bockius LLP

(57) ABSTRACT

Systems and methods for providing automated inventory management of medicine and healthcare items stored within bins in care facilities are disclosed. A method includes providing an interactive storage device for attaching to a bin, and outputting, via an audiovisual element, a visual representation of a local inventory of the bin, receiving a user input, determining a change to the local inventory according to the user input, updating the local inventory in a non-volatile data store according to the change, synchronizing the local inventory with one or more nodes via a communication interface, and receiving, from the one or more nodes via the communication interface, periodic updates for a local cache comprising locations and inventories of one or more remote bins.

20 Claims, 37 Drawing Sheets

Related U.S. Application Data division of application No. 16/914,186, filed on Jun. 26, 2020, now Pat. No. 11,113,661.

(60) Provisional application No. 62/937,177, filed on Nov. 18, 2019, provisional application No. 62/927,632, filed on Oct. 29, 2019, provisional application No. 62/867,841, filed on Jun. 27, 2019.

(51) Int. Cl.
*G06N 3/08* (2023.01)
*G07C 9/00* (2020.01)
*G07C 9/22* (2020.01)
*H04W 4/80* (2018.01)
*G06Q 10/10* (2023.01)

(52) U.S. Cl.
CPC .......... *G07C 9/00896* (2013.01); *G07C 9/22* (2020.01); *H04W 4/80* (2018.02); *G07C 2009/0092* (2013.01)

(58) Field of Classification Search
CPC ... G07C 9/22; G07C 2009/0092; H04W 4/80; Y02A 90/10; G06F 21/32; G06F 21/35; G07F 17/0092; G16H 20/13; G16H 40/20; G16H 40/63
USPC .......................................................... 705/29
See application file for complete search history.

(56) References Cited

U.S. PATENT DOCUMENTS

| | | | |
|---|---|---|---|
| 2015/0005934 A1* | 1/2015 | Bell | G07C 9/00912 700/237 |
| 2016/0089303 A1* | 3/2016 | Latorraca | G07F 11/62 312/209 |
| 2016/0328813 A1 | 11/2016 | Montgomery et al. | |
| 2017/0161459 A1 | 6/2017 | Bell et al. | |
| 2017/0180359 A1* | 6/2017 | Wolski | H04L 63/0861 |
| 2018/0150613 A1* | 5/2018 | Bossi | G06F 16/2358 |

OTHER PUBLICATIONS

Indian Office Action for Application No. 202117060049, dated Sep. 21, 2023, 7 pages.
Qiu et al., "A survey of machine learning for big data processing", EURASIP Journal Advances in Signal Processing, Mar. 28, 2016, Article No. 67 (2016), https://doi.org/10.1186/s13634-016-0355-x.
International Search Report and Written Opinion for Application No. PCT/US2020/040002, dated Sep. 16, 2020, 14 pages.
International Preliminary Examining Authority Written Opinion for Application No. PCT/US2020/040002, dated Jun. 23, 2021, 6 pages.
International Preliminary Examining Authority International Preliminary Report on Patentability for Application No. PCT/US2020/040002, dated Sep. 6, 2021, 23 pages.

* cited by examiner

```
                            DISPLAY 365A

Content: Alcohol Wipes              Press Take button to subtract qty. ->

Quantity: 100                       Press Receive button to add qty. ->

Battery: 90%                        Network: OK
```

```
                            DISPLAY 365B

Management Mode                     Press Take to change menu item ->

->   Choose item                    Short press Receive to confirm ->
     Set quantity                   Long press Receive to exit ->
     Power management
     Review data logs
```

```
                            DISPLAY 365C

Restock Mode                        Press Take to cycle digits ->

Item description: Alcohol Wipes     Short press Receive to adjust value ->
                                    Long press Receive to exit ->
                  *
Quantity:      [1]    [0]    [0]
```

FIG. 3

DISPLAY 365A

| | | | |
|---|---|---|---|
| Location:<br>Loading Dock | Environment:<br>OK | Authenticated User:<br>D. Green | Patient:<br>J. Doe |
| Destination:<br>St. J. Hospital | ETA:<br>30 minutes | Battery<br>90% | Network:<br>OK |

DISPLAY 365B

Chain of Custody:
2019.10.01 10:00:00 am – S. Max authenticated successfully
2019.10.01 10:01:00 am – S. Max opened lock
2019.10.01 10:05:00 am – S. Max secured lock
2019.10.01 12:00:00 pm – Failed attempt to authenticate
2019.10.01 12:00:01 pm – D. Green authenticated successfully Location History:
2019.09.30 08:00:00 am – Distribution Center
2019.09.30 02:00:00 pm – In transit to Pharmacy
2019.09.30 03:00:00 pm – Pharmacy Inventory History:
2019.09.30 08:00:00 am – Empty
2019.10.01 10:02:00 pm – Drug Name #1, Drug Name #2, Drug Name #3 added Environment History:
2019.09.30 08:00:00 am – OK
2019.09.30 02:30:00 pm – Excess g-force detected: 4 g

DISPLAY 365C

Tote Inventory:
1. Drug Name #1, Dosage 200 mg, Qty X       [+]   [-]   [Remove]
2. Drug Name #2, Dosage 40 mg, Qty Y        [+]   [-]   [Remove]
3. Drug Name #3, Dosage 1000 mg, Qty Z      [+]   [-]   [Remove]
[Add new]

FIG. 9

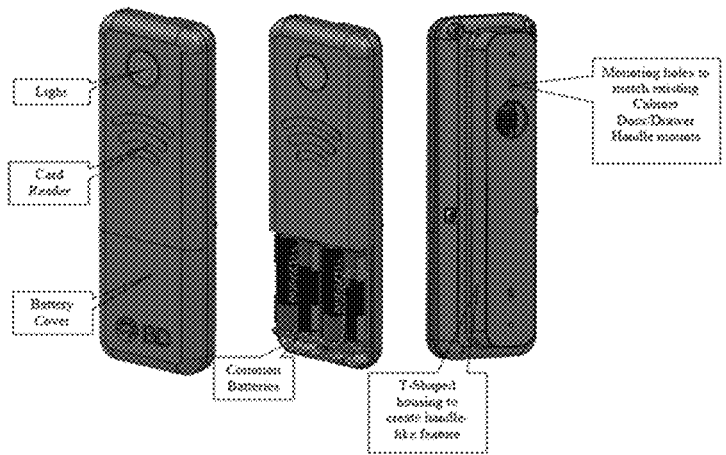
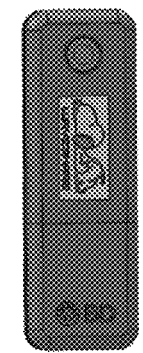
FIG. 13A  FIG. 13B
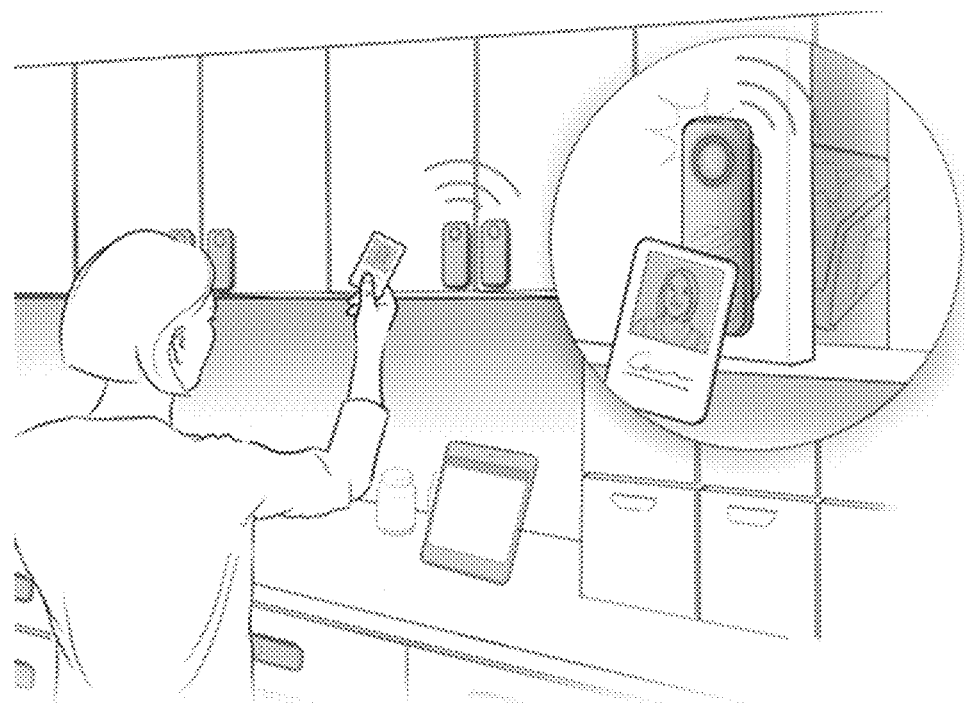
FIG. 14

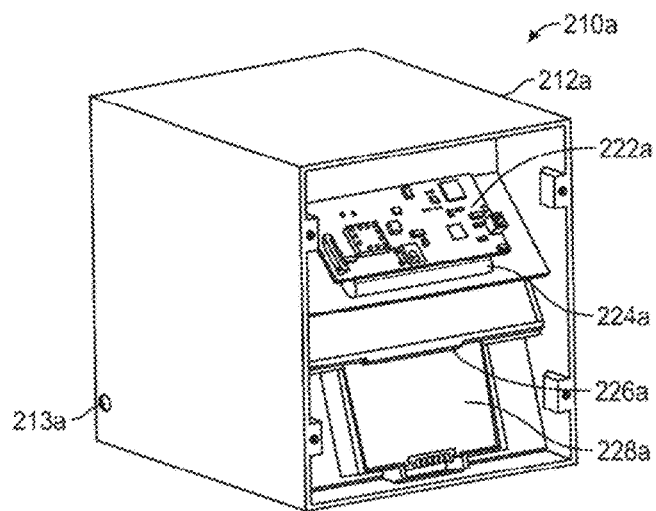
FIG. 24
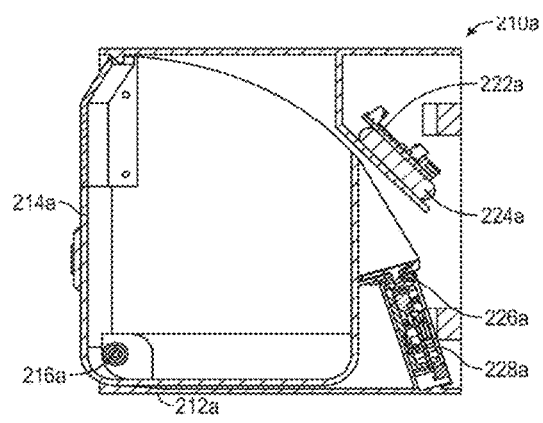 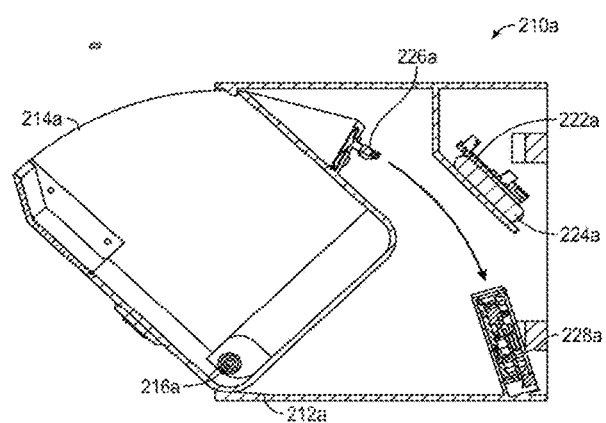
FIG. 25A　　　FIG. 25B

Smart Bud Subsystems

Smart Bin Subsystems

INTERACTIVE INVENTORY STORAGE DEVICE, SYSTEM, AND METHOD

CROSS REFERENCE TO RELATED APPLICATIONS

This application is a continuation of U.S. patent application Ser. No. 17/343,636, entitled "INTERACTIVE INVENTORY STORAGE DEVICE, SYSTEM, AND METHOD," filed on Jun. 9, 2021, now U.S. Pat. No. 11,681,985, which is a divisional application of U.S. application Ser. No. 16/914,186, entitled "INTERACTIVE INVENTORY STORAGE DEVICE, SYSTEM, AND METHOD," filed on Jun. 26, 2020, now U.S. Pat. No. 11,113,661, which claims the benefit of U.S. Provisional Application No. 62/867,841, entitled "SECURE AND EFFICIENTLY DEPLOYABLE MEDICATION DISPENSING," filed on Jun. 27, 2019, and claims the benefit of U.S. Provisional Application No. 62/927,632, entitled "SMART TOTE," filed on Oct. 29, 2019, and claims the benefit of U.S. Provisional Application No. 62/937,177, entitled "INTERACTIVE CONNECTED INVENTORY DEVICE," filed on Nov. 18, 2019, the entirety of each of which is incorporated herein by reference.

TECHNICAL FIELD

The present disclosure generally relates to device for inventory access and management, and more specifically relates to methods and systems for providing secure storage, transport and dispensing of items using an interactive connected inventory devices.

BACKGROUND

To organize and dispense items in both acute and non-acute medical settings, bins may be provided. While such bins may be readily procured, they lack smart functionality and management features. This poses several drawbacks of heightened concern for care facilities, such as doctor's offices, pharmacy clinics, outpatient clinics, institutional infirmaries (e.g., school nurse offices), hospitals, retail clinics, ambulatory clinics, or the like.

For example, without smart functionality and management features, inventory management must be carried out manually, which is prone to human error. It may also be difficult to maintain efficient levels of medications and other medical inventory, which results in procedural delays from understock and waste or spoilage from overstock. Further, it can be difficult to identify the location of a particular item or bin or tote for restocking or dispensing, especially in a large clinical setting with many rooms.

Moreover, to transport items such as medication in both acute and non-acute medical settings, conventional transport devices such as paper bags and other moveable storage vessels lack processors and circuitry to enable smart functionality. This lack of smart functionality poses several drawbacks of heightened concern for care facilities, such as doctor's offices, pharmacy clinics, outpatient clinics, institutional infirmaries (e.g., school nurse offices), hospitals, retail clinics, ambulatory clinics, or the like. For example, controlled or non-controlled medications may require specific environmental conditions, such as temperature and humidity, to be maintained within a safe range, which cannot be monitored using a conventional storage vessel. Additionally, since the contents of such storage vessels are accessible to anyone in physical proximity, the contents may be easily lost, tampered, stolen, or diverted. While zip-ties or other devices may be used to seal vessels, these insecure methods may be easily bypassed and reapplied by a determined attacker, thus providing minimal deterrent effect and unreliable auditing. Inventory management is also typically done manually, which is prone to human error and may mask or delay loss detection. Further, it can be difficult to identify the location and responsible party of a particular transport vessel at a particular time. Institutional policy enforcement thus becomes difficult or impossible to carry out.

Accordingly, there is a need for improved systems and methods of storing, transporting, dispensing, and inventory management of items, particularly for medicine and other healthcare items used in clinical settings.

SUMMARY

According to various aspects of the subject technology, a method for using an interactive connected inventory device to provide inventory management for items stored in bins and other containers (e.g., trays, baskets, jars, shelves, or other item storage locations) comprises: providing an interactive connected inventory device for attaching to a bin, outputting, via an audiovisual element, a visual representation of a local inventory of the bin, receiving, via a user interface, a user input, determining a change to the local inventory according to the user input, updating the local inventory in a non-volatile data store according to the change, and synchronizing the local inventory with a remote server via a communication interface. Other aspects include corresponding systems, apparatuses, and computer program products for implementation of the method.

According to various aspects of the subject technology, an inventory device comprises a memory including a non-volatile data store containing a local cache storing a local inventory of a container; a communication interface; an audiovisual element; and a processor configured to: output, via the audiovisual element, a visual representation of the local inventory; receive a user input; determine a change to the local inventory according to the user input; update the local inventory in the non-volatile data store according to the change; synchronize the local inventory with one or more nodes via the communication interface; and receive, from the one or more nodes via the communication interface, periodic updates for the local cache comprising locations and inventories of one or more remote bins.

According to various aspects, the inventory device may further comprise: an actuator configured to open and close a lock to secure a lid of the container; wherein the processor is further configured to: receive user credentials for accessing the tote; validate the user credentials for accessing the container; trigger the actuator to open the lock, thereby allowing the lid to be opened; determine a change in contents of the container; update, in the non-volatile data store, an inventory according to the change in contents of the container; trigger the actuator to close the lock after detecting that the lid is closed, thereby securing the lid; and record the user credentials, one or more timestamps, and the change in contents in an access log within the non-volatile data store. Other aspects include corresponding methods, systems, and computer program products for implementation of the device.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIG. 3 depicts various example user interfaces of an interactive connected inventory device, according to various aspects of the subject technology.

FIG. 9 depicts various example user interfaces of a smart tote controller, according to various aspects of the subject technology.

FIGS. 13A and 13B depict a remote smart lock reader module configured to unlock a securable container, according to various aspects of the subject technology.

FIG. 14 depicts the remote smart lock reader module added to existing cabinet doors and/or existing cabinet drawers for controlled security, according to various aspects of the subject technol.

FIG. 24 depicts an example outer housing of a bin assembly with an electro-mechanical latch, PCBA, and battery, according to various aspects of the subject technology.

FIGS. 25A and 25B depict cut-away views of an example disclosed storage bin, including a hook that interfaces with the disclosed electro-mechanical latch, according to various aspects of the subject technology.

DESCRIPTION

Figure 1A:
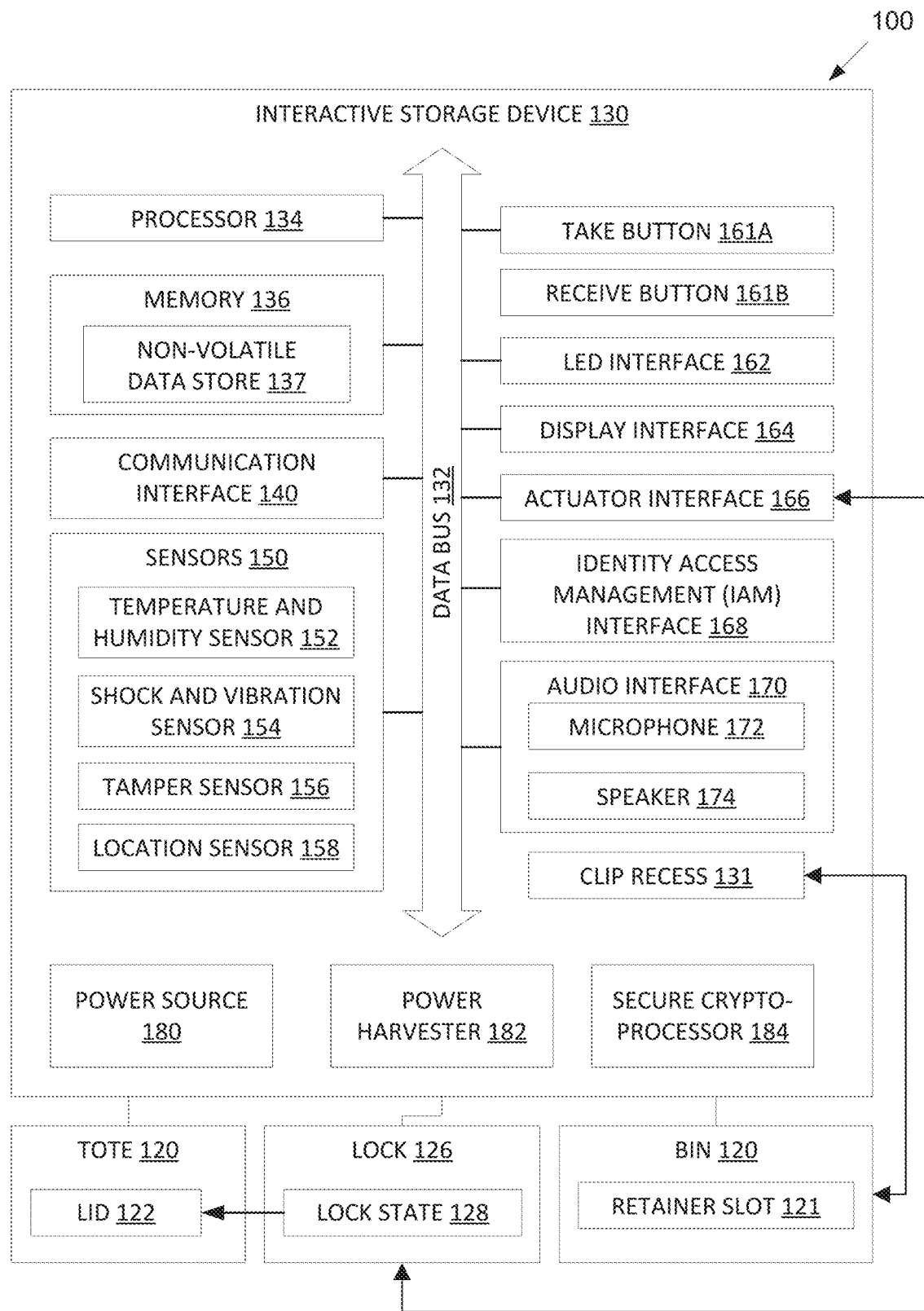
FIG. 1A depicts an example system including an interactive connected inventory device, according to various aspects of the subject technology.

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

Storage, transport, and dispensing of medicine and other healthcare items demand robust inventory management to prevent medicine spoilage, reduce overhead, and minimize costly diversion, theft, and other losses. Various systems may exist to address individual aspects of these demands, such as systems that provide only cold chain tracking of medications requiring temperature regulation. However, combining various disparate systems to address the multiple requirements of medicine transportation may be costly, unwieldy, and difficult or impossible to implement in practice.

For example, to minimize and discourage the costly diversion of medicines, it may be preferable to include a high level of security, for example via a separate or integrated crypto-processor. In this manner, any evidence identifying a diversion can be maintained and relied upon with a high degree of confidence. However, it may be architecturally impossible to interface various disparate systems with the crypto-processor, as the various systems may become weak links that are easily susceptible to attack vectors. The disparate systems may also be closed source or otherwise undocumented or obfuscated, making secure integration difficult or impossible.

The subject technology provides an integrated, enterprise grade, automated inventory management system to address the numerous requirements of medicine and healthcare item dispensing in care facilities. According to various implementations, an inventory storage device is provided that can be dynamically attached to a bin or container, thereby transforming the bin or container into a network connected container with "smart" functionality. Smart functionality generally refers to processing and connectivity capabilities. A smart device can have on-board memory or other storage capacity that can be written to and read from. The memory can contain one or more applications for implementing a particular function. The particular smart device may also contain an operating system and/or user interface. Some smart functionality may include wireless communications. For example, a smart device may include a transceiver for communicating through an electric field and/or magnetic field between the device and another entity such as a wireless terminal or information reader.

The interactive storage device may include various interfaces and devices to support other smart features such as environmental sensing, tamper detection, infrastructure and mesh networking, near-field communications, positional tracking, and user interfaces with audiovisual elements for inventory management, alerts, and user guidance. In this manner, the inventory device can interface and synchronize with a centralized back-end server to support inventory tracking, item condition tracking, and data collection for machine learning (e.g., as described in further detail in conjunction with FIGS. 2A and 2B below).

According to various implementations, the disclosed interactive inventory storage device 130 may include a smart tote controller (e.g., a smart tote controller 130A or 130B of FIG. 6) that can be attached to the lid of existing, off the shelf totes, thereby transforming the tote into a smart tote with smart functionality. In some implementations, the smart tote controller is embedded in a hasp lid that is attached to the top of an existing lid. The interactive storage device (or controller) may interface with an actuator that can lock and unlock the lid of the tote to provide access control. For example, a smart tote controller may require user authentication before unlocking the tote, wherein the access time and the authorized user may be recorded in a secure, encrypted access log.

As will be described further, the disclosed devices of the subject technology may include various interfaces and devices to support other smart features such as environmental sensing, tamper detection, infrastructure and mesh networking, near-field communications, positional tracking, and user interfaces with audiovisual elements for inventory management, alerts, and user guidance. In this manner, the devices of the subject technology may interface and synchronize with a centralized back-end server to support chain of custody tracking, inventory tracking, and item condition tracking (e.g., as described in further detail in conjunction with, e.g., FIGS. 1F and 1G below).

FIG. 1A depicts an example system 100 for implementing the disclosed interactive inventory storage device 130, according to various aspects of the subject technology, bin or tote 120 includes retainer slot 121. Interactive inventory storage device 130 includes clip recess 131, processor 134, memory 136, communication interface 140, sensors 150, button interface 160, LED interface 162, display interface 164, actuator interface 166, identity access management (IAM) interface 168, audio interface 170, power source 180, power harvester 182, and secure crypto-processor 184. Memory 136 may include non-volatile data store 137.

According to various implementations, interactive inventory storage device 130 may include or be embodied as an electronically securable bin or tote 120 that includes or is associated with an access controller for operating an electronically securable container. For example, the access controller may be attached to the bin or tote (e.g., on the front of the container, adjacent a lid 122.) In this regard, access controller and the container may be referred to together as an interactive inventory storage device 130. According to various aspects, the access controller may be referred to separately, for example, as a smart bin controller or smart tote controller or smart card reader.

Sensors 150 include temperature and humidity sensor 152, shock and vibration sensor 154, tamper sensor 156, and location sensor 158. Button interface 160 may include a take button 161A and a receive button 161B. Audio interface 170 includes microphone 172 and speaker 174. The components included in interactive inventory storage device 130 are exemplary and other implementations may include a different configuration of components according to use case requirements, power consumption targets, and price point constraints.

Interactive inventory storage device 130 may include clip recess 131, which allows easy attachment to bin or tote 120 via a corresponding retainer slot 121. This is illustrated in greater detail in conjunction with FIG. 1C, FIG. 1D, and FIG. 1E below. Retainer slot 121 may correspond to a card slot that conventionally receives a description card, but is instead advantageously used as a retainer slot for interactive inventory storage device 130.

Interactive inventory storage device 130 may include processor 134, which may correspond to any type of general or specialized processor, controller, integrated circuit, application specific integrated circuit (ASIC), field programmable gate array (FPGA), system-on-chip, or similar device, and may include hardcoded circuit elements, firmware, software, or any combination thereof to implement one or more of the features described herein. Processor 134 may communicate with other components of interactive inventory storage device 130 via data bus 132, which may comprise one or more communication buses, such as parallel or serial buses.

Interactive inventory storage device 130 may include memory 136, which may include volatile work memory as well as non-volatile data store 137 for long term data storage. For example, non-volatile data storage 137 may comprise flash memory or other memory that retains data after power source 180 is unavailable. Non-volatile data store 137 may include several data logs that record, for example, user authentication events, periodic sensor data, location history, and local inventory of bin or tote 120.

Communication interface 140 may include one or more wireless radios to communicate with other devices and/or other interactive storage devices. For example, communication interface 140 may include one or more radios, scanners, or other devices that are compliant with Bluetooth, Bluetooth Low Energy, Near Field Communication (NFC), Wi-Fi, contactless Smartcards, Radio-Frequency identification, 1-D and 2-D barcodes, and other protocols. Sensors 150 may include one or more sensors to record, for example, environmental conditions and evidence related to attempts to divert or tamper with the contents of bin or tote 120. For example, temperature and humidity sensor 152 may record ambient temperature and humidity to assist in determining whether the contents of bin or tote 120 remain safe and effective to use. Shock and vibration sensor 154 may help to determine whether an attempt to divert has occurred, or whether the contents of bin or tote 120 were damaged during transport, shipping, and/or handling. For example, measurements from the shock and vibration sensor 154 may be monitored in real time or periodically audited for shock or vibration measurements that correspond to a detection threshold. If a measurement or series of measurements correspond to the threshold, the interactive inventory storage device 130 (or other monitoring device in communication therewith) may adjust the interactive inventory storage device 130 or other element in the environment. Tamper sensor 156 may determine whether case intrusion has occurred, for example if retaining screws, latches, covers, or other components of interactive inventory storage device 130 have been opened, unsealed, drilled, deformed, or otherwise tampered. For example, mechanical switches, anti-tamper films, photodiodes with reflective materials, infrared proximity sensors, and other devices may be used.

Location sensor 158 may include, for example, a global positioning system (GPS) radio to enable location history tracking. Location information generated by the location sensor 158 may be monitored in real time or periodically audited to identify deviations from expected location or route for the interactive inventory storage device 130. If a measurement or series of measurements differ from the expected location(s), the interactive inventory storage device 130 (or other monitoring device in communication therewith) may adjust the interactive inventory storage device 130 or other element in the environment. Adjustments may include adjusting a power state of the controller or lock 126, transmitting a control message to the actuator interface 166 to adjust the lock state 128, activating an interface of the controller to provide a perceivable indicator of the detected state, or the like. Alternatively or additionally, in some implementations, triangulation may be used to determine location, for example by using Wi-Fi or Bluetooth triangulation using known networks and/or hubs and/or beacons. In combination with secure crypto-processor 184, sensors 150 may securely record real-time sensor data to comply with National Institutes of Standards and Technology (NIST) requirements.

In some implementations, one or more of the sensors 150 may be used to identify when a user is near an interactive storage device. For example, an infrared proximity sensor may be directed away from the container to detect an area in front of the container. When a user is detected within the area, the interactive storage device may adjust one or more functions such as entering a different power mode, activating wireless communications or a display, or enabling one or more of the button interfaces. In this way, the interactive storage device can preserve resources such as battery, memory, or network bandwidth. The detection may be based on a duration of time. By including time, the device may avoid waking or adjusting state for a clinician simply passing by who may only be within the area for a short period of time. Presence in the area for a duration of time longer than the threshold may indicate intent to interact with the inventory device. In such instances, the presence within the area for at least the threshold period of time may cause the activation, power mode change, activation of a communication interface (e.g., wireless transceiver, Bluetooth radio), or other adjustment of the interactive storage device.

Button interface 160 may enable user input and selections on a user interface. For example, display interface 164 may show a user interface directing the user to push specific buttons to update inventory, e.g. take button 161A to take or decrement a stock counter for an item, and receive button 161B to receive or increment the stock counter for the item. In some implementations, button interface 160 may not use physical buttons and may use capacitive or resistive touchscreens or buttons. Alternatively or additionally, display interface 164 may provide a touchscreen panel to accept user input. In some implementations, user input may be received from a remote device, such as a tablet or smartphone, via communication interface 140.

In some implementations, the individual buttons of button interface 160 may change function depending on user interface context. For example, during management tasks, button interface 160 may be used to navigate on-screen menus. For example, presses of take button 161A may be used to cycle between menu options, a short press of receive button 161B may be used to confirm a selection, and a long press of receive button 161B may be used to exit a menu or cancel a selection. In another example, during inventory loading, button interface 160 may be used to set and verify loading quantities of items. For example, presses of take button 161A may change a digit position, short presses of receive button 161B may cycle between numbers of the current digit position, and long presses of receive button 161B may confirm a quantity of items.

Light emitting diode (LED) interface 162 may drive one or more multi-color LEDs or organic LEDs (OLEDs) for providing a quickly identifiable status indication. For example, LEDs may be driven at varied brightness, blinking patterns, and colors to indicate various states of interactive inventory storage device 130. In one configuration, solid red LEDs may indicate that sensors 150 have recorded potentially unsafe environmental conditions for the contents of bin or tote 120, such as temperature outside of a safety range for medicines, whereas solid green LEDs may indicate that sensors 150 have recorded environmental conditions within safe parameters. In some implementations, blinking green LEDs may indicate that an authorized user has submitted valid credentials for unlocking lock 126 to access contents of the bin or tote 120. In some implementations, blinking green LEDs may indicate that a stock level of items in bin or tote 120 has fallen below a predetermined threshold. Blinking red LEDs may indicate that tamper sensor 156 and/or shock and vibration sensor 154 have recorded an intrusion attempt, for example if a detected deformation, vibration or shock value exceeds a predetermined threshold. Blinking yellow LEDs may indicate that power source 180 has crossed a low battery threshold and needs replacement. Blinking white LEDs may visually identify bin or tote 120 to the user, allowing the user to readily identify bin or tote 120 associated with a requested item from a collection of bins in a pharmacy, stock room, or other facility. Further, in some implementations, the LED blinking patterns may be detected by a handheld scanner or another device to assist in inventory tracking and management, as described further below.

Display interface 164 may drive a display to show various user interfaces enabling a user to query the inventory of bin or tote 120, to update the local inventory of bin or tote 120 by adding or removing items, to query the condition of the items, to display remaining battery life, to show location history and/or chain of custody, to show timestamped inventory change history and authentication event history, and to perform other management and status query operations. The user interfaces may utilize text and graphics such as icons, animations, and other elements. In some implementations, these user interfaces may additionally or alternatively be presented on a remote device, such as a tablet or smartphone. Display interface 164 may drive an electronic ink (e-ink) display, a touchscreen liquid crystal display (LCD), an OLED, or another display type. The information may be presented on the display interface 164 in human readable form (e.g., letters, numbers, or images) or machine-readable form (e.g., barcode, quick read code, standardized scan code form, or custom scan code form).

Actuator interface 166 may actuate lock 126 to change lock state 128 from open to closed and vice versa. For example, lock 126 may correspond to an electromechanical lock or an electromechanical latch. Actuator interface 166 may also query lock 126 to determine lock state 128. For example, actuator interface 166 may query general purpose I/O pins or another data bus from a cable (e.g. actuator cable 133 in FIG. 1D) connected to lock 126 to read lock state 128. Actuator interface 166 may store a local copy of lock state 128 in a non-volatile memory of actuator interface 166. In some implementations, a manual lock may be provided to manually lock and unlock lock 126 without using actuator interface 166. In this case, any manual locking or unlocking action may be detected by actuator interface 166 and recorded within an access log in non-volatile data store 137. A manual lock may be useful to provide access to the contents of tote 120 when interactive inventory storage device 130 malfunctions or when power source 180 is exhausted and no replacement is readily available.

In some implementations, an identity access management (IAM) interface 168 may include one or more devices to enable a user to provide credentials for user authentication. In this case, interactive inventory storage device 130 may direct, via communication interface 140, a smart latch or smart lock to open a door or latch providing access to the interior of bin or tote 120. For example, the IAM interface 168 may include one or more biometric scanners, such as a fingerprint sensor, an iris scanner, an electrocardiogram (ECG) reader such as a smartwatch, and a depth camera for facial recognition. The IAM interface 168 may also include smartcard readers or other devices to read a contactless smartcard or other unique identifier or token. In some implementations, the IAM interface 168 may use communication interface 140 to utilize biometric scanners or readers present on a remote device, such as a tablet or smartphone. Accordingly, the IAM interface 168 may receive user credentials which can be validated in conjunction with secure crypto-processor 184.

When multiple authentication methods are available in the IAM interface, then a particular authentication method may be automatically selected for authentication. For example, the authentication methods may be sorted according to security strength, and the methods with the highest security strength may be preferred for use. In some implementations, the user may select the preferred method of authentication.

Further, a super user or a user with elevated privileges may manually authenticate a user, for example if the user misplaces his credentials.

Audio interface 170 may include one or more audio devices, such as microphone 172 and speaker 174. Microphone 172 may enable voice commands to be used instead of button interface 160 or display interface 164. Speaker 174 may enable audio prompts, feedback, and alerts to be emitted. Speaker 174 may comprise a piezoelectric speaker, a dynamic speaker, or another type of speaker. For example, different tones may be emitted from the piezoelectric speaker to indicate different states or user prompts.

Power source 180 provides electrical power for the components of interactive inventory storage device 130. Power source 180 may comprise a non-rechargeable battery, a rechargeable battery, a capacitor or super-capacitor, or another energy storage device. Power source 180 may be user accessible and replaceable. To supplement or recharge power source 180, power harvester 182 may be used to receive power from external sources. For example, power harvester 182 may receive wireless power through inductive coils or RF sources. Power harvester 182 may also receive power through mechanical action, such as via piezo transducers interfaced to buttons connected to button interface 160, or via electromagnetic induction induced by actuation movement of a lock or sliding drawer. Power harvester 182 may also receive power through direct wired connection, such as via universal serial bus (USB) charging cables, AC-DC chargers, or DC-DC chargers, which may be plugged into an external battery pack or wall mains voltage supply. In the event that power source 180 is depleted, lock state 128 may be maintained in its current state, whether closed or open, until power source 180 is replaced or a manual lock is engaged, when made available.

To extend the operating time of power source 180, various power management strategies may be utilized. For example, interactive inventory storage device 130 may be placed in a low power or sleep state when no activity is anticipated. When activity such as user interactions, periodic network updates, or sensor logging is necessary, interactive inventory storage device 130 may wake up to a normal operating mode, and return to the low power or sleep state once the activity is completed. The estimation of low activity may be based on network activity, user preferences, working schedules, or other factors. Interactive inventory storage device 130 may also wake up in response to an activation word or phrase via microphone 172, a button press on button interface 160, or a touch input from display interface 164. In some implementations, sensors 150 may include occupancy sensors which may be used to determine estimated activity levels. In some implementations, microphone 172 may be used as an occupancy sensor. In some implementations, power management may be based on machine learning algorithms, as described in further detail below in FIG. 2A.

In some implementations, the power management strategies may include utilizing machine learning to generate a power profile. For example, each smart tote controller may log usage data in non-volatile data store 137, which can then be collected by a remote server and processed by one or more machine learning algorithms to determine a power management profile for optimized power consumption. For example, the power management profile may define daily time periods when user interactions are infrequent, and processor 134 may use this profile to transition processor 134 and other components to a low power idle or sleep mode during these daily time periods.

Secure crypto-processor 184 may correspond to a trusted platform module (TPM) chip that stores public and private encryption keys for encrypting and decrypting data. For example, the public keys may include public keys of key pairs generated by authorized users, allowing each user to submit credentials encrypted by a respective private key for decrypting by secure crypto-processor 184. Similarly, private keys specific to interactive inventory storage device 130 can be used to encrypt data before transmitting, storing, and exposing the data to the outside world. In this manner, data travelling through data bus 132 and stored in memory 136, including non-volatile data store 137, can be securely encrypted to protect against third party eavesdropping and modification. Encrypted data can also be more safely transmitted to the outside world, including over potentially insecure and untrusted networks.

In some implementations, the components of interactive inventory storage device 130 may be hardened against extreme temperatures. For example, the components of interactive inventory storage device 130 may be configured to be operable within a refrigerated environment. In this manner, interactive inventory storage device 130 may be attached to bins stored in refrigerators, freezers, or other cold storage.

Figure 1B:
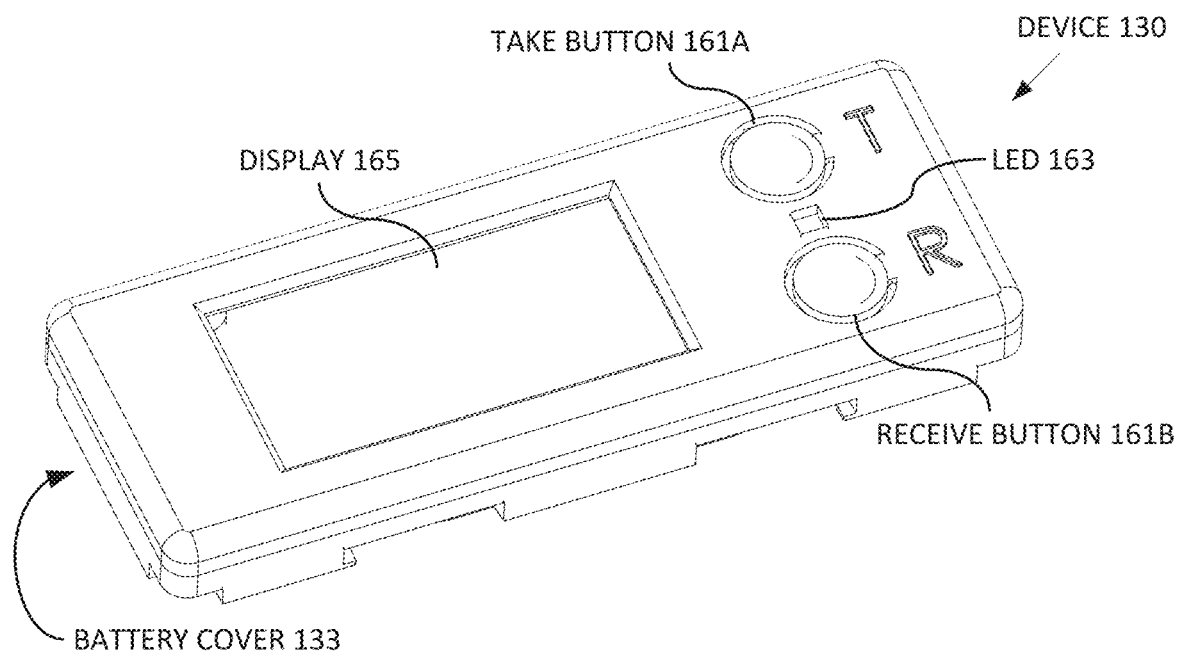
FIG. 1B and FIG. 1C depict perspective views of front and rear surfaces of an example interactive connected inventory device, according to various aspects of the subject technology.

FIG. 1B depicts a perspective view of a front surfaces of interactive inventory storage device 130, according to various aspects of the subject technology. In some implementations, the example interactive inventory storage device 130 may be shown and described herein as an access control device, or interactive tote controller, that is separate from a bin or tote 120. In some implementations, while the interactive inventory storage device 130 may be shown and described as a separate controller, the description herein regarding the device 130 may apply to both the controller and a bin or tote 120 as a single unit or connected configuration.

As shown by FIG. 1B, interactive inventory storage device 130 may include or be referred to a remote smart controller 130, or device that operably connects to one or more bins or totes 120 to control the bin(s) or tote(s), or to send or receive data therefrom. In this regard, the device 130 may be associated with a bin assembly 200 or one or more bins within an assembly or assemblies. The device 130 may further connect to server 114 to provide data to server 114 from the bin(s) and to receive instructions from server 114 for controlling operation of a bin (e.g., to open or lock the bin). The front surface of interactive inventory storage device 130 includes battery cover 133, take button 161A, receive button 161B, LED 163, and display 165.

Referring to FIG. 1A, various interfaces may drive or control the components of interactive inventory storage device 130. For example, button interface 160 may receive user inputs from take button 161A and receive button 161B, such as short or long button presses. LED interface 162 may drive LEDs 163, which may display light of varying intensity, colors, and flashing patterns, as previously described. Display interface 164 may drive display 165, which may display status messages and various user interfaces for managing interactive inventory storage device 130 and the contents of bin or tote 120. Battery cover 133 may protect power source 180 and may be user accessible for easy replacement of power source 180. The specific elements shown in interactive inventory storage device 130 are exemplary and any configuration of elements may be utilized according to use case requirements.

Figure 1C:
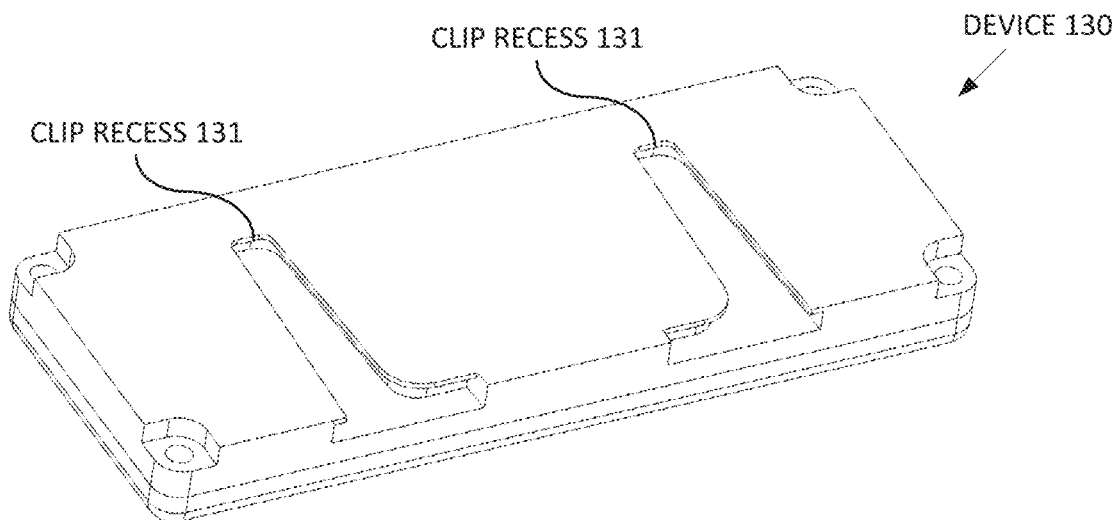
Figure 1D:
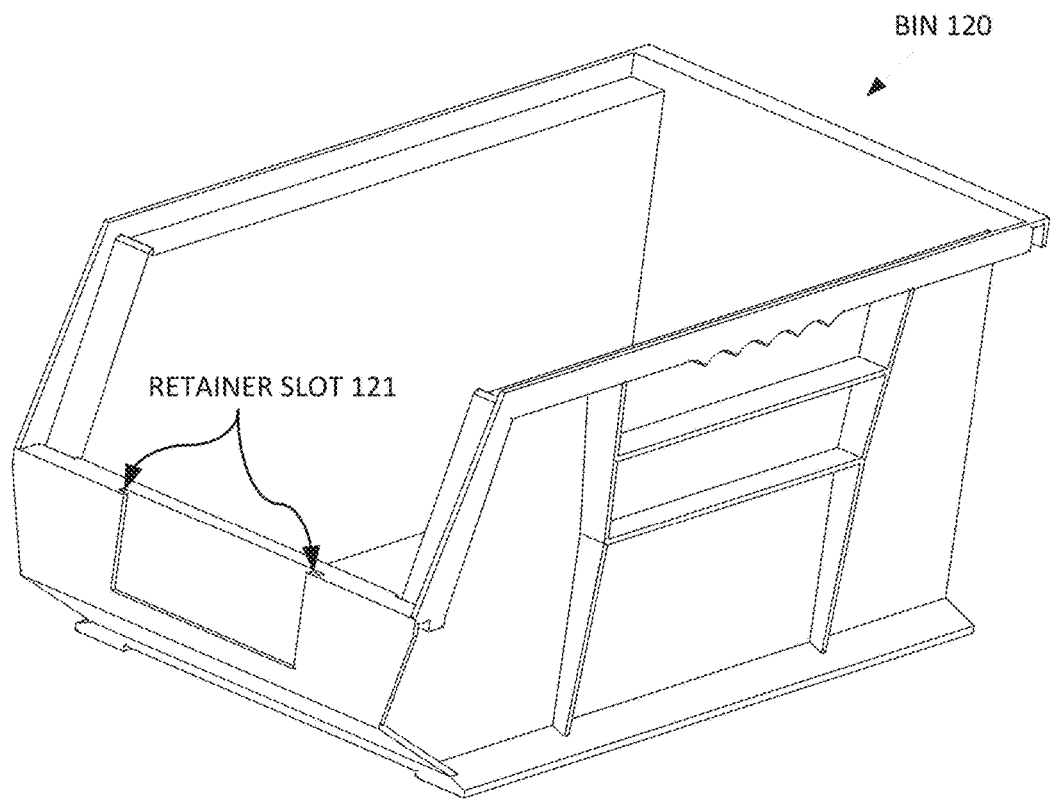
FIG. 1D depicts a perspective view of an example bin, according to various aspects of the subject technology.
Figure 1E:
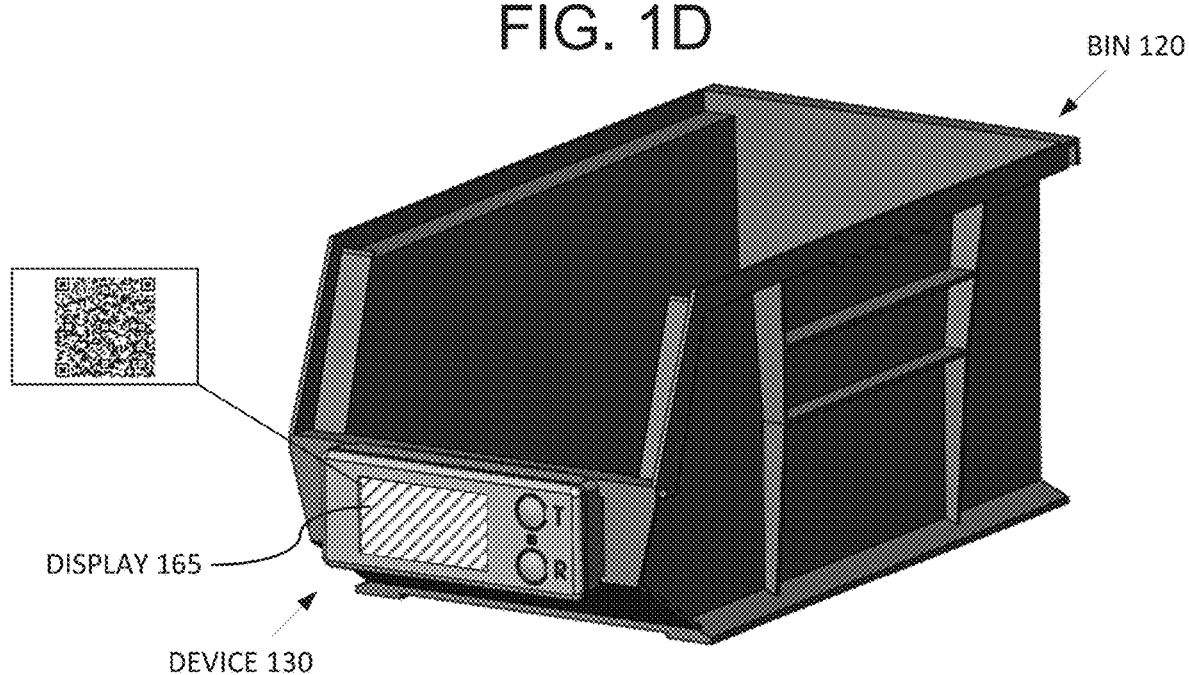
FIG. 1E depicts a perspective view of the example interactive connected inventory device from FIGS. 1B and 1C attached to the example bin or tote of FIG. 1D, according to various aspects of the subject technology.

FIG. 1C depicts a perspective view of a rear surface of interactive inventory storage device 130, according to various aspects of the subject technology. The rear surface of interactive inventory storage device 130 includes clip recess 131. Referring to FIG. 1A, clip recess 131 may be configured to easily slide into retainer slot 121, as shown in FIGS. 1D and 1E below. In some implementations, a button or other mechanical switch may be situated within the clip recess 131 such that when the interactive inventory storage device 130 is not attached to a container, the button is in a first state. Similarly, the button will enter a second state when the interactive inventory storage device 130 is attached to the container. The button may cause an adjustment to the interactive inventory storage device 130 such as adjusting the power state (e.g., on/off, sleep/wake, etc.), activating wireless transceiver (e.g., WIFI or BLUETOOTH™ compliant radio), activating the display 165 or the LED 163, or the like.

Additionally or alternatively a light sensor may be located within the clip recess 131 such that when the inventory device 130 is detached, light may be received by the light sensor and when the inventory device 130 is attached to a container, the light sensor may be blocked thereby cutting off light to the light sensor. This may be used to determine the attachment state of the interactive inventory storage device 130.

The clip recess 131 is one example of an attachment surface that may be included on the interactive inventory storage device 130 to attach the device 130 to a container. The attachment surface may include adhesive for mounting to the container. The attachment surface may include magnetic or mechanical mountings to secure the inventory device 130 to an accessible portion of the container.

As discussed, the attachment surface may include an attachment sensor configured to detect attachment or detachment between the attachment surface and the container. The inventory device 130 may receive a message from the attachment sensor indicating detachment from the container. In response, the inventory device 130 may transmit an alert message indicating the detachment. Transmitting the alert message may include causing emission of a perceivable output from an output device included in the inventory device 130 such as the LED, display, or audio output. Transmitting the alert message may additionally or alternatively include transmitting the alert message via a communication interface to a remote device such as a central management/monitoring system. In some implementations, one or more interface elements of the inventory device 130 may be activated to indicate detachment from a bin. In such instances, it may be desirable to program a pattern of inputs that will authorize detachment without generating alarms. For example, if a technician is cleaning the container, the technician may first enter the authorization sequence. The inventory device 130 may then provide a perceivable indication that detachment is permitted after confirming the authorization sequence. A secure log of this activity may also be stored in a storage element of the inventory device 130 or transmitted via a communication interface. If an attempt is made to remove the device 130 without entering the pattern, the inventory device 130 may provide one or more of the perceivable alerts or messages described. The pattern encoding may be used to selectively enable or disable other features of the inventory device 130 described herein.

FIG. 1D depicts a perspective view of bin or tote 120, according to various aspects of the subject technology, bin or tote 120 may correspond to an off-the-shelf bin, and may include retainer slot 121. Conventionally, retainer slot 121 may be used to receive an identification card or paper that describes the contents of bin or tote 120. However, by configuring the rear surface of interactive inventory storage device 130 with clip recess 131 as shown in FIG. 1C, retainer slot 121 may be also used to receive interactive inventory storage device 130 directly without using extra attachment means such as tape, hook and loop fasteners, glue, or screws.

FIG. 1E depicts a perspective view of interactive inventory storage device 130 from FIGS. 1B and 1C attached to bin or tote 120 of FIG. 1D, according to various aspects of the subject technology. As shown in FIG. 1E, interactive inventory storage device 130 can be securely attached to bin or tote 120 via clip recess 131 and retainer slot 121.

In some implementations, a remote device such as a tablet, smartphone, laptop, or other device may be used to interface with interactive inventory storage device 130. For example, the remote device may include an optical scanner that can read 1D or 2D barcodes and/or LED flashing patterns to receive encoded data from interactive inventory storage device 130. Accordingly, interactive inventory storage device 130 may display a QR code or another barcode, as shown in display 165 of FIG. 1E. The scanner may be a wireless signal scanner such as near field communication (NFC) scanner to exchange data with the interactive inventory storage device 130. The scanner may be used, for example, to determine the correct medications to load into a bin or tote by using the scanner to identify interactive inventory storage device 130. For example, interactive inventory storage device 130 may include an embedded unique identifier or serial number that can be transmitted using barcodes or LEDs or an NFC signal. The remote device may contact a remote server, e.g. a pharmacy server, to determine, for example, a type and quantity of medications to be added bin or tote 120 based on the identifier. Pharmacy and local bin or tote inventories may also be automatically updated according to the expected change in contents of bin or tote 120. In some implementations, the bins may already be loaded with medications, and the user only needs to identify the correct bin or tote from a collection of bins. For example, as discussed above, LED lights may blink on a specific interactive storage device to identify the bin or tote to the user. A similar process may be used for dispensing medications from bins.

The remote device may execute a local application downloaded from an application store, a corporate network, a website, or another distribution method. Alternatively, the remote device may execute a remote cloud-based application or a Software as a Service (SaaS) application. The application may allow communication with interactive storage devices such as interactive connected inventory device 130. For example, the application may utilize radios that support various protocols such as Bluetooth, Bluetooth Low Energy, Near Field Communication (NFC), Wi-Fi, contactless smartcards, Radio-Frequency identification, and others.

The interactive connected inventory device 130 may be permanently affixed to the bin or tote 120 or removeably attached to the bin or tote 120. In some implementations, the bin or tote 120 may include a lid. The lid may be secured through an electromechanical lock that can be activated or deactivated by the interactive connected inventory device 130. For example, if a user attempts to remove an item from a bin or tote including a lid, in the secured state, the lid will prevent dispensing of the item. Once a user activates a button or other control element of the interactive connected inventory device 130 to indicate the intent to take (or return) the item, the inventory device 130 may transmit a control message to the lock of the bin or tote to which the inventory device is paired to release the lid.

When the remote device is connected to a network, such as via a Wi-Fi or cellular connection, interactive inventory storage device 130 may utilize the network to communicate and synchronize with a remote server, as described in further detail below in conjunction with FIG. 2A and FIG. 2B. Alternatively, when such a connection is not present, interactive inventory storage device 130 may utilize mobile mesh networking to use other interactive storage devices as nodes to connect to the remote server. In some implementations, a cellular modem may be included within interactive inventory storage device 130 to provide a direct cellular connection to the remote server. However, to reduce implementation complexity and data network costs, it may be preferable to omit a cellular modem.

With an overview of various interactive storage device implementations now in place, it may be helpful to observe the operation of multiple interactive storage devices in an example networked environment. FIG. 2A depicts system 200 using interactive storage devices 230A through 230G in networks 118 and 119 to provide automatic inventory management of items in corresponding bins with inventory tracking 215, item condition tracking 116, and machine learning 117, according to various aspects of the subject technology. FIG. 2A includes hospital 110, server 114, network 118, and mobile mesh network 119. Hospital 110 includes patient room 111, supply room 112, interactive inventory storage device 130C, and interactive inventory storage device 130D. Patient room 111 includes interactive storage device 230A, interactive inventory storage device 130B, and hub 190A. Supply room 112 includes interactive inventory storage device 130E, interactive inventory storage device 130F, interactive inventory storage device 130G, and hub 190B. Server 114 includes inventory tracking 115, item condition tracking 116, and machine learning 117. For simplicity of discussion, each interactive storage device may be attached to a corresponding bin, which is not specifically shown. With respect to FIGS. 2A and 2B, each interactive inventory storage device 130A-130G may correspond to interactive inventory storage device 130 from FIG. 1A-1E.

Server 114 may use inventory tracking 115 to track an inventory of each uniquely identifiable interactive storage device and associated bin. Server 114 may connect to interactive storage devices 130A-130G via network 118 and hubs 190A and 190B. Hubs 190A and 190B may be connected to an infrastructure network of hospital 210 having access to a public network, such as network 118, which may comprise the Internet. In some implementations, a cellular router, hub, gateway, modem, or another network device may be provided at hubs 190A and 190B or in each individual interactive inventory storage device 130A-130G to provide a connection to network 218. In this manner, the interactive storage devices can be immediately deployed without requiring potentially costly and time consuming integration into existing information technology (IT) infrastructure at hospital 110.

A user may use a remote device, such as a tablet or smartphone, to request identification of a bin or tote storing a particular item, such as medication or medical supplies. The interactive storage device may then identify itself to the user by outputting to an audiovisual element, such as by a blinking LED, emitting a sound, or a combination. The type of output may change depending on detected proximity to the remote device, for example by using beeps when the remote device/user is far away, and blinking LEDs when the remote device/user is nearby. For example, the user might use the remote device to request identification of alcohol wipes. The remote device may contact server 114, which in turn may query inventory tracking 115 to find a bin or tote containing alcohol wipes that is closest to the user. For example, the position of the user may be detected using GPS, or triangulated based on the proximity of hub 190B to the remote device. Inventory tracking 115 may identify alcohol wipes as being within the bins associated with interactive storage devices 130D and 130G, and may therefore identify interactive inventory storage device 130G as being associated with the closest bin or tote to the user. As a result, server 114 may instruct interactive inventory storage device 130G to enter into an alert or identification mode, wherein a LED flashes a specific color (e.g., white) to guide the user to the bin or tote that contains alcohol wipes. In some implementations, the specific color may be selected based on the user requesting the item. For example, multiple clinicians may be retrieving items from the same storage room including two or more bins with respective interactive storage devices. By guiding a user based on a color assigned to the specific user, each clinician may conduct a retrieval at the same time without confusion or taking the wrong item. The color may also consider specific clinician profile characteristics such as color blindness. Colorblind clinicians may not discern certain colors. For such clinicians, the system may active the interactive inventory storage device 130D to present a color that can be differentially observed by the clinician.

As shown in system 200, each interactive inventory storage device 130A-130G may connect to network 118 using one of hub 190A or 190B, which may have an infrastructure or cellular connection to network 118. Since the bins and the attached interactive storage devices 130A-130G may be moveable from one room to another, the interactive storage devices 130A-130G may potentially lose connection to hubs 190A and 190B. For example, interactive storage devices 130C and 130D may be located too far away to connect to hub 190A or 190B. In this case, interactive storage devices 130A-130G may provide mobile mesh network 119, wherein each interactive inventory storage device 130A-130G may function as a mesh node hop to facilitate a connection to hub 190A and 190B. When a route to server 114 is not immediately available, then an interactive storage device may operate in an offline mode wherein inventory management is handled locally until a synchronization can occur with server 114 when a connection route is available.

In some implementations, each interactive storage device may also track the location and inventory of other nodes in a local cache. In this manner, interactive storage devices 130A-130G may query mobile mesh network 119 for the location of an item, instead of relying on server 114. Thus, each node in mobile mesh network 119 may periodically broadcast and propagate their own position and inventory to all other nodes, allowing a local cache of node locations and inventory to be stored by each node. In this manner, each node can quickly determine, from the local cache, the closest node where the requested item is possibly present. Since the local cache may be potentially out of date, a node may verify whether the requested item is actually still present by using mobile mesh network 119 to send a query to the closest node. Once the closest node is determined, then a location of the closest node may be displayed on a map, e.g. on display 165 or on a display of a remote device. If the requested item is not present, then the node may respond by providing the last authorized user and access time, if available.

In this manner, devices connected to mobile mesh network 119 may cooperatively determine that the requested item is contained within a bin or tote associated with a particular interactive storage device. As a result, server 114 may instruct the identified interactive storage device to enter into an alert or identification mode, wherein a LED flashes white to guide the user to the interactive storage device. The remote device may also display a map to guide the user to the interactive storage device. Further, any smart devices between the user and the destination may be directed to illuminate a path.

At server 114, inventory tracking 115, item condition tracking 116, and machine learning 117 may be queried and updated according to status information provided by each interactive storage device. For example, inventory tracking 115, item condition tracking 116, and machine learning 117 may track the location, quantity, and condition of various medicines and healthcare items inside bins attached to interactive storage devices 130A-130G. Inventory tracking 115 may be updated to reflect items added or removed from bins. Item condition tracking 116 may be updated according to changing environmental conditions experienced by each interactive storage device. Machine learning 117 may record device interactions and usage data for each interactive inventory storage device 130A-130G. Referring to FIG. 1A, the information stored in server 114 may be synchronized from data logs retrieved from non-volatile data store 137.

At least a portion of the interactive storage device usage data may be processed by one or more machine learning algorithms to determine a power management profile that can be pushed back to interactive storage devices 130A-130G for optimized power consumption. For example, the power management profile may define daily time periods when user interactions are infrequent. Interactive storage devices 130A-130G may use this profile to transition the processor and other components to a low power idle or sleep mode during these daily time periods.

Each interactive storage device may also support real-time status reporting when a network connection route is available. For example, a client may query server 114 for the status of a specific interactive storage device. Assuming that server 114 can establish a network route to communicate with the requested interactive storage device, the interactive storage device may be queried for the requested status, such as environmental condition, location history, or local inventory status, and the interactive storage device may respond by sending an encrypted message containing the requested status.

After arrival at a destination such as patient room 211, the interactive storage devices 130A and 130B may be organized onto shelves and remain largely stationary until a restock is necessary. Since the interactive storage devices 130A and 130B have a built in display 165 as shown in FIG. 1B, the display may continuously show both an item description and a quantity of items contained in an associated bin. Referring to FIG. 1A, by using a low power display technology such as e-ink for display interface 164, battery life of power source 180 may be extended. Accordingly, a user can quickly identify the contents of each bin or tote at a glance without actually pulling out the bin or tote and looking closely at the contents. Further, the stock level and battery level of each bin or tote may be readily perceived and blinking LEDs or other audiovisual alerts may further bring attention to low stock, low battery levels, or item condition deterioration, allowing remedial action to be carried out early before problems arise. Accordingly, items can be kept well stocked and functional for smooth operation of hospital 110.

When multiple bins are stacked or arranged together or behind each other, then the multiple bins may be leveraged to help identify a target bin. For example, as discussed above, the user may request the location of a particular item to be identified. Once a target bin or tote having the particular item is identified, multiple interactive storage devices on multiple bins may be used to provide a visible path to the target bin or tote with the requested item. The bins along the path may use a different light blinking pattern or color to distinguish themselves from the target bin.

Figure 2A:
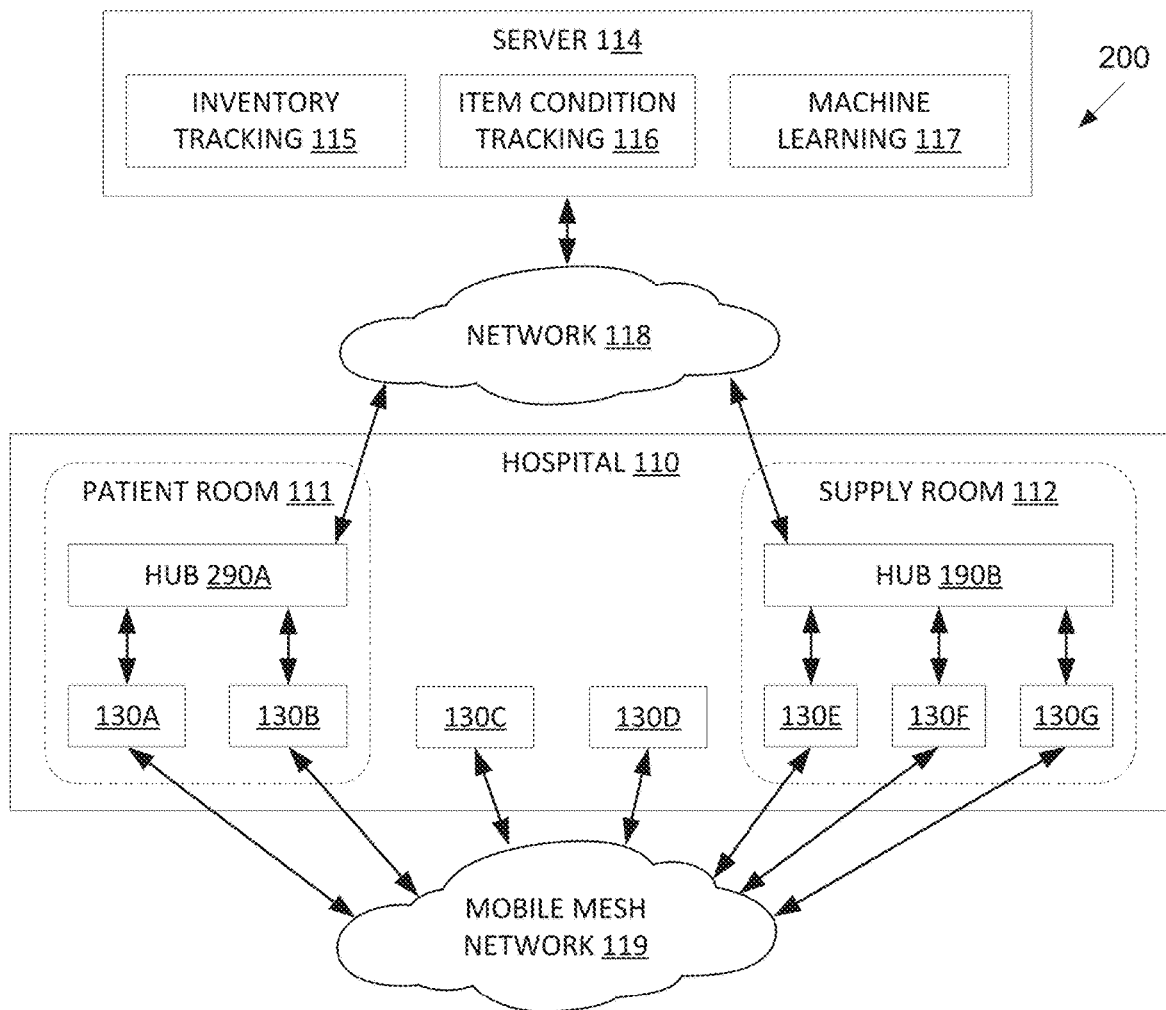
FIG. 2A depicts an example system including interactive connected inventory devices in an example network to provide automated inventory management, according to various aspects of the subject technology.
Figure 2B:
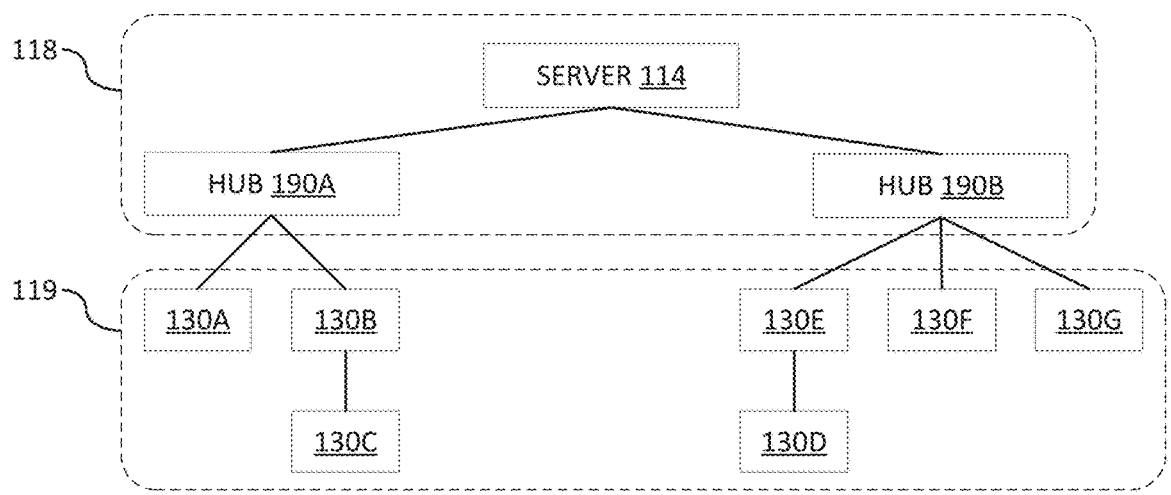
FIG. 2B depicts an example network topology diagram of the interactive connected inventory devices from FIG. 2A, according to various aspects of the subject technology.

FIG. 2B depicts an example network topology diagram of interactive storage devices 190A-190G from FIG. 2A, according to various aspects of the subject technology. Network 118 may correspond to a public network such as the Internet, and server 114 may be connected to hub 190A and 190B. Mobile mesh network 119 may correspond to an ad-hoc mobile mesh network, wherein each individual node, or interactive storage devices 130A-130G may physically move and disconnect and reconnect with each other according to radio reception to form a mesh network. Interactive storage devices 130A-130B may connect directly to hub 190A, whereas interactive inventory storage device 130C may connect to hub 190A using interactive inventory storage device 130B as an intermediary node. Similarly, interactive storage devices 130E-130G may connect directly to hub 290B, whereas interactive inventory storage device 130D may connect to hub 190B using interactive inventory storage device 130E as an intermediary node. Thus, nodes can act as master nodes (e.g. server 114), slave nodes (e.g. interactive storage devices 130A, 130C, 130D, 130F, and 130G), or hybrid master/slave nodes (e.g. interactive storage devices 130B, 130E and hub 190A, 190B).

FIG. 3 depicts various example user interfaces of an interactive storage device, according to various aspects of the subject technology. With respect to FIG. 3, display 365A, display 365B, and display 365C may correspond to display 165 from FIG. 1B. In some implementations, display 365A-365C may be shown on a remote device, such as a tablet, smartphone, laptop, or desktop computer.

Display 365A shows a status screen, which may be shown by default when no user interaction is taking place. As shown in display 365A, the status screen may include several informational fields, such as a description of the bin or tote contents, a quantity, a battery level, a network status, and user interface instructions for using take button 161A and receive button 161B of FIG. 1A and FIG. 1B. Referring to FIG. 1A, the description and quantity may be updated according to a local inventory stored in non-volatile data store 137. The battery level may be updated according to estimated charge detected for power source 180. Network status may be updated according to the availability of connectable networks via communication interface 140. The user interface instructions may change depending on the user interface context. While display 365A-365C illustrate text representations, it should be understood that graphical representations such as icons, bars, charts, animations, and other elements may be shown.

As shown in display 365A, the user may press take button 161A to decrement or subtract the quantity by one, thereby changing the quantity from 100 to 99. Alternatively, the user may press receive button 161B to increment or add the quantity by one, thereby changing the quantity from 100 to 101.

Display 365B shows a management mode screen, which may be shown after an authenticated user login. For example, as discussed previously, an IAM interface may be used to verify the identity of a user. In the management mode, the user can select from a number of menu options, with take button 161A cycling through menu items and receive button 161B selecting or exiting from menus depending on the length of the press. As shown in display 365B, the user may change the item associated with the bin, set the quantity of items, adjust power management settings, and review data logs, such as sensor data history. Of course, these menu items are exemplary and other menu items may be presented to the user.

Display 365C shows a restock mode screen, which may be shown based on proximity to stock rooms or warehouses. For example, referring to FIG. 2A, if a connection to hub 290B is available, then an interactive storage device may assume a location within supply room 212 and may automatically switch to a restock mode. As shown in display 365C, the restock mode allows the user to rapidly set the quantity to a specific number on a per-digit basis, rather than incrementing and decrementing the quantity one by one as in the normal mode shown in display 365A. For example, take button 161A may cycle between digit positions, with the hundreds digit currently selected in display 365C, and receive button 161B may cycle between values, for example incrementing value 1 to 2, 3, 4, 5, 6, 7, 8, 9, and returning to 0. In some implementations, a preset quantity may be set for each type of item, such as 100 for alcohol wipes.

Figure 4:
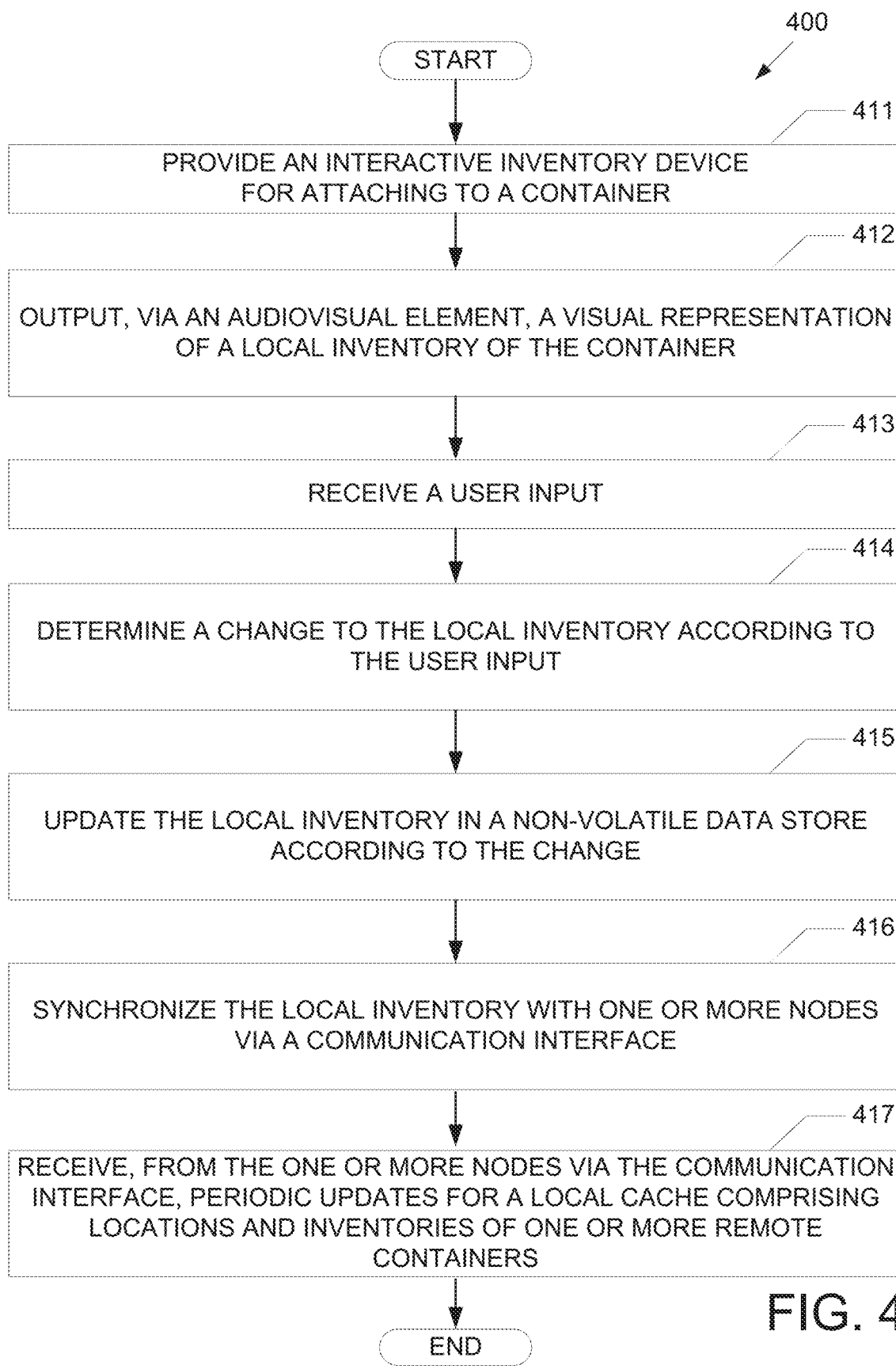
FIG. 4 depicts an example process including an interactive connected inventory device to provide automated inventory management, according to various aspects of the subject technology.

FIG. 4 depicts an example process 400 for using an interactive storage device to provide automatic inventory management, according to various aspects of the subject technology. For explanatory purposes, the various blocks of example process 400 are described herein with reference to FIGS. 1A-3, and the components and/or processes described herein. The one or more of the blocks of process 400 may be implemented, for example, by a computing device, including a processor and other components utilized by the device. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, an interactive storage device is provided for attaching to a container (411). Referring to FIG. 1E, this may correspond to providing interactive inventory storage device 130 for attaching to bin or tote 120. More specifically, referring to FIG. 1C and FIG. 1D, clip recess 131 of interactive inventory storage device 130 may slide into retainer slot 121 of a container such as bin or tote 120.

Process 400 may continue with outputting, via an audiovisual element, a visual representation of a local inventory of a container such as bin or tote 120 (412). For example, referring to FIG. 1A, processor 134 may retrieve the local inventory from non-volatile data store 137, and utilize display interface 164 to output a user interface to an e-ink display, wherein the user interface may include text and/or graphics. For example, referring to FIG. 3, the user interface may appear similar to display 365A. As shown in display 365A, the visual representation includes a description of the bin or tote contents, or "Alcohol Wipes", and a quantity of 100, which may be indicated by the local inventory.

Processor 134 may continue to receive a user input (413). For example, referring to FIG. 1B, the user may press take button 161A or receive button 161B to add or remove inventory, respectively. In some implementations, each item in bin or tote 120 may include a RFID tag or similar tracker. Processor 134 may utilize communication interface 140 or sensors 150 to detect the presence or absence of RFID tags. When the user places a new item into bin or tote 120 or removes an item from bin or tote 120, the addition or removal of the item with the RFID tag may be detected as the user input.

Processor 134 may continue to determine a change to the local inventory according to the user input (414). For example, take button 161A may correspond to decrementing, or subtracting the quantity of an item in the local inventory by one, whereas receive button 161B may correspond to incrementing, or adding the quantity of an item in the local inventory by one. Similarly, a user input of removing an item with a RFID tag may correspond to decrementing, whereas a user input of adding an item with a RFID tag may correspond to incrementing. In some implementations, the processor 134 may be communicatively coupled with a sensor that provides a measurement for use in determining the change in local inventory. For example, a weight sensor may be provided in the bin. Based on the expected inventory, a theoretical weight may be generated and compared with the actual measured weight. If the theoretical weight after the expected inventory change corresponds to the actual weight, then the determination may be confirmed. If the determination is not confirmed, the processor 134 may generate an alert message. The alert message may be displayed via the inventory device or transmitted for presentation via another device.

Processor 134 may continue to update the local inventory in a non-volatile data store according to a change (415). For example, based on the determined change of incrementing or decrementing, the local inventory stored in non-volatile data store 137 may be updated with correspondingly increased or decreased quantities.

Processor 134 may continue to synchronize the local inventory with one or more nodes via a communication interface (416). For example, referring to FIG. 1A, FIG. 2A and FIG. 2B, processor 134 may synchronize the local inventory stored in non-volatile data store 137 with other nodes on mobile mesh network 219 via communication interface 140. In this manner, other nodes on mobile mesh network 219 may update their own local caches with the updated local inventory. Processor 134 may also synchronize the local inventory with inventory tracking 215 stored on server 214. In some cases, this synchronization may be deferred until a stable network route to server 214 is available, as the interactive storage device may be mobile and network connectivity may vary depending on location. As discussed above, the interactive storage device may form mobile mesh network 219 with other interactive storage devices to improve network availability. The current location of the interactive storage device may also be conveyed to server 214 based on triangulation using hubs 290A-290B or other location tracking methods.

In this manner, inventory tracking 215 can be automatically updated with the current location, item type, and item quantities for each bin or tote equipped with an interactive storage device, enabling detailed insight into current inventory levels for medical supply restocking, loss prevention, and other management tasks. Similarly, item condition tracking 216 may be updated to track the environmental condition and item quality of each container, and machine learning 217 may be updated with interactive storage device usage statistics to provide training data for power management profile generation.

Processor 134 may continue to receive, from the one or more nodes via the communication interface, periodic updates for a local cache comprising locations and inventories of one or more remote containers (417). For example, referring to FIG. 1A, FIG. 2A and FIG. 2B, processor 134 may receive periodic updates from nodes in mobile mesh network 219, wherein the updates include locations and inventories of remote containers. In this manner, processor 134 may update a local cache in non-volatile data store 137 to keep a current map of bins and associated inventory, which can then be used to respond to item location requests. As discussed above, processor 134 may verify whether an identified node actually contains a requested item before providing a response, such as displaying a map to the identified node.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
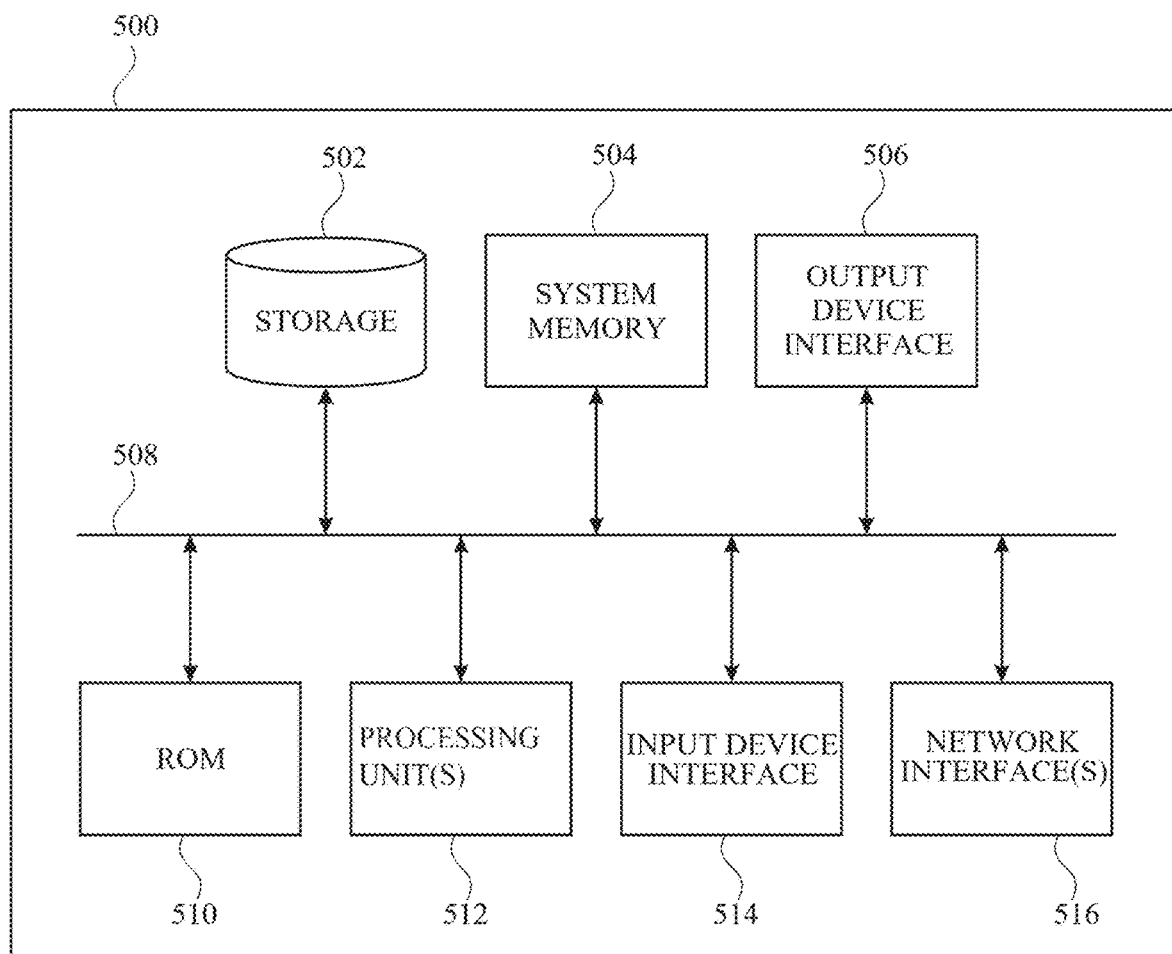
FIG. 5 is a conceptual diagram illustrating an example electronic system 500 for implementation of an interactive inventory storage device and automated inventory management, according to various aspects of the subject technology.

FIG. 5 is a conceptual diagram illustrating an example electronic system 500 for implementation of an interactive inventory storage device and automated inventory management, according to various aspects of the subject technology. The system may further be implemented for secure storage, transport, and dispensing of items with automatic inventory, item condition, chain of custody tracking, and the like. Electronic system 500 may be a computing device for execution of software associated with one or more portions or steps of process 400, or components and processes provided by FIGS. 1A-4. Electronic system 500 may be representative, in combination with the disclosure regarding FIGS. 1A-4, of the interactive inventory storage device 130 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Some implementations use a removeable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

As will be described further, the disclosed systems and methods provide integrated, enterprise grade, end-to-end solution to address the numerous requirements of medicine and healthcare item dispensing in clinical settings. A method includes providing a smart tote controller for attaching to a tote. The method also includes receiving user credentials for accessing the tote. The method also includes validating the user credentials for accessing the tote. The method also includes triggering an actuator to open a lock, thereby allowing a lid of the tote to be opened. The method also includes determining a change in contents of the tote. The method also includes updating, in a non-volatile data store, an inventory according to the change in contents. The method also includes triggering the actuator to close the lock after detecting the lid is closed. The method also includes recording the user credentials, one or more timestamps, and the change in contents in an access log.

Figure 6A:
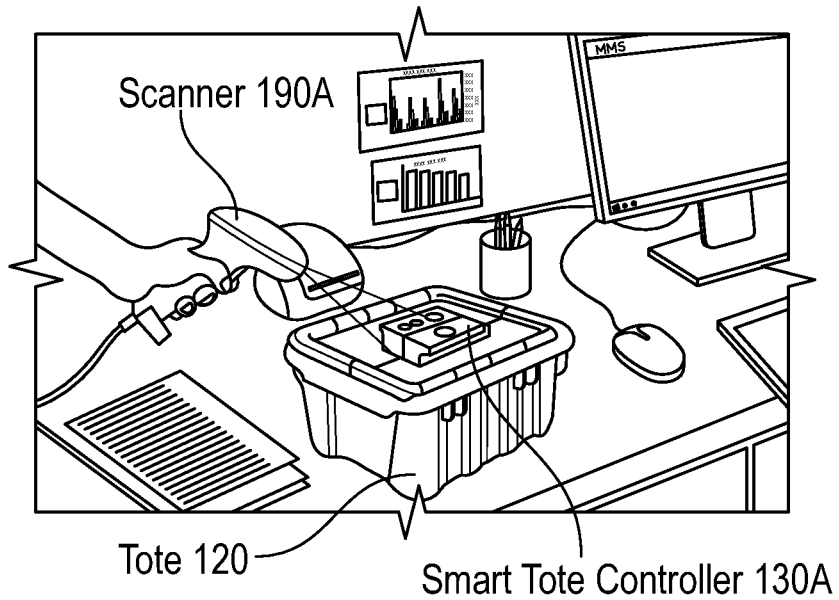
FIGS. 6A and 6B depict perspective views of an example smart tote controller attached to an example tote and interfacing with example scanner devices, according to various aspects of the subject technology.
Figure 6B:
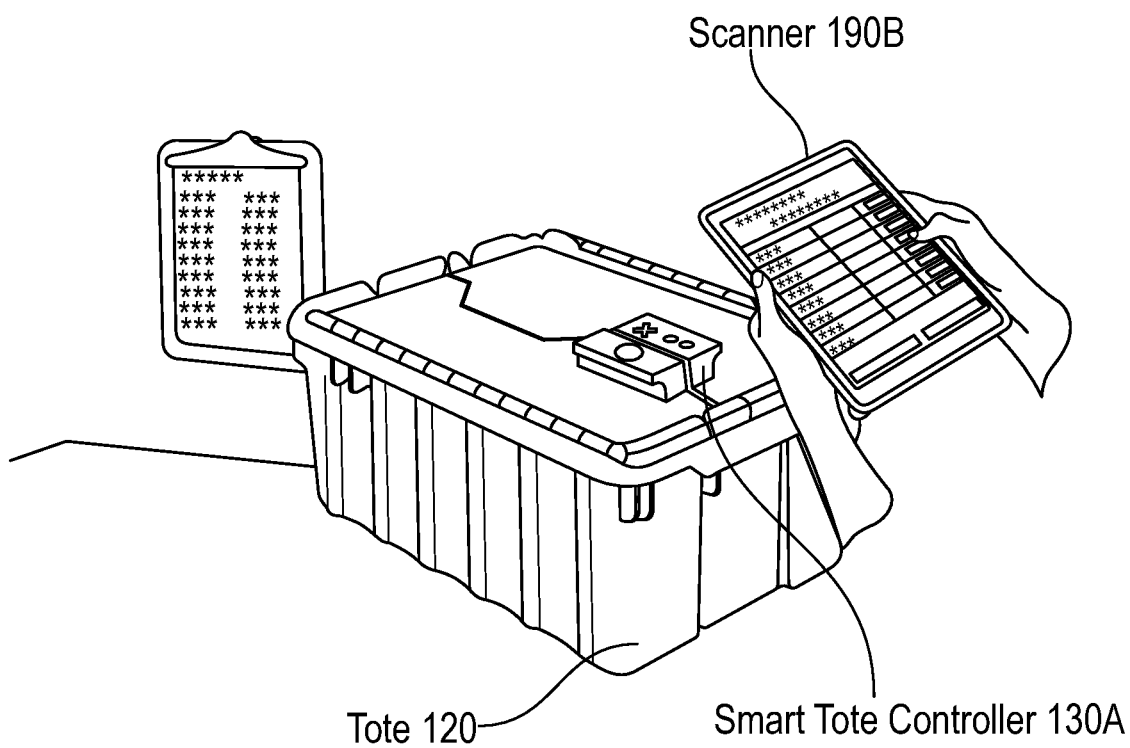

FIGS. 6A and 6B depict perspective views of a smart tote controller 130A attached to tote 120 and interfacing with respective scanner 190A and scanner 190B, according to various aspects of the subject technology. As shown in the depicted examples, smart tote controller 130A can be readily attached to a lid of an existing tote 120, for example by using screws, strong adhesives, or other permanent attachment methods. Smart tote controller 130A may be provided as two halves that are attached to each lid half of tote 120, and a lock (not shown) that secures the two halves may be locked to secure the lid or unlocked to allow the lid to be opened.

Scanner 190A may correspond to an optical scanner that can read 1D or 2D barcodes and/or LED flashing patterns to receive data from smart tote controller 130A. Scanner 190A may be connected to a computing device, such as a tablet, smartphone, desktop, or laptop computer. Scanner 190A may be used, for example, to prepare a tote for shipment by using scanner 190A to identify smart tote controller 130A for loading medications into tote 120. For example, smart tote controller 130A may include an embedded unique identifier or serial number that can be transmitted using barcodes or LEDs. The remote device connected to scanner 190A may contact a remote server, e.g. a pharmacy server, to determine, for example, a list of medications to be added tote 120, which may be associated with a specific patient and/or healthcare provider. After a user is authenticated by smart tote controller 130A, the correct medications may be selected and added into tote 120. Pharmacy and tote inventories may also be automatically updated according to the expected change in contents of tote 120. In some implementations, the totes may be preloaded with medications, and the user only needs to identify the correct tote from a collection of totes. For example, as discussed above, LED lights may blink on a specific tote to identify the tote to the user. A similar process may be used for dispensing medications from smart totes at a receiving facility, such as a hospital or clinic.

Scanner 190B may correspond to a computing device with communications capability, such as the tablet shown in FIG. 6B. However, scanner 190B could also comprise a smartphone, a laptop computer, a desktop computer, or another device. Scanner 190B may execute a local application downloaded from an application store, a corporate network, a website, or another distribution method. Alternatively, scanner 190B may execute a remote cloud-based application or a Software as a Service (SaaS) application. The application may allow scanner 190B to communicate with smart tote controllers such as smart tote controller 130A. For example, the application may utilize radios of scanner 190B that support various protocols such as Bluetooth, Bluetooth Low Energy, Near Field Communication (NFC), Wi-Fi, contactless smartcards, Radio-Frequency identification, and others. Accordingly, scanner 190B may communicate with smart tote controller 130A and interact with smart tote controller 130A in a similar manner as described above with scanner 190A.

Further, if scanner 190A and 190B are connected to a network, such as via a Wi-Fi or cellular connection, smart tote controller 130A may utilize the network to communicate and synchronize with a remote server, as described in further detail below in conjunction with FIG. 7A and FIG. 7B. Alternatively, when such a connection is not present, smart tote controller 130A may utilize mobile mesh networking to use other smart tote controllers as nodes to connect to the remote server. In some implementations, a cellular modem may be included within smart tote controller 130A to provide a direct cellular connection to the remote server. However, to reduce implementation complexity and data network costs, it may be preferable to omit a cellular modem.

While smart tote controller 130A allows for quick and easy attachment to tote 120, the combination may not be ideal for a few reasons. For example, since smart tote controller 130A protrudes above the lid surface of tote 120, it becomes difficult to stack multiple totes together for efficient use of space. Further, since side portions of smart tote controller 130A are highly accessible, it becomes difficult to provide strong tamper protection and to prevent unauthorized entry.

Figure 6C:
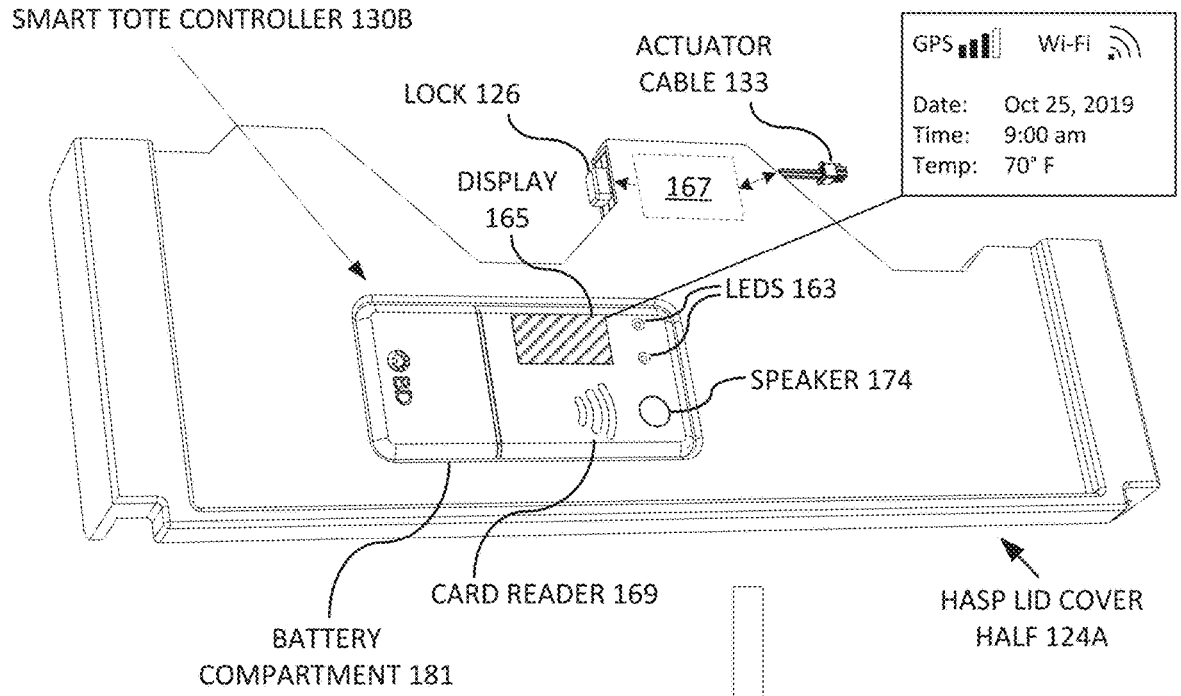
FIG. 6C depicts a perspective view of another example smart tote controller integrated into a hasp lid cover half, according to various aspects of the subject technology.
Figure 6D:
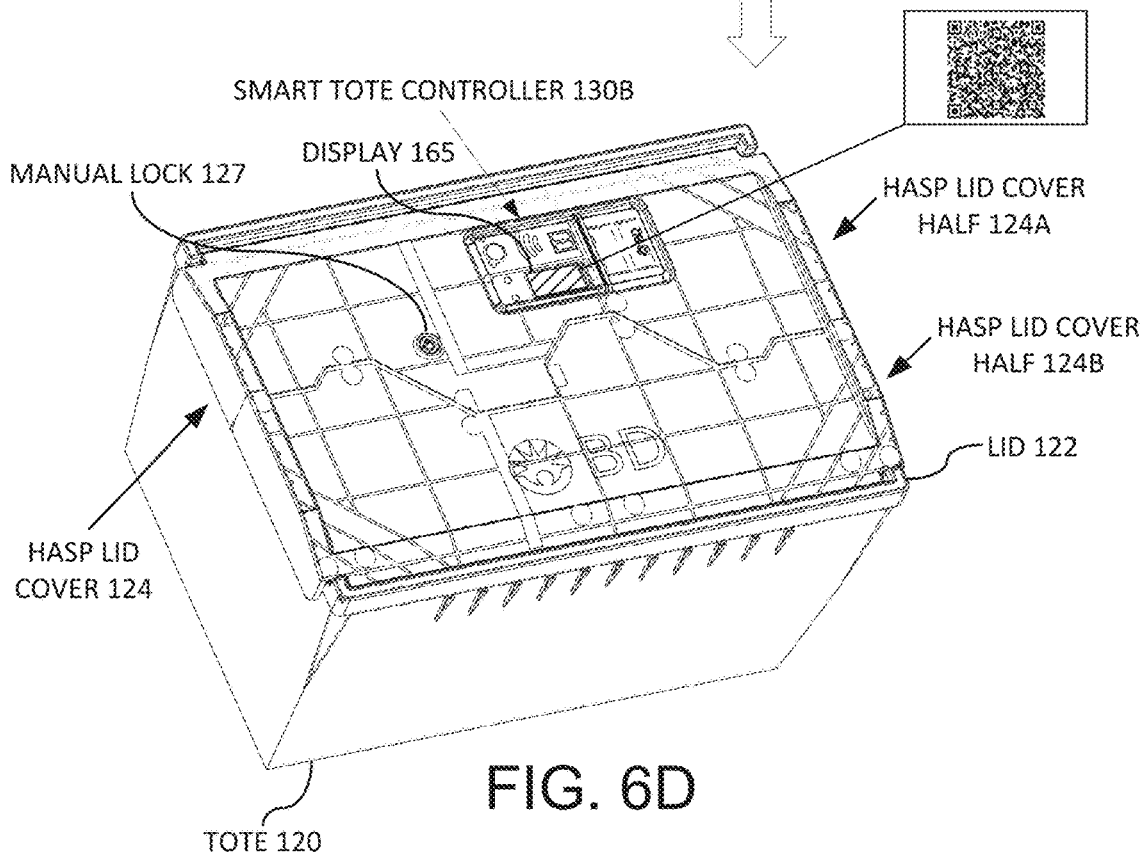
FIG. 6D depicts a perspective view of the hasp lid cover half from FIG. 6C attached to a lid of an example tote, according to various aspects of the subject technology.

FIG. 6C and FIG. 6D depict smart tote controller 130B recessed into hasp lid cover 124 attached to lid 122 of tote 120, providing a more robust form factor for enhanced tamper resistance and tote stacking. FIG. 6C depicts a perspective view of smart tote controller 130B integrated into hasp lid cover half 124A, according to various aspects of the subject technology. hasp lid cover half 124A includes lock 126, smart tote controller 130B, actuator cable 133, and actuator 167. Smart tote controller 130b includes LEDs 163, display 165, card reader 169, speaker 174, and battery compartment 181.

Display 165 may, by default, output a status screen similar to that shown in FIG. 6C. As shown in FIG. 6C, the status screen may include GPS connectivity, wireless network connectivity, date and time, and ambient temperature. In some implementations, the user may be able to display a quick read code for scanning by an external or remote device. The quick read code shown in FIG. 6D may encode various identifiers and parameters for monitoring or securing the contents of the tote. Table 1 describes examples of information that may be encoded for display.

TABLE 1

| Field Name | Description |
| --- | --- |
| Tote_ID | Alphanumeric representation of a unique identifier for the tote |
| Controller_ID | Alphanumeric representation of a unique identifier for the smart tote controller |
| Order_ID | Alphanumeric representation of a unique identifier for the order included in the tote. An order may be associated with one or more items expected to be within the tote |
| Origin_Loc_ID | Alphanumeric representation of an identifier for the originating location of the tote |
| Destination_Loc_ID | Alphanumeric representation of an identifier for the destination location of the tote |
| Alert_Params | Array of field value pairs representing thresholds or ranges for monitoring the condition of the tote. Temp low/hi represent lower and upper bounds for temperatures. If below the low or above the hi, alert is needed. Vibe_low/hi represent lower and upper bounds for vibrations or shocks. If below the low or above the hi, alert is needed. Humidity_low/hi represent lower and upper bounds for humidity. If below the low or above the hi, alert is needed. Loc_proximity represents an acceptable range from a destination or origin. If the distance to destination or origin exceeds the proximity, alert is needed. |

Lock 126 and actuator 167 may be embedded within hasp lid cover half 124A. Referring to FIG. 1, actuator interface 166 may connect to actuator cable 133 to actuate lock 126 via actuator 167, which changes lock state 128 from locked to unlocked and vice versa. For example, a bolt of lock 126 may extend into or retract from a lock compartment of hasp lid cover half 124B.

Referring to FIG. 1, various interfaces may drive or control the components of smart tote controller 130B. For example, LED interface 162 may drive LEDs 163, which may display light of varying intensity, colors, and flashing patterns, as previously described. Display interface 164 may drive display 165, which may display status messages and various user interfaces for managing interactive inventory storage device 130 and the contents of tote 120. IAM interface 168 may connect to card reader 169 to read user credentials stored on a contactless smartcard. Audio interface 170 may connect to speaker 174 to output tones to convey information, guidance, warnings, and alerts. Battery compartment 181 may contain power source 180 and may be user accessible for easy replacement of power source 180. The specific elements shown in smart tote controller 130B are exemplary and any configuration of elements may be utilized according to use case requirements.

FIG. 6D depicts a perspective view of hasp lid cover half 124A from FIG. 6C attached to lid 122 of tote 120, according to various aspects of the subject technology. hasp lid cover 124 includes hasp lid cover half 124A and hasp lid cover half 124B. hasp lid cover half 124A includes manual lock 127 and smart tote controller 130B.

Smart tote controller 130B is disposed within an upper recess of hasp lid cover 124 such that a top surface of hasp lid cover 124 is substantially flush with smart tote controller 130B. In this manner, multiple totes can be easily stacked on top of each other, as shown in conjunction with FIG. 8F below. Further, since smart tote controller 130B is recessed within hasp lid cover 124, it becomes more difficult to tamper with or attempt removal of smart tote controller 130B. As discussed above, if power source 180 is exhausted, lock 126 may remain in the locked or unlocked state until power is restored, for example by the user exchanging power source 180 via battery compartment 181. Alternatively, a master key may be used to engage manual lock 127, which may be connected to lock 126. While not specifically shown in FIG. 6C and FIG. 6D, wired or wireless power harvesting may also be used to recharge power source 180 without opening battery compartment 181.

Figure 7A:
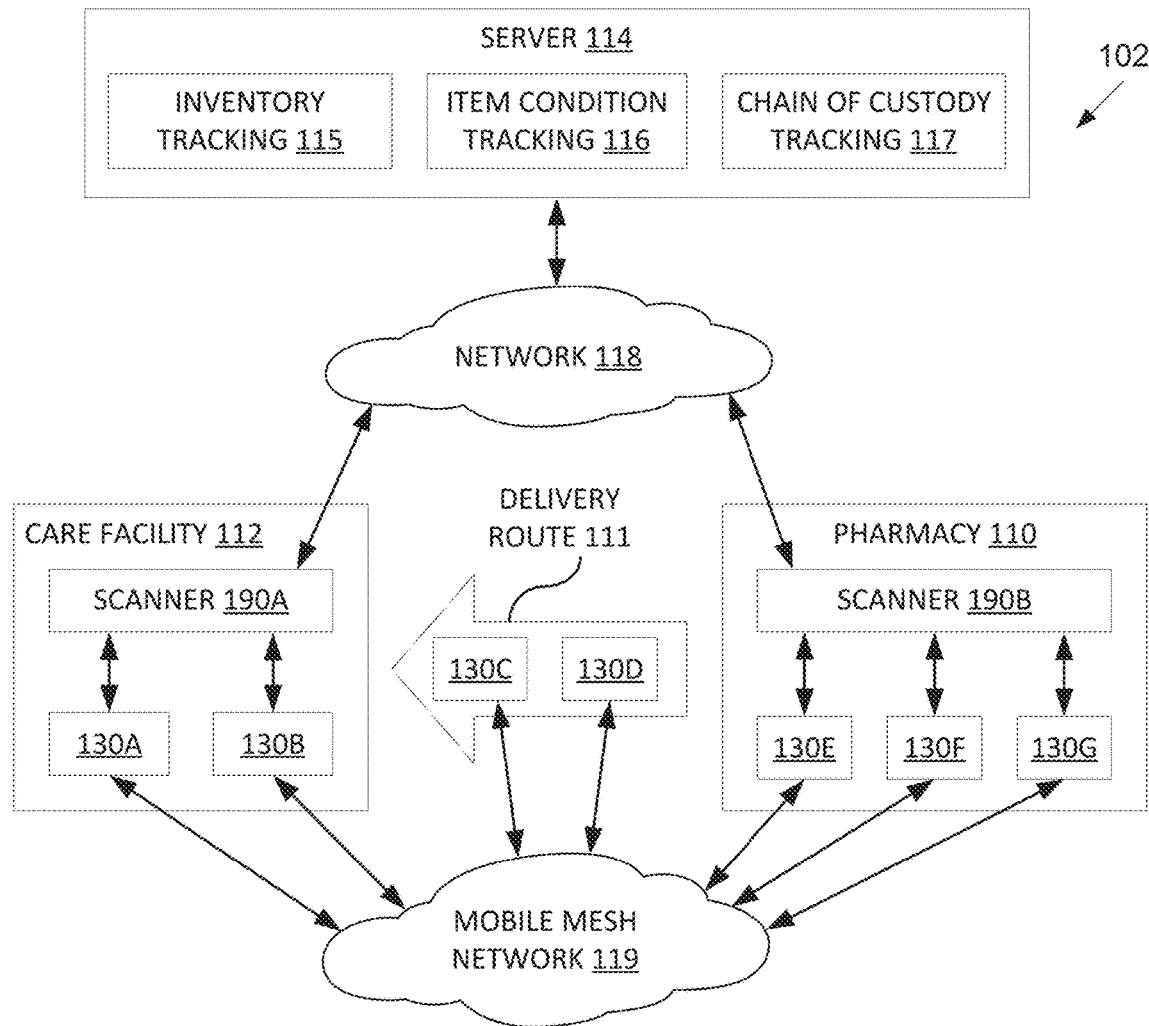
FIG. 7A depicts an example system using smart tote controllers in an example network to provide secure storage, transport, and dispensing of items with automatic inventory, item condition, and chain of custody tracking, according to various aspects of the subject technology.
Figure 7B:
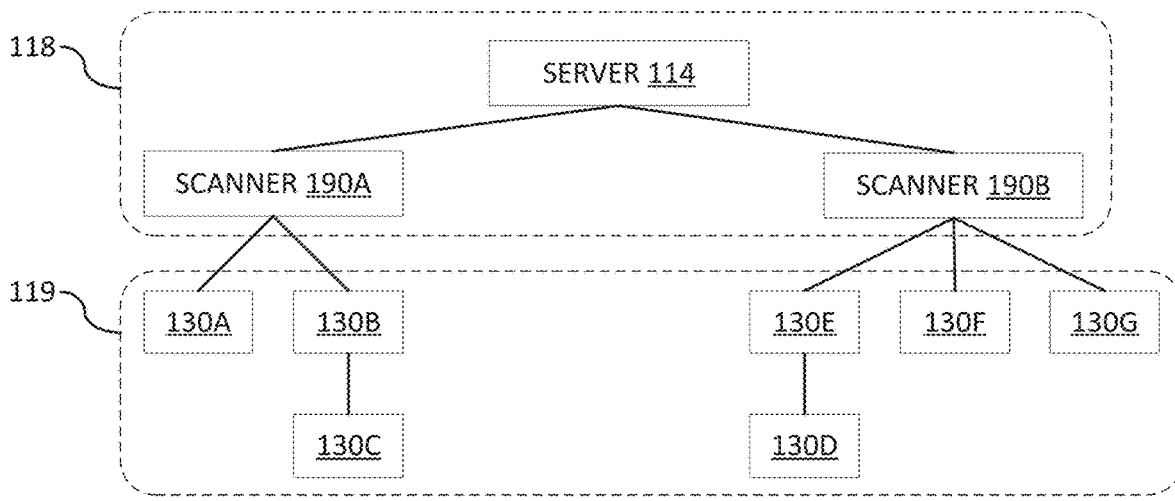
FIG. 7B depicts an example network topology diagram of the smart tote controllers from FIG. 7A, according to various aspects of the subject technology.

FIGS. 7A and 7B depict a variation of the network configurations of FIGS. 2A and 2B, with a configuration for a smart tote controller system. FIG. 7A depicts system 102 using smart tote controllers 130A through 130G in networks 118 and 119 to provide secure storage, transport, and dispensing of items with inventory tracking 115, item condition tracking 116, and chain of custody tracking 117, according to various aspects of the subject technology. FIG. 7A includes pharmacy 110, delivery route 111, care facility 112, server 114, network 118, and mobile mesh network 119. Pharmacy 110 includes smart tote controller 130E, smart tote controller 130F, smart tote controller 130G, and scanner 190B. Delivery route 111 includes smart tote controller 130C and smart tote controller 130D. Care facility 112 includes smart tote controller 130A, smart tote controller 130B, and scanner 190A. Server 114 includes inventory tracking 115, item condition tracking 116, and chain of custody tracking 117. For simplicity of discussion, each smart tote controller may be attached to a corresponding tote, which is not specifically shown.

For example, starting at pharmacy 110, a user may utilize scanner 190B to identify and load totes associated with smart tote controllers 130E, 130F, and 130G with medicines or other healthcare items for associated patients. To authenticate a user and identify the specific totes to load and the medicines to load into each tote, smart tote controllers 130E-130G may utilize scanner 190B to connect to server 114 via network 118. Scanner 190B may be connected to an infrastructure network of pharmacy 110 having access to a public network, such as network 118, which may comprise the Internet. In some implementations, a cellular router, hub, gateway, modem, or another network device may be provided to connect the smart tote controllers to network 118, allowing the smart tote controllers to be immediately deployed without requiring potentially costly and time consuming integration into existing information technology (IT) infrastructure at pharmacy 110.

If a direct connection to scanner 190B is not available, for example due to a weak transmission signal, then mobile mesh network 119 may be utilized to reach scanner 190B via one or more node hops using other smart tote controllers. If a route to server 114 is not immediately available, then a smart tote controller may operate in an offline mode wherein user authentication and inventory management is handled locally until a synchronization can occur with server 114 when a connection route is available.

Once a connection with server 114 is established, inventory tracking 115, item condition tracking 116, and chain of custody tracking 117 may be queried and updated according to status information provided by each smart tote controller. For example, inventory tracking 115, item condition tracking 116, and chain of custody tracking 117 may track the location, quantity, condition, and chain of custody for various medicines and healthcare items inside or outside smart totes at various clinical settings and transport routes. Inventory tracking 115 may be updated to reflect items from pharmacy 110 being removed and placed into an associated smart tote. Item condition tracking 116 may be updated according to changing environmental conditions experienced by each smart tote. Chain of custody tracking 117 may record the authorized user who placed the items into the associated smart tote and one or more associated timestamps, for example when the user credentials were provided, when a lock was unlocked, and when the lock was locked. Referring to FIG. 1, the information stored in server 114 may be synchronized from data logs retrieved from non-volatile data store 137.

Each smart tote may also support real-time status reporting when a network connection route is available. For example, a client may query server 114 for the status of a specific smart tote. Assuming that server 114 can establish a network route to communicate with the requested smart tote, the smart tote may be queried for the requested status, such as environmental condition or location history, and the smart tote may respond by sending an encrypted message containing the requested status.

Once a smart tote is ready for shipment, it may be placed on a vehicle or other transportation method along delivery route 111 to care facility 112. For example, smart tote controller 130C and smart tote controller 130D may have been previously sent from pharmacy 110 and are currently en-route to care facility 112 via delivery route 111. As shown in FIG. 7A, smart tote controllers 130C-130D may utilize mobile mesh network 119 to attempt to establish a route to server 114. However, if delivery route 111 is a significant distance, then mobile mesh network 119 may be unable to establish a stable route to network 118. In some implementations, a gateway device to connect to network 118 may be provided within the vehicle, or the driver's mobile device may be used as a hotspot that is connected to network 118 via a cellular network. In this manner, smart totes can establish reliable network connectivity along delivery route 111. This may be useful to provide real-time location tracking of smart totes in transit.

After arrival at the destination, or care facility 112, scanner 190A may be used to identify the contents of each smart tote, such as totes associated with smart tote controller 130A and 130B, thereby directing the user to the associated patient for dispensing and administering the included medications. Alternatively, the smart totes may be collected in a storage area, and the correct smart tote may be identified on demand, for example based on each individual patient's dosage schedule. As discussed above, a specific smart tote may be identified by using a visual indication such as a blinking LED.

FIG. 7B depicts an example network topology diagram of smart tote controllers 190A-190G from FIG. 7A, according to various aspects of the subject technology. Network 118 may correspond to a public network such as the Internet, and server 114 may be connected to scanner 190A and 190B. Mobile mesh network 119 may correspond to an ad-hoc mobile mesh network, wherein each individual node, or smart tote controllers 130A-130G may physically move and disconnect and reconnect with each other according to radio reception to form a mesh network. Smart tote controllers 130A-130B may connect directly to scanner 190A, whereas smart tote controller 130C may connect to scanner 190A using smart tote controller 130B as an intermediary node. Similarly, smart tote controllers 130E-130G may connect directly to scanner 190B, whereas smart tote controller 130D may connect to scanner 190B using smart tote controller 130E as an intermediary node. Thus, nodes can act as master nodes (e.g. server 114), slave nodes (e.g. smart tote controllers 130A, 130C, 130D, 130F, and 130G), or hybrid master/slave nodes (e.g. smart tote controllers 130B, 130E and scanner 190A, 190B).

Figure 8A:
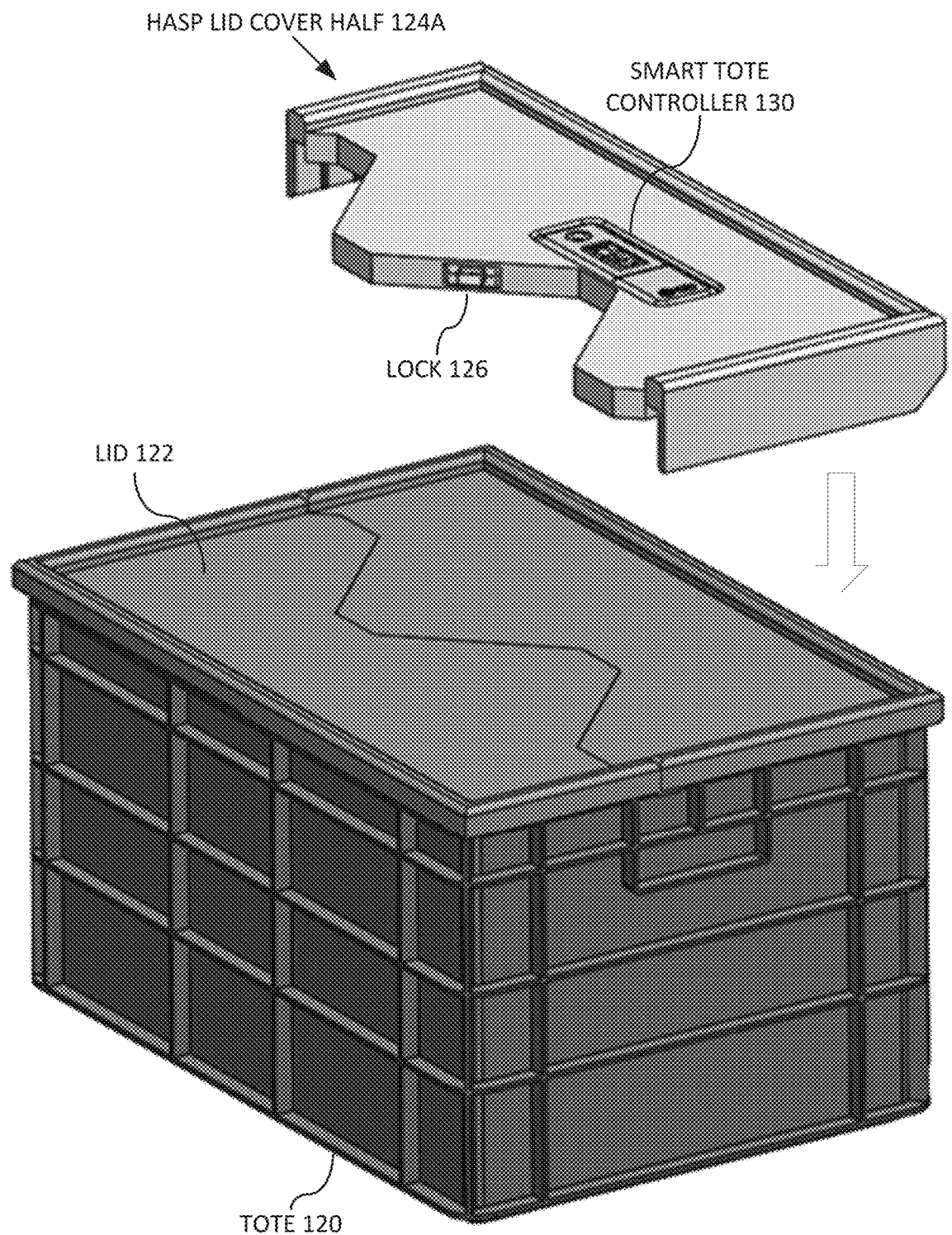
FIG. 8A depicts a perspective view of a smart tote controller integrated into a first half of a hasp lid for attaching to a lid of a tote, according to various aspects of the subject technology.

With an overview of networked smart tote controllers now in place, it may be helpful to examine various perspective views of a hasp lid with an integrated smart tote controller to demonstrate the tamper resistant and space saving properties of the hasp lid. FIG. 8A depicts a perspective view of smart tote controller 130 integrated into hasp lid cover half 124A for attaching to lid 122 of tote 120, according to various aspects of the subject technology. hasp lid cover half 124A includes lock 126. With respect to FIGS. 8A-8F, like numbered elements may correspond to similar elements from FIGS. 6A-6D.

As shown in FIG. 8A, hasp lid cover half 124A may have extended side panels that extend below the lip of existing lid 122. These side panels may provide greater tamper resistance by preventing attempts to pry lid 122 off tote 120. In some implementations, lid 122 may also be provided with extended side panels as well.

Figure 8B:
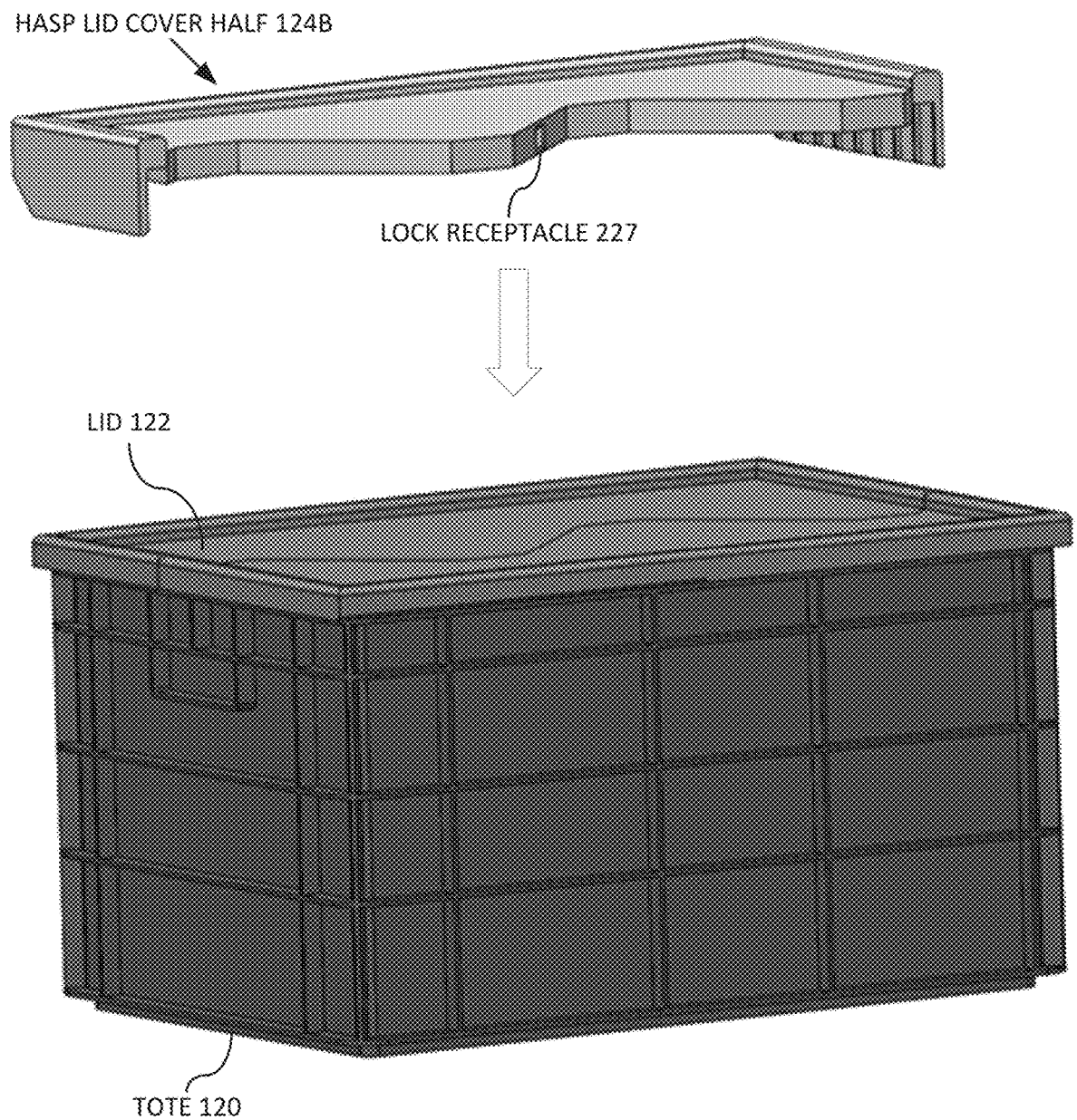
FIG. 8B depicts a perspective view of a second half of a hasp lid for attaching to a lid of a tote, according to various aspects of the subject technology.

FIG. 8B depicts a perspective view of a hasp lid cover half 124B for attaching to lid 122 of tote 120, according to various aspects of the subject technology. hasp lid cover half 124B includes lock receptacle 127, which may receive lock 126 from FIG. 8A. As shown in FIG. 8B, hasp lid cover half 124B also includes extended side panels for tamper resistance.

Figure 8C:
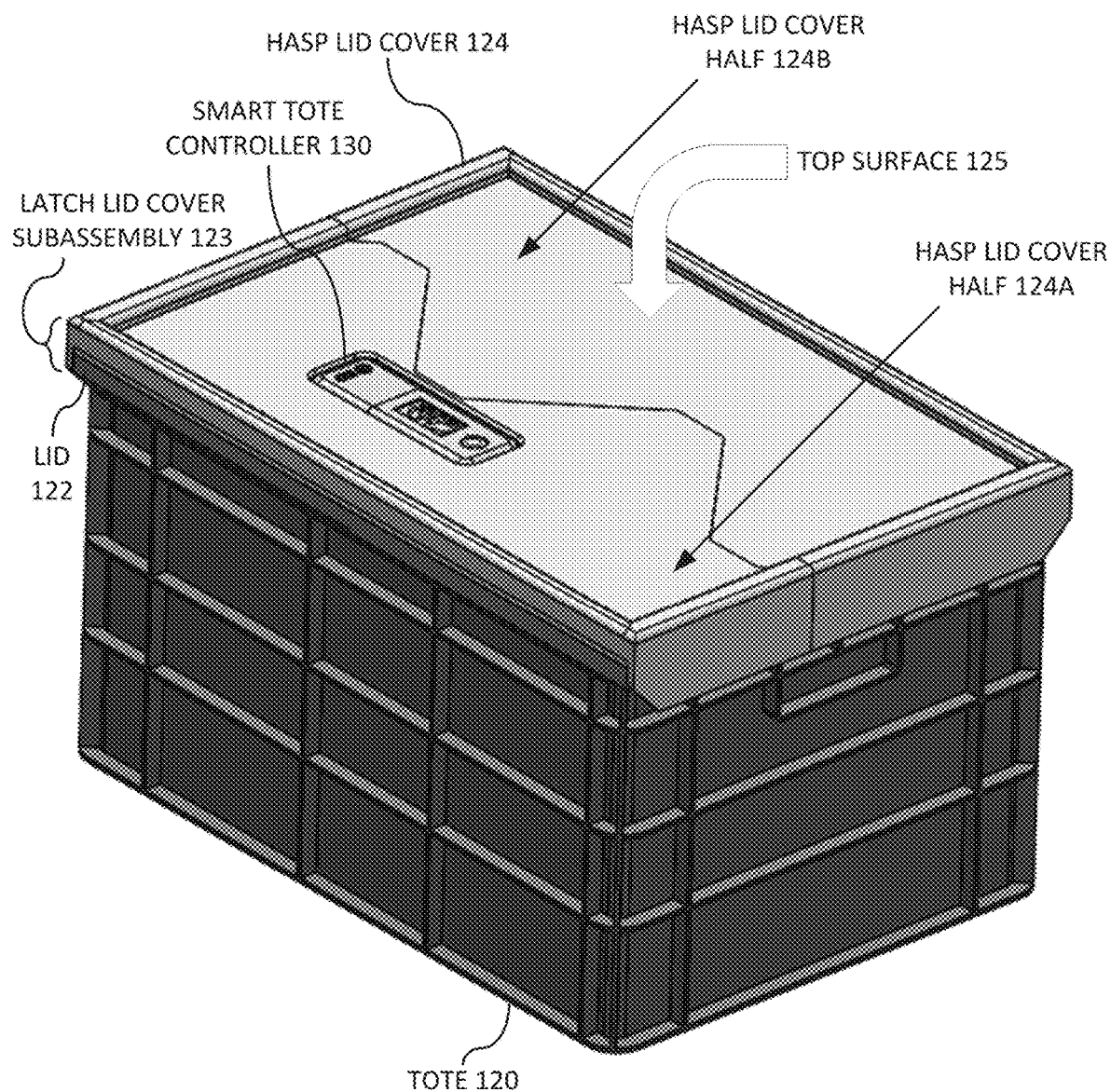
FIG. 8C depicts a perspective view of a tote with a lid attached to the hasp lid halves from FIG. 8A and FIG. 8B, according to various aspects of the subject technology.

FIG. 8C depicts a perspective view of tote 120 with lid 122 attached to hasp lid cover half 124A and 124B from FIG. 8A and FIG. 8B, according to various aspects of the subject technology. hasp lid cover half 124A and 124B combine to form hasp lid cover 124, which is attached to lid 122 to form latch lid cover subassembly 123. Both hasp lid cover 124 and lid 122 of latch lid cover subassembly 123 may be constructed of deformable materials, such as a malleable plastic, to retain evidence of attempts to divert or tamper with tote 120. As shown in FIG. 8C, smart tote controller 130 may be recessed into top surface 125 such that top surface 125 is substantially flush with smart tote controller 130.

Figure 8D:
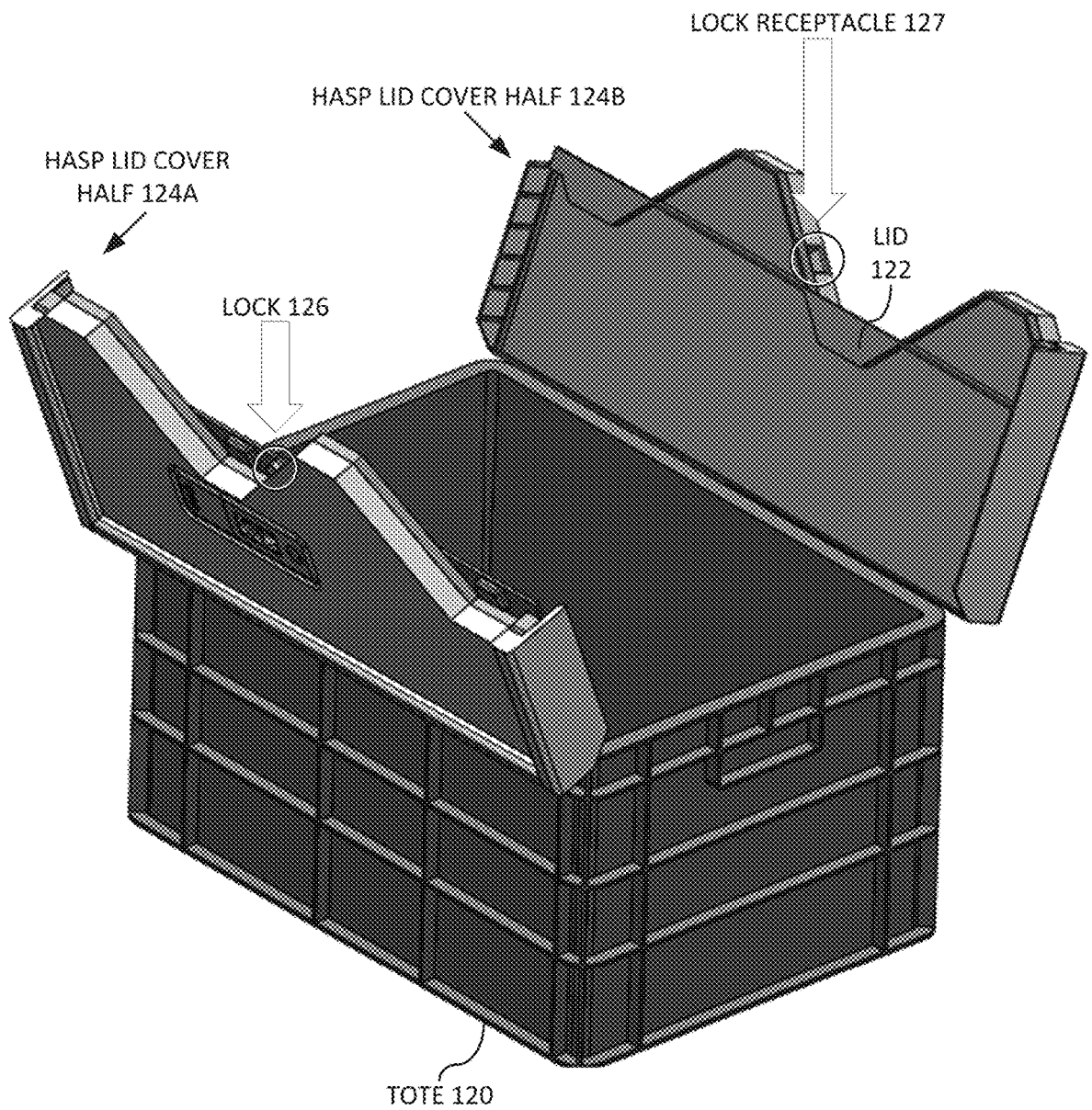
FIG. 8D depicts a perspective view of the tote from FIG. 8C with an opened lid, according to various aspects of the subject technology.

FIG. 8D depicts a perspective view of tote 200 from FIG. 8C with an opened lid 122, according to various aspects of the subject technology. For example, by retracting lock 126 from lock receptacle 127, the hasp lid cover halves 124A and 124B may be separated from each other, which in turn opens lid 122 of tote 120. Items such as medicine can then be placed within or retrieved from tote 120.

Figure 8E:
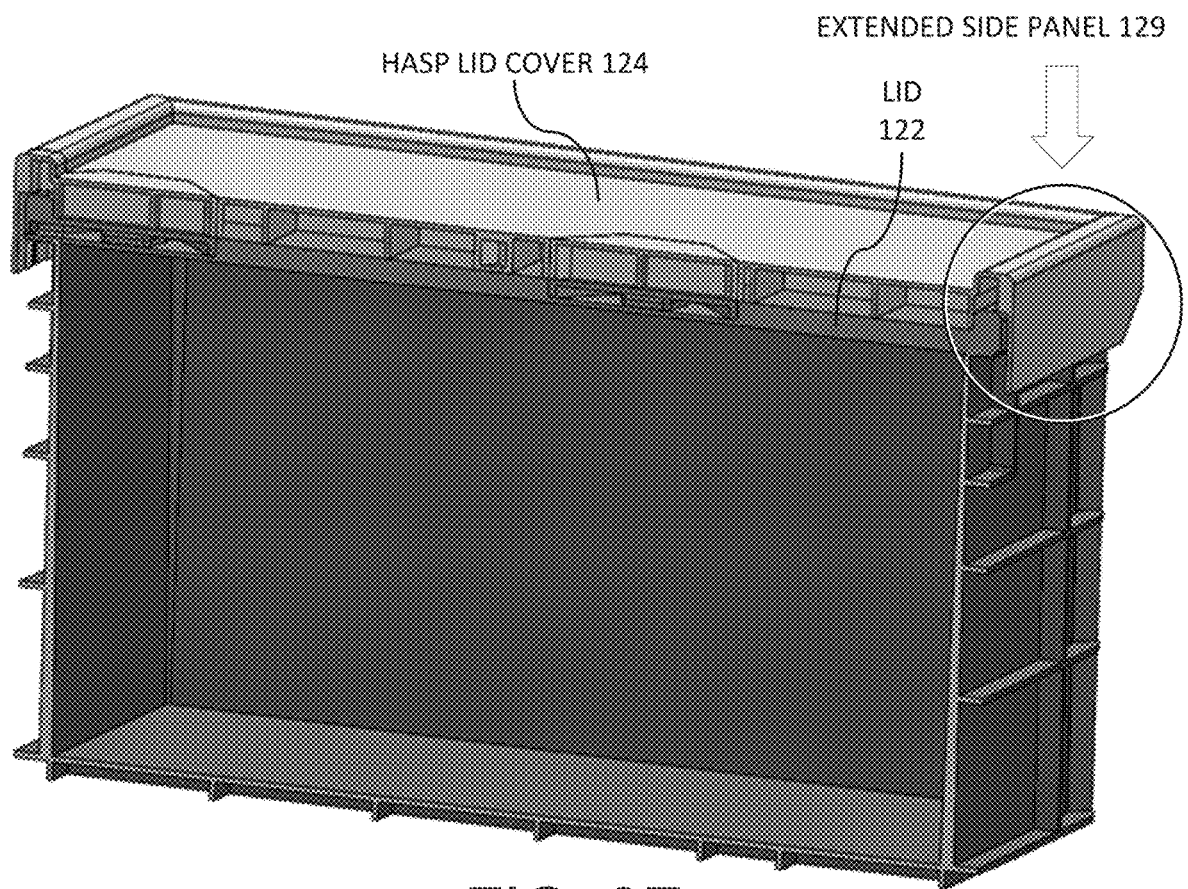
FIG. 8E depicts a cross sectional view of the tote from FIG. 8C to illustrate an extended side panel on the hasp lid, according to various aspects of the subject technology.

FIG. 8E depicts a cross sectional view of tote 120 from FIG. 8C to illustrate extended side panel 129 on hasp lid cover 124, according to various aspects of the subject technology. As shown in FIG. 8E, extended side panel 129 extends significantly beyond the lip of lid 122 to provide enhanced tamper resistance against prying of lid 122.

Figure 8F:
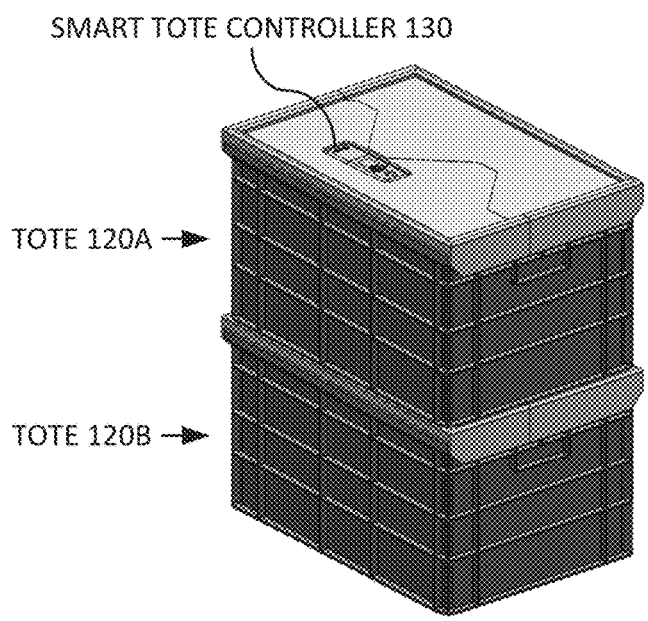
FIG. 8F depicts multiple totes with integrated smart tote controllers in a stacked configuration, according to various aspects of the subject technology.

FIG. 8F depicts multiple totes 120A and 120B each with an integrated smart tote controller 130 in a stacked configuration, according to various aspects of the subject technology. As shown in FIG. 8F, when the smart tote controller 130 is recessed into the hasp lid, then the totes can be readily stacked on top of each other to maximize space utilization.

FIG. 9 depicts various example user interfaces of a smart tote controller, according to various aspects of the subject technology. With respect to FIG. 3, like numbered elements may correspond to similar elements from FIGS. 6A-6D and/or FIGS. 8A-8F.

Display 365A shows a general purpose status screen, which may be shown by default when no user interaction is taking place. As shown in display 365A, the status screen may include several informational fields, such as location, environment status, authenticated user, patient, destination, estimated time of arrival (ETA), battery level, identification logo (e.g., care facility graphic), and network status. Referring to FIGS. 1, the location field may update according to a current reading from location sensor 158. The environment status field may update according to a current reading from temperature and humidity sensor 152, shock and vibration sensor 154, and tamper sensor 156. The authenticated user field may update according to the last verified user credentials received by IAM interface 168. Referring to FIG. 7B, the patient, destination, and ETA fields may be updated according to information received from server 114. The battery level may be updated according to estimated charge detected for power source 180. Network status may be updated according to the availability of connectable networks via communication interface 140.

In some implementations, the user may provide touch input on display 365A or button inputs to drill down on a specific field. For example, display 365B may include drill down listings for the authenticated user field, location field, patient field, and environment field. The authenticated user field may correspond to a chain of custody listing, which shows timestamped successful and unsuccessful user authentication events and locking/unlocking events. As shown in FIG. 9, a staff member S. Max may have previously successfully authenticated, opened the lock, and closed the lock. Thereafter, a different staff member D. Green may have used an incorrect smartcard to authenticate, resulting in a failed attempt. After retrieving the correct smartcard, D. Green may have successfully logged in.

The location field may correspond to a location history listing, which shows previously detected locations and transit paths. Optionally, the route may be displayed on a map. As shown in FIG. 9, the smart tote may have originated at a distribution center before moving to a pharmacy.

The patient field may correspond to an inventory history, showing the contents of the tote that are intended for the associated patient, or J. Doe. As shown in FIG. 9, the tote may initially be empty, and S. Max may later add drug #1, #2, #3 into the tote, as indicated by the chain of custody.

The environment field may correspond to an environment history, showing whether sensors detect parameters within normal ranges or abnormal ranges. For example, excess g-force of 4 g may have been detected while the tote was in transit from the distribution center to the pharmacy. For example, rough road conditions or sudden braking may cause the excess force to be detected. However, since the smart tote contained no inventory at the time, the environmental state may remain as "OK." When the smart tote does contain inventory and the environmental conditions exceed safe parameter ranges specified for the inventory, then the abnormal conditions may be logged in the environment history and the environment field may display a warning or error to inform the user that the inventory may be spoiled, ineffective, or unsafe for use.

Display 365C shows a tote inventory screen, which may be shown when the tote is open and items can be added or removed to the tote. As shown in FIG. 9, the tote inventory screen may list the item name (drug name), dosage size, and quantity for each item. These fields are exemplary and other fields may be selected. The user may provide touch input or button inputs to select the [+], [−], and [Remove] buttons to adjust the quantity of each item, or select the [Add new] button to add new inventory items. In some implementations, display 365A-365C may be shown on a remote device, such as a tablet, smartphone, laptop, or desktop computer.

Figure 10:
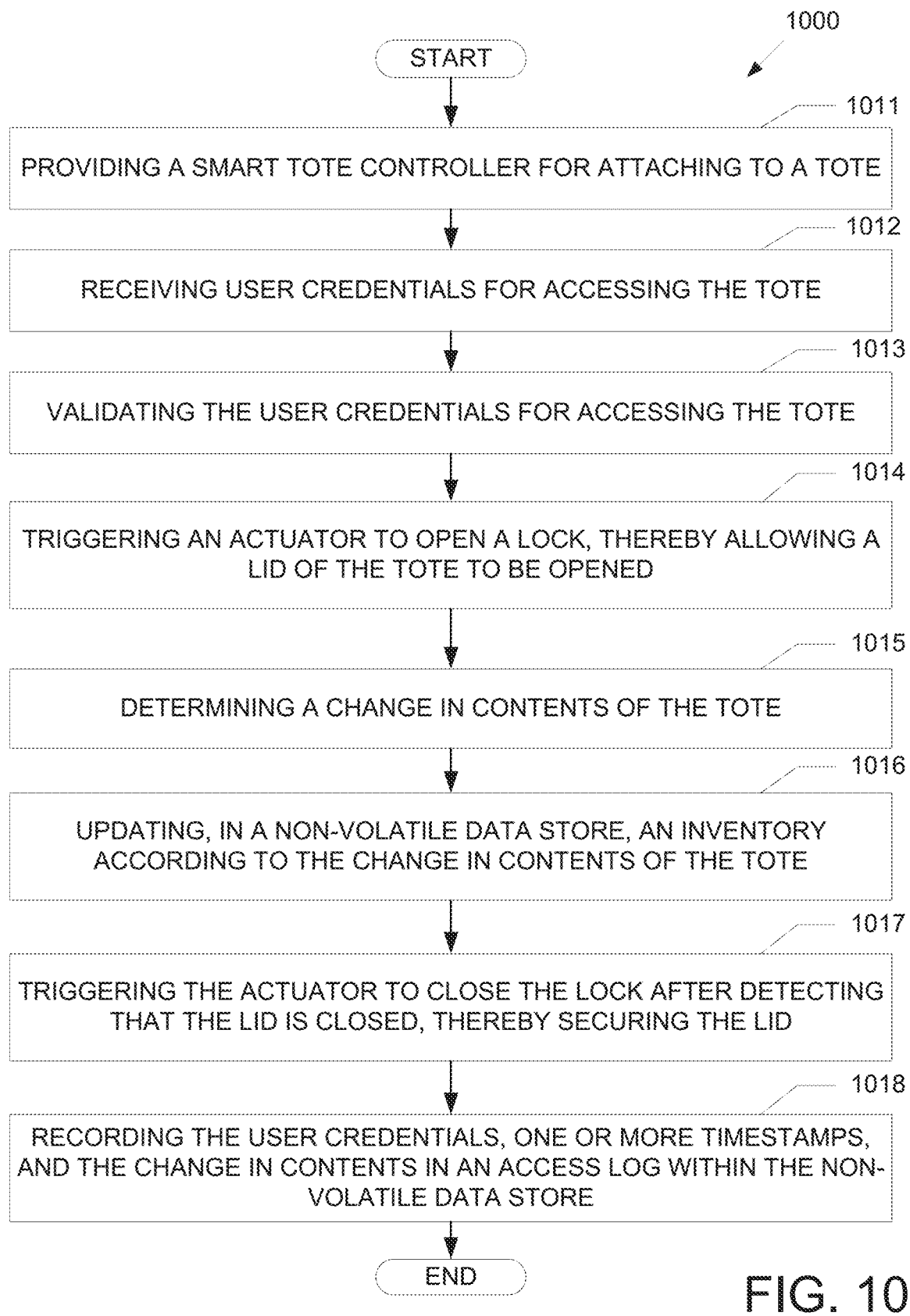
FIG. 10 depicts an example process for using a smart tote controller to provide secure storage, transport, and dispensing of items with automatic inventory, item condition, and chain of custody tracking, according to various aspects of the subject technology.

FIG. 10 depicts an example process 1000 for using a smart tote controller to provide secure storage, transport, and dispensing of items with automatic inventory, item condition, and chain of custody tracking, according to various aspects of the subject technology. For explanatory purposes, the various blocks of example process 1000 are described herein with reference to FIGS. 1, 6A-6D, 7A-7B, and 8A-8F, and the components and/or processes described herein. The one or more of the blocks of process 1000 may be implemented, for example, by a computing device, including a processor and other components utilized by the device. In some implementations, one or more of the blocks may be implemented apart from other blocks, and by one or more different processors or devices. Further for explanatory purposes, the blocks of example process 1000 are described as occurring in serial, or linearly. However, multiple blocks of example process 1000 may occur in parallel. In addition, the blocks of example process 1000 need not be performed in the order shown and/or one or more of the blocks of example process 1000 need not be performed.

In the depicted example flow diagram, a smart tote controller is provided for attaching to a tote (1011). Referring to FIG. 6CCC, this may correspond to providing smart tote controller 130B for attaching to tote 120. More specifically, smart tote controller 130B may be embedded in hasp lid cover 124, which is then attached to lid 122 of tote 120, as shown in FIG. 6D.

Process 1000 may continue with receiving user credentials for accessing the tote (1012). For example, referring to FIG. 1, processor 134 may receive user credentials via IAM interface 168. As discussed above, this may correspond to a unique identifier read from a smartcard or other token, or a biometric identifier.

Processor 134 may continue to validate the user credentials for accessing the tote (1013). For example, referring to FIG. 1A, processor 134 may utilize secure crypto-processor 184 to verify that the user credentials are valid against an encrypted authorized user database.

Processor 134 may continue to trigger an actuator to open a lock, thereby allowing a lid of the tote to be opened (1014). For example, referring to FIG. 1 and FIG. 6C, processor 134 may utilize actuator interface 166 to trigger actuator 167 via actuator cable 133 to open lock 126. Once lock state 128 is set to open, then lid 122 may be manually opened by the user as demonstrated by lid 222 of FIG. 8D. Alternatively or additionally, a spring, a mechanical opener, or another assistive device may be used to prop open lid 122.

Processor 134 may determine a change in the contents of the tote (1015). For example, referring to FIG. 1 and FIG. 9, a user interface similar to one shown on display 365C may be presented to the user to allow inventory to be edited according to a change in contents of tote 120. The user may use button interface 160, display interface 164, microphone 172, and/or a remote device to provide user input for adjusting the inventory according to the change in contents, wherein items may be added or removed. In some implementations, a radio frequency identification (RFID) tag or another tracker may be attached to the items in tote 120, and communication interface 140 and/or sensors 150 may detect the addition or removal of items based on the presence or absence of RFID tags.

Processor 134 may continue to update, in a non-volatile data store, an inventory according to the change in contents of the tote (1016). For example, referring to FIG. 1, the determined change in contents (1015) may be used to adjust an inventory stored in non-volatile data store 137.

Processor 134 may continue, after detecting that the lid is closed, to trigger the actuator to close the lock, thereby securing the lid (1017). For example, the user may manually close the lid. In some implementations, the spring, mechanical opener, or other assistive device used to open the lid (1014) may also be used to close the lid, for example by triggering a closing of the lid after a predetermined timeout period expires, for example 30 seconds. Referring to FIG. 1, the lid may be detected to be closed by using sensors 150 and/or actuator interface 166. Once the lid is detected to be closed, referring to FIG. 1 and FIG. 6C, processor 134 may utilize actuator interface 166 to trigger actuator 167 via actuator cable 133 to close lock 126 after lid 122 is closed, or after hasp lid cover halves 124A and 124B have been moved back to a closed position.

Processor 134 may continue recording the user credentials, one or more timestamps, and the change in contents in an access log within the non-volatile data store (1018). For example, referring to FIG. 1, the access log may be stored in non-volatile data store 137. Data from sensors 150 may also be recorded into sensor logs stored in non-volatile data store 137.

Referring to FIG. 7A, when a connection to server 114 is available, then a synchronization may occur between at least a portion of the logs stored in non-volatile data store 137 and the data stores in server 114. In some implementations, the logs may be truncated by most recent date ranges to reduce storage and processing overhead. In this manner, automatic inventory tracking 115, item condition tracking 116, and chain of custody tracking 117 can be provided across multiple networked smart totes. As shown in display 365A and 365B in FIG. 9, stored data logs for each individual smart tote may also be inspected by the user to provide evidence of important events that occurred up to the present time. Alternatively, server 114 may be queried for the same information, or smart totes may be queried directly to provide real-time data updates when network connectivity is available.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a controller, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more controllers, sub programs, or portions of code). A computer program can be deployed to be executed on one computer or on multiple computers that are located at one site or distributed across multiple sites and interconnected by a communication network.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Secure Tote

As discussed previously with respect to FIGS. 6-10, the subject technology may relate to a smart tote system and method for securely transporting controlled and non-controlled medication in acute or non-acute healthcare settings. The disclosed system enables evidence for real time location tracking, chain of custody, environmental state of the transport, and automatic inventory tracking and loading of medication both at rest and transit. The system may include a plurality of user interfaces along with actuator that unlock the tote with a secured authorization from a server. The system and/or method may implement a machine learning (ML) inference and data analytics to optimize power consumption (e.g., on the smart tote device) based on its awareness of spatial context. The system and/or method may further include a handheld device or mobile application that can scan multicolor led and identify system status during manufacturing or field.

Existing medication transport solutions do not provide any data or evidence on the environmental state of the transport (temperature, humidity, shock, vibration), security, real time location, or assist the end user in automatic inventory tracking and loading of assets. Some solutions (e.g., involving a tote that transports medication from a central pharmacy or a wholesale distribution to a clinic) use zip ties to secure the tote and provide no evidence to real time location, security, and environmental condition of the transport. Few implementations provide silo solutions which just address the cold chain tracking of medications that requires temperature evidence. The proposed systems and methods include an enterprise solution that addresses the above short comings using a smart tote of the subject technology.

Accordingly, systems and methods associated with secured medication transport solutions in non-acute and acute healthcare settings is disclosed herein.

The disclosed solution may include a smart tote with plurality of user interfaces, one or more server authorized actuator locks, one or more environmental sensors to monitor the state of transport, and may include location tracking and evidence of custody and enables enterprise solution for inventory tracking and guided loading of medication.

According to various implementations, the system comprises a processor, memory, input/output device, environmental sensor, tamper detection mechanism, and wireless interface.

Other features may include one or more of the following: E-ink display, buttons, microphone, buzzer and multicolor LED for user interface; Identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present evidence on state of the transport; drive circuitry for piezo electric buzzer to provide audio feedback to the user; microphone interface circuitry for the user to provide wakeup words and or voice; Actuator latch drive circuitry and latch state read back methods; memory interface to store state and statistics of transport; environmental & tamper detection sensor interface to monitor temperature, shock and vibration; and crypto and secure element interface to safely store public/private keys.

In some implementations, the E-ink may display icons such as loading dock or in transit to show the current status of associated medication that is been tracked.

In some implementations, the E-ink may display shipment tracking details. For example, information such as from & to destination, travel time and who signed at tote departure and arrival may be displayed or otherwise communicated by a user interface.

In some implementations, the E-ink may display information collected from the environmental sensor. For example, information such as temperature of medication in transit, monitor tamper evidence sensor signal, humidity, shock and vibration over time may be displayed or otherwise communicated by a user interface.

In some implementation, the multicolor LED user interface may act as a glanceable status indicator. In this regard, the LED color, flash pattern and intensity may indicate different status based on user accessing the secure storage location and workflow.

Example 1: During medication loading workflow the led lighting may guide the user to the medication at a glance.

Example 2: If the medication in the tote expired then the LED may flash red.

Example 3: During medication audit the system may guide by lighting the LED's so the user can identify the med easily.

Example 4: If the battery level lower than threshold then the led may flash.

Example 5: Led color and flash pattern may indicate that an authorized user unlocked the tote.

A handheld device may scan the led color, intensity and flash pattern and identify it's glanceable status during manufacturing or in field. The device may comprise an inspection equipment or a mobile application, and/or an optical reading device to read the multicolor visual indicator and obtain the failure modes and conditions on the smart tote.

An authentication system may automatically determine a plurality of user authorization methods, and the user may then select one or more of the determined authorization methods to unlock the smart tote. User identity may be securely transmitted to the server, and authorization may be returned from the server to unlock the smart tote. In some implementations, the authentication mechanism may use contactless smart card, and in some implementations the authentication mechanism may use barcode, biometric identification, ECG based wearable device, or a mobile phone. In some implementation, the authentication mechanism may include remote authentication. For example, if the user loses their badge or smart phone, super user may provide remote authentication.

In some implementations, the disclose system and method may include a sensor interface system, which monitors NIST traceable environmental sensor & tamper detection data in real time.

An audible sound may indicate user actions such as presenting badge to the smart lock or when an actuator command is been executed. For example, in some implementation a piezo beeper may be used with different tones to indicate different actions.

The system and/or method may include communication architecture (CA), which may use plurality of PAN protocols such as (802.15.4/BLE) to talk to the remote device. In this regard, the system and/or method may utilize the CA to achieve one or more of the following features: beacon for asset tracking; environmental sensor and tamper detection monitoring; Real time and offline mode support; and tote content identification and inventory tracking. In some implementations of smart tote, the CA may bypass hospital IT, thereby reducing implementation time (e.g., implementing a drop ship model based on PAN protocol support).

The system and/or method implementing communication architecture (CA) may support an offline mode. When a network connection to the field hub or gateway is lost the smart tote may still allow the user to continue with their action, and the system may store and forward the actions when the network is restored.

The system and/or method implementing communication architecture (CA) may enable the smart tote to broadcast beacons to remote host with the medication information for asset tracking. In some implementations, users may also read the beacons using a mobile device such as a phone or tablet.

The system and/or method may automatically identify the contents in the tote and assist the end user in inventory tracking and loading the medication.

In some implementations, the disclosed system and/or methods may include power architecture that utilizes disposable batteries or, in other implementations, the power architecture may implement rechargeable battery or a supercapacitor.

A method for conserving power in battery operated devices based on system factors and user preference is disclosed. Devices may be placed in low power states (ranging from system off state to various levels of sleep state) and may be woke up periodically (wake up period) to enable radio communications, to check in with a gateway/hub for updates or to perform transactions.

The low power state and wake up period may be configured by the gateway/hub for devices based on system usage factors and user preferences.

In some implementations, environmental sensors such as occupancy sensors may be used. In some implementations, a microphone may be used. Activation to wake up the device from deep sleep mode may be by key word activation, user action by pushing a button, or system usage factors such as user presence, or office schedule.

A system and method for energy harvesting using plurality of sources is disclosed to increase smart tote operation life. In some implementations, the system or method uses piezo transducers interfaced to buttons or electromagnetic induction from lock actuator action or wireless energy from RF sources to harvest energy.

The following commentary and illustrations define a solution for storing, transporting and dispensing items using the foregoing technology.

As shown in FIGS. 6A and 6B, the smart tote concept may include a lockable device activated bin for secure item storage and transport.

The smart tote may be retrofitted to an existing tote for controlled security.

As discussed previously with regard to FIG. 8F, the smart tote may include an off-the-shelf lidded tote that includes reader module and electro-mechanical latch and latch bracket. The reader module may include one or more of a NFC reader, LEDs, light pipe, global positioning system (GPS) device, shock recording, batteries, audio indicator, barcode, temperature monitoring, and e-ink display. The e-ink display may visually (and/or audibly) indicate to and from information, content information, date, etc. The smart tote may communicate wirelessly to other devices to manage access and inventory. Automatic population of stock numbers may be performed when received by clinic. The smart tote may include a latch lid cover subassembly and a hasp lid cover that are mechanically attached to a tote's existing lids. (See FIGS. 8D and 8F.)

The latch lid cover subassembly may include a latch lid cover, smart reader and electro-mechanical latch. The latch lid cover may include features that mount the smart reader and latch. The reader may sit flush to the top exterior of the lid cover. By sitting flush, multiple smart totes may be stacked on top of each other. The smart reader's batteries may be externally accessed. When the smart reader batteries expire, the latch may remain in the locked position, and the batteries may be replaced to continue operation. The smart reader LED may indicate smart tote location. An audio indicator may alert an unlocked or open lid. The hasp lid cover may include a feature that interfaces with the latch. (See FIGS. 8A-8F.)

The smart tote reader module and latch Hook may be designed to indicate an attempt to divert. They may include material that may be deformed showing tamper evidence. Both the latch lid and hasp lid may have extended side panels to increase security against diversion by prying up the lids. (See FIGS. 8D and 8E.)

Connected Bin Inventory Tracker

Another aspect of the disclosure relates to a smart touch to retrieve system and corresponding methods for inventory management of items in both non-acute and acute care settings. The disclosed touch to retrieve system includes a wireless connected device which interfaces to a gateway and an enterprise level inventory management application. A connected bin inventory tracker within the touch to retrieve system may provide configurable buttons, display and multi-color LEDs as a user interface. The touch to retrieve system may be used in a multitude of locations where medication and supplies need to be managed including med rooms, med carts, supply rooms, operating rooms, emergency rooms, and intensive care units. In some implementations, all or part of the touch to retrieve system is placed inside refrigerators to manage refrigerated items. In some implementations, the touch to retrieve system includes a mobile device used for location tracking of items within the hospital. In some implementations, the disclosed system and device and corresponding method implements machine learning (ML) inference and data analytics to optimize power consumption on the touch to retrieve system or a connected bin inventory tracker included therein based on its awareness of usage context. In some implementations, the disclosed system and device and corresponding method includes handheld device or mobile application that can scan multicolor led and identify system status during manufacturing or field. The disclosed system and device and corresponding method is an enterprise level solution that provides inventory management and location tracking of items in a multitude of use cases.

Existing solutions for inventory management in non-acute care settings is performed manually and is not accurate. A connected bin inventory tracker may be attached to off the shelf bins or smart bins and provides a screen and buttons for user interaction. The configurable display can show the item name and quantity available and buttons are used to increment or decrement quantities. The user interface is configurable to enable other functionality such as automated loading and guide by light to aide in finding items. The connected bin inventory tracker is connected to an enterprise level medication management software which enables end to end inventory management.

The disclosed smart touch to retrieve technology has two-way communications which enables a multitude of functionalities including guide by light and display updates.

The connected bin inventory tracker, in some implementations, may include a mobile device which may be used for tracking of items. In asset tracking mode the connected bin inventory tracker may beacon its unique ID over the wireless interface, for location tracking of mobile bins and containers.

In some implementation, the connected bin inventory tracker is a stationary device attached to bins in open shelf inventory locations or behind cabinets/locks.

In some implementations, the connected bin inventory tracker is located inside refrigerators. The connected bin inventory tracker may be fashioned of material hardened to withstand refrigerated environments.

In some implementations the connected bin inventory tracker is a mobile device used for asset tracking of items.

Figure 30:
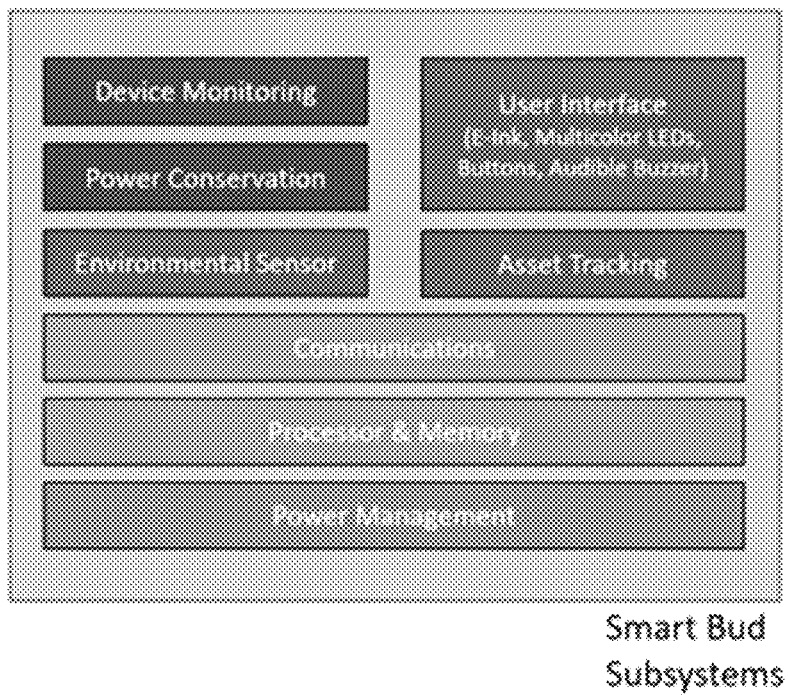
FIGS. 30 and 33 depict example subsystems of the disclosed smart bin system and/or device, according to various aspects of the subject technology.
Figure 33:
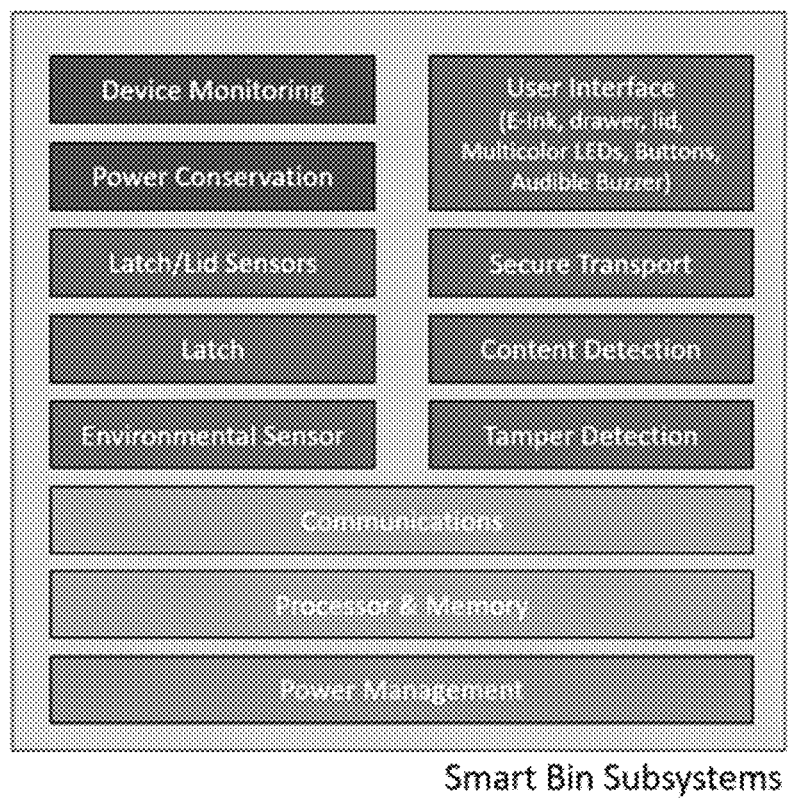

With brief reference to FIG. 1A, FIG. 30, and FIG. 33, the disclosed system and/or device may include an E-ink user interface 164. In some implementations, the user interface may display status of the connected bin inventory tracker using icons such as battery level, network connectivity, and/or status of the latch and door. In some implementations, the user interface may display alerts such as expired medication, below par, tamper detection etc. In some implementations, the user interface may display information collected from the environmental sensor. For example, the user interface may display information such as temperature of medication, monitor tamper evidence sensor signal, humidity, shock and vibration over time. In some implementations, the user interface may display item name and item quantity. In some implementations, the contents of the display is configurable by the user.

In some implementations, the user interface may include buttons that have different functionality depending on the context:

Example 1: In remove workflows the buttons function as decrement and increment quantity of the items Example 2: In load workflows the buttons function as Accept/Reject quantities Example 3: In other workflows buttons are used to navigate through menus of E-ink. In some implementations, the user interface may function as a glanceable status indicator. For example, LED color, flash pattern and intensity may indicate different status based on user accessing the secure storage location and workflow.

Example 1: During medication loading workflow the LED lighting can guide the user to the medication at a glance.

Example 2: If the medications being secured or monitored by the connected bin inventory tracker has expired, the LED can flash red or other predetermined color.

Example 3: During medication audit the system may guide by lighting the LED's so the user can identify the med easily.

Example 4: If the battery level lower than threshold led can flash in low intensity Example 5: LED color and flash pattern to indicate authorized user unlocked the latch.

Example 6: Specific LED colors assigned to users who are using the system simultaneously. For example, two users with different pick lists access the system at once; the connected bin inventory trackers for user 1 may flash one color and the connected bin inventory tracker s for user 2 may flash a different color.

In accordance with the above system and/or device, disclosed is a method by which a handheld device may scan the LED color, intensity, and flash pattern and identify its status during manufacturing or in field.

The foregoing system and/or method may include use of an inspection equipment or a mobile application. For example, an optical reading device may be implemented to read the multicolor visual indicator and obtain the failure modes and conditions on a connected bin inventory tracker.

Access to a connected bin inventory tracker may be authenticated via remote authentication. For example, users can enter credentials at tablet or PC or use a standalone authentication module to perform load workflow or reconfigure the connected bin inventory tracker. If a user loses their badge or smart phone the super user can provide remote authentication.

The system, device, and/or method may include producing an audible sound indicating user actions such as when an actuator command is been executed. For example, the audible sound may be produced by a piezo beeper with different tones to indicate different actions.

In some implementations, the system, device, and/or method may include an environmental sensor interface system that is capable of monitoring NIST traceable temperature sensors used for cold storage of vaccines. The environmental sensor interface system may be capable of monitoring plurality of sensors including: temperature, humidity, vibration, orientation and acceleration of the connected bin inventory tracker.

In some implementations, the system, device, and/or method may include a tamper detection system that detects tamper via the foregoing environmental sensors and/or additional sensors (e.g. optical and electromagnetic sensors).

In some implementations, the system, device, and/or method may include a communication and power subsystem that supports a distributed architecture. In such implementations, each connected bin inventory tracker may include its own wireless communication interface and power source.

In some implementations, the communication and power subsystem may support a central architecture where multiple connected bin inventory trackers are wired to a single controller. The controller may provide wireless communications and/or power source for multiple connected bin inventory trackers. In such implementations, the number of wireless communication interfaces, electronics and power sources may be reduced, which may be desirable in cases where many connected bin inventory trackers are co-located.

The system, device, and/or method may include communication architecture (CA), which may use plurality of PAN protocols such as (802.15.4/BLE) to talk to the remote device. In this regard, the system, device, and/or method may utilize the CA to achieve one or more of the following features: beacon for asset tracking; environmental sensor and tamper detection monitoring; Real time and offline mode support; and tote content identification and inventory tracking. In some implementations of a connected bin inventory tracker, the CA may bypass hospital IT, thereby reducing implementation time (e.g., implementing a drop ship model based on PAN protocol support The system, device, and/or method may include power architecture that implements disposable batteries or rechargeable batteries.

The system, device, and/or method may include an energy harvesting system that uses plurality of sources to increase connected bin inventory tracker operation life. In some implementations, the system, device, and/or method may include piezo transducers interfaced to buttons or electromagnetic induction from lock actuator or drawer/door open and close action or wireless energy from RF sources to harvest energy.

The system, device, and/or method may include a power management subsystem for conserving power in battery operated devices based on system factors and user preference. In this regard, a method for conserving power may include placing devices in various low power states to wake up periodically (wake up period) and enable radio communications and check in with a gateway/hub for updates or to perform transactions. Power saving states may adjust device responsiveness vs power savings. The low power states and wake up period may be configured by the gateway/hub for devices based on system usage factors and user preferences.

In some implementations, the power states may be adjusted based on user presence, if users are present, the devices are placed in more responsive states in anticipation of the system being used. If users are not present, the devices are put in less responsive states, to maximize power savings.

In some implementations, the power states may be adjusted by ML algorithms running on the hub/gateway and/or cloud.

In some implementations, the user presence may be detected in plurality of methods including users logging into the system, by occupancy sensors such as motion, radar, and proximity sensors. Occupancy sensors are envisaged to be powered devices located in the med room area and interface to the gateway/hub.

In some implementations, the users input office schedule into the system and power states are adjusted based on this schedule.

In some implementations, the system, device, and/or method uses microphones with key word activation to wake up the device from deep sleep mode.

In some implementations, the system, device, and/or method may include sensors which monitor health of a device (e.g., including the foregoing environmental sensors) and additional sensors monitoring the operation of the device such as currents, voltages, temperatures of critical components, etc.

In some implementations, the system, device, and/or method may include a device monitoring subsystem that transmits collected data to the hub/gateway/cloud for analytics.

In some implementations, the system, device, and/or method may include an asset tracking subsystem wherein the connected bin inventory tracker is placed inside or affixed to the outside of off the shelf containers such as totes to convert them to a trackable container. In some implementations, an asset tracking subsystem plays a beacon role, advertising its unique ID, so it may be identified and located for asset tracking by hubs or mobile devices.

Unique ID and configuration information including contents of the container may be stored locally on the device in non-volatile memory. This information is also available on an online database.

The access controller portion of interactive inventory device 130 may also be referred to herein as an asset tracking inventory device, or as a modular "Internet of Things" (IOT) device or "IOT inventor tracker" or "IOT Smart tracker" or "touch to retrieve" device. In this regard, the interactive inventory device 130 may be tracked by hubs which are in placed in areas of interest within a physical building or organization. As the device moves between hubs located in the area, each hub may be able to read a beacon sent by the device and identify the device. Hubs are placed in areas of interest such as shipping and receiving, staging areas, hallways etc. Beacons may also be read by mobile devices. In some implementations, an asset tracking smart bud may be queried directly by hubs or mobile devices for additional information such as contents of smart bud, destination, battery level, environmental sensors etc. Alternatively, the mobile device and/or hubs are network connected and may be configured to retrieve information about the smart bud from a network database using the beacons unique ID. In some implementations, wireless signal characteristics may be used to locate and guide the user to the smart bud modules. This may be useful in scenarios where a specific device needs to be located and a user may be guided to the unit they are looking for.

As described previously the IOT inventory tracker is a device that may be attached to a bin. In some implementations, a user can keep track of inventory by using a "take" button or "return" button. The items description, quantity, etc. may be shown on the e-ink display. The IOT inventory tracker may communicate wirelessly with other devices. (See FIGS. 1B and 1C.)

The IOT inventory tracker (see FIGS. 1B and 1C) may include an e-ink display, take/return buttons, multi-colored LED indicator, and external snap-on battery access cover for easy access.

The IOT inventory tracker may use common batteries such as AAA batteries.

The IOT inventory tracker may be configured to withstand a refrigerated environment. The material and components may be used at lower temperatures. The IOT inventory tracker may be placed in a refrigerator.

The IOT inventory tracker have overlapping features, interlocks and materials to indicate tamper evidence.

The IOT inventory tracker housing may include clip-on features with a push button clip and may be attached to off-the-shelf bins. (See FIG. 1E.)

Further Implementations

Further features are described herein for facilitating rapid deployment of a variety of devices within a clinical setting. The clinical settings for the described features may include a non-acute health service facility such as a doctor's office, pharmacy clinic, outpatient clinic, institutional infirmary (e.g., school nurse's office), hospital, or the like. In such settings, the physical resources available, including space and network coverage, may be limited. Furthermore, such facilities may face limited resources for installing and managing critical dispensing devices. The features described may be used independently or integrated in various combinations to provide efficient and secure dispensing systems compatible with dynamic clinical needs.

Cabinet Smart Lock

One aspect of the disclosure relates to a system, device, and/or method that includes an enhanced lock for cabinet doors or drawers ("cabinet smart lock" or "smart lock"). The described smart lock system, devices, and corresponding methods facilitate securing medication inside cabinets and drawers in both acute and non-acute healthcare settings. The smart lock may be a wirelessly connected device with a locking mechanism to secure the medication, authentication capabilities to provide secure access and a user interfaces.

The smart lock is configurable and users may be able to authenticate directly at the smart lock, or can use other methods such as logging onto a tablet or using a standalone authentication module to access the system or component connected thereto (e.g., a cabinet smart lock). According to various implementations, one or more user interfaces may include multi-color light emitting diodes (LEDs) and E-Ink display which are also configurable. Some implementations may include a machine learning (ML) inference and data analytics engine to dynamically adjust a power state of the smart lock to optimize power consumption on a smart lock device and/or system based on analysis of a lock's usage context. Some implementations may include a handheld device or mobile application that can scan multicolor LED and identify system status during manufacturing or field.

Existing solutions in non-acute space for securing medications involve off the shelf keyed or combination locks that are installed on the cabinets and drawers. Users use the same key or combination numbers to access medication, which is not traceable as to who accessed the cabinets. Wireless lock technologies that connect directly to a phone or mobile device are generally for personal use, but do not integrate into an enterprise level solution. The systems and method described herein includes an enterprise level solution that provides traceability and is integrated with medication workflows. The described systems and methods address these and other shortcomings of the existing lock technologies.

Figure 11:
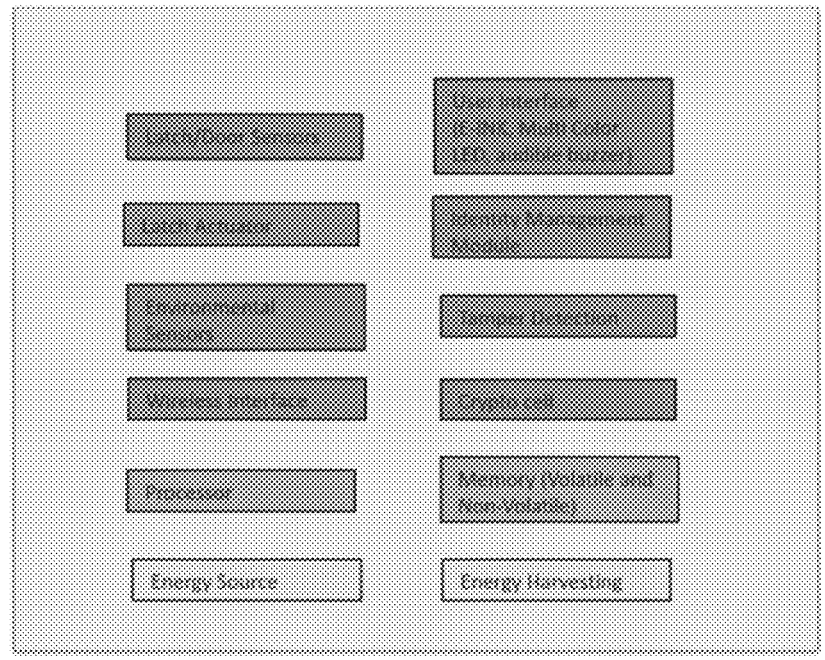
FIG. 11 depicts components of the disclosed smart lock system and/or device, according to some aspects of the subject technology.

Disclosed is a smart lock system, device, and methods used to secure cabinets and drawers in non-acute and acute healthcare settings:

FIG. 11 depicts components of the disclosed smart lock system and/or device, according to some aspects of the subject technology. In these examples, the system includes plurality of user interfaces, a server authorized actuator lock, lock and door sensors, identity authentication module, and other components that enable an enterprise solution for securing medication and guided loading of medication.

The E-ink user interface of the device may, in some implementations, display status of the smart lock system using icons such as battery level, network connectivity, status of the latch and door.

The E-ink user interface of the device may, in some implementations, in some implementations may display alerts such as expired medication, medication below par, tamper detection and etc.

The E-ink user interface of the device may, in some implementations, display information collected from the environmental sensor. Examples of such information collected include temperature of medication, monitor tamper evidence sensor signal, humidity, shock, and vibration over time.

The E-ink user interface of the device may, in some implementations, dynamically display information based on configuration associated with the user as to the contents of the display.

In some implementations, the multicolor LED user interface may act as a glanceable status indicator. The LED color, flash pattern, or intensity may be adjusted by the device (or in response to a control signal from a central control server) to indicate different status. The status may be based on user accessing the secure storage location, workflow, inventory level, or other detectable characteristic of the device or contents thereof.

Example 1: During medication loading workflow the LED lighting can guide the user to the medication at a glance.

Example 2: If the medications being secured by the smart lock has expired the LED can flash red.

Example 3: During medication audit the system may guide by lighting the LED's so the user can identify the med easily.

Example 4: If the battery level lower than threshold LED can flash in low intensity.

Example 5: LED color and flash pattern to indicate authorized user unlocked the latch.

Also provided is a computer implemented method by which a handheld device can scan the LED color, intensity and flash pattern and identify its status during manufacturing or in field. The computer-implemented method may be performed under control of one or more processing devices (e.g., CPUs or computer systems and/or devices).

The method may be implemented, in whole or in part, using an inspection equipment, a mobile application, and an optical reading device to read the multicolor visual indicator and analyze the reading to determine the failure modes and conditions on smart lock. Reading the indicator may include capturing an image of the LED. Reading the indicator may include capturing a series of images of the LED. The series may be captured for a period of time or number of frames identified using a configuration value. The series may be captured based on information encoded by the LEDs. For example, a preamble pattern or color may identify the start or end of a status sequence. When the device reads this pattern for a second time, the device may terminate reading and being the analysis of the captured image(s).

The authentication system may automatically determine a plurality of user authorization methods. The user may select one of the determined authorization methods to unlock the smart lock.

Features are also described for securely transmitting a user identity to a server and transmitting an authorization to unlock the smart lock. The authentication may, in some implementations, include reading data from a contactless smart card. In other implementations, it may use barcode, biometric identification, ECG based wearable device, a mobile phone, or a combination of the authorizations to request unlocking of a smart lock.

The authentication may include remote authentication. For example, users can enter credentials at tablet or PC or use a standalone authentication module to gain access to the smart lock or if the user loses their badge or smart phone a super user can provide remote authentication.

The sensor interface in an environment associated with a smart lock may monitor NIST traceable environmental sensor or tamper detection data in real time (e.g., within a threshold period of time from actual occurrence of the sensed environment condition or tamper event).

The systems or methods may generate an audible sound acknowledging user actions such as presenting badge to the smart lock or when an actuator command is been executed.

For example, in some implementation, a piezo beeper may be configured to emit different tones whereby each tone indicates a different action.

The communication architecture (CA) for the systems and methods, may include one or more of a plurality of personal area network (PAN) protocols such as (802.15.4/BLE) to communicate with the remote device.

The CA may be configured to detect beacon signals for asset tracking, provide environmental sensor and tamper detection monitoring, generate real time and offline mode support, or identify tote contents and track inventory. Because some health care supplies are temperature sensitive, if an environmental sensor determines that the temperature or humidity to which an item was exposed is outside an expected range, the system may dynamically adjust to alert or prevent dispensing of exposed items. Similarly, a sensitive item may have been tampered with. The system may direct storage or prevent distribution of such items until the integrity is confirmed. The confirmation may include an authorized user verifying the item before being eligible for dispensing and use in the healthcare facility.

According to various implementations, the smart lock CA can bypass set up and attachment to hospital IT resources. This can reduce implementation time and make it a drop ship model because of PAN protocol support.

A smart lock device may be configured to act as a companion device for devices placed inside the enclosure to bridge communications. Connected devices placed inside enclosures, such as refrigerators and metal cabinets, may have their radio signals attenuated and have difficulty communicating to hubs located further away. In these cases, another device such as the Smart lock is used as companion device to enable reliable communication to the hub/gateway. Smart lock when acting as a companion device can fill two roles: (i) a slave role communicating to the hub; (ii) a master role communicating to the devices behind the enclosure.

Figure 12:
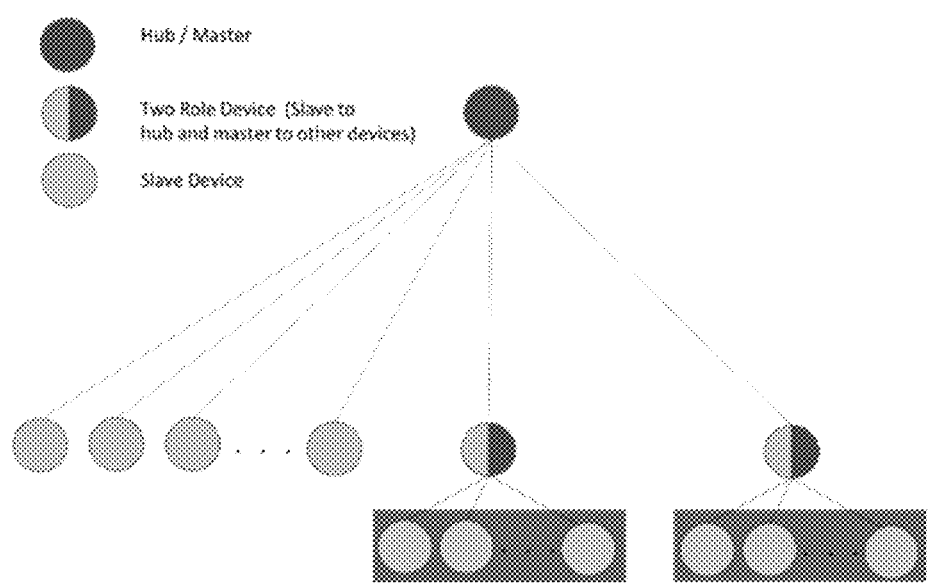
FIG. 12 depicts the disclosed interactive devices arranged in a multi-level network hierarchy, in which the devices communicate back to the hub either directly or through another device.

FIG. 12 depicts the disclosed interactive storage devices 130 arranged in a multi-level network hierarchy, according to various aspects of the subject technology. In the depicted example, interactive storage devices 130 may be configured to communicate back to a hub either directly or through another device.

The power architecture of the smart lock device and/or system may include disposable batteries and in other implementations it may include rechargeable batteries. To improve efficiency of the devices by conserving power in battery operated devices, the power management module may operate based on system factors and user preference. The power management module may be implemented within a specific device to conserve resources of the device in which it is implemented. The power management module may be a central device configured to manage power for a group of devices in data communication therewith.

Devices 130 may be placed in various low power states and may be configured to wake up periodically. The power management module may transmit a control signal to the devices in various low power states to wake up them up periodically (wake up period) and enable radio communications and check in with a gateway/hub for updates or to perform transactions.

The power saving states may be used to adjust device responsiveness versus power savings. The low power states and wake up period may be dynamically configured by the gateway/hub for devices based on system usage factors and user preferences.

Power states may be adjusted based on user presence. For example, if a sensor detects that users are present, the devices may be controlled to operate in more responsive states in anticipation of the system being used. If a sensor detects that users are not present or have left an area including one or more devices, the power management module may adjust devices within the area to operate in less responsive states, to maximize power savings.

User presence can detected in different ways including users logging into the system or by occupancy sensors such as motion, radar, and proximity sensors. Occupancy sensors are envisaged to be powered devices located in the health care service area (e.g., examination room, procedure room) and interface to the gateway/hub.

In some instances, users may provide an office schedule into the system and power states are adjusted based on this schedule (e.g., when an appointment is included for a time period on the schedule). The office schedule may indicate times when clinicians are working in the health care facility. Similar power adjustments may be controlled based on shifts when clinicians are active as indicated by the schedule.

Some instances may include microphones coupled with a speech detection system. The speech detection system may identify a key word to activate one or more device (e.g., adjust power state to an active/ready mode). In some implementations, a user action such as pushing a button or system usage factors such as user presence, may be used to wake up the device from a sleep mode.

In some instances power states may be adjusted by ML algorithms running on the hub/gateway and/or cloud. For example, historic patterns of usage may be analyzed to develop a model of power state activity that may be used to control one or more devices.

Features may also be included for harvesting energy using plurality of sources to increase smart lock operation life. In some instances uses piezo transducers interfaced to buttons or electromagnetic induction from lock actuator or drawer/door open and close action or wireless energy from RF sources to harvest energy.

The latch and door sensors included the system may include sensors to read the status of both the latch and door/drawer at all times. This capability enables workflow execution and also is used to detect tamper detection.

FIGS. 13A and 13B depict a remote smart lock reader module configured to unlock a securable container, according to various aspects of the subject technology. FIG. 14 depicts the remote smart lock reader module added to existing cabinet doors and/or existing cabinet drawers for controlled security. In the depicted example, a smart lock reader module may be implemented as a mobile device that contains a PCBA, NFC reader, Multi Colored LEDs, Common Batteries, mounting features, e-ink display, biometric reader, audio buzzer, LED light pipe, barcode, snap-on cover in order to access the batteries.

Figure 15:
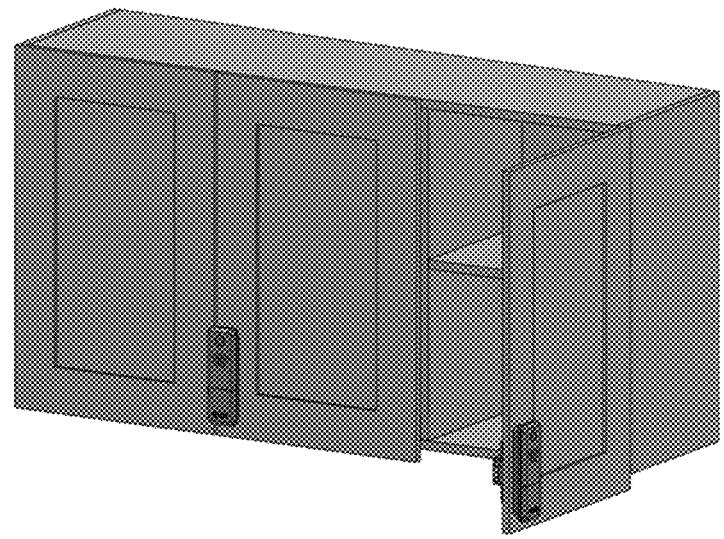
FIG. 15 depicts the smart lock reader module mounted on the external surface of a door or drawer using existing handle mounting holes, according to various aspects of the subject technology.
Figure 16:
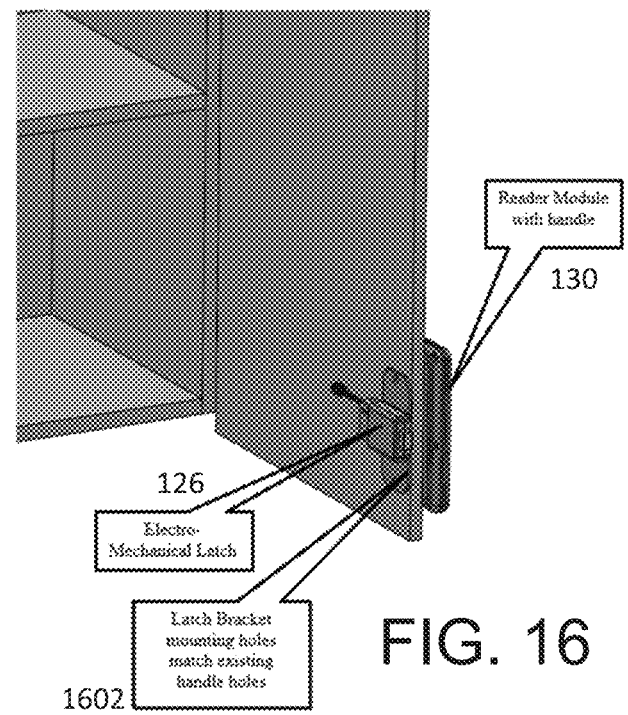
FIG. 16 depicts an electromechanical latch mounted to an interior surface of the door or drawer using a bracket, according to various aspects of the subject technology.

FIG. 15 depicts the smart lock reader module mounted on the external surface of a door or drawer using existing handle mounting holes, according to various aspects of the subject technology. FIG. 16 depicts an electromechanical latch 126 mounted to an interior surface of the door or drawer using a bracket 1602, according to various aspects of the subject technology. The electromechanical latch is operably connected to the smart lock reader module 130A, which may electronically control the latch. The shape of the housing allows the user to grip the smart lock and use it has a door or drawer handle.

The screws that mount the bracket pass through the door or drawer and thread into the outer housing. When the batteries expire, the latch remains in the locked position and the batteries are replaced to continue operation. The LEDs indicate location. Audio indicator can alert an open door or drawer. A sensor is used to determine if the door(s) are in the closed or open position. A sensor is used to determine if the latch is locked or unlocked.

Figure 17:
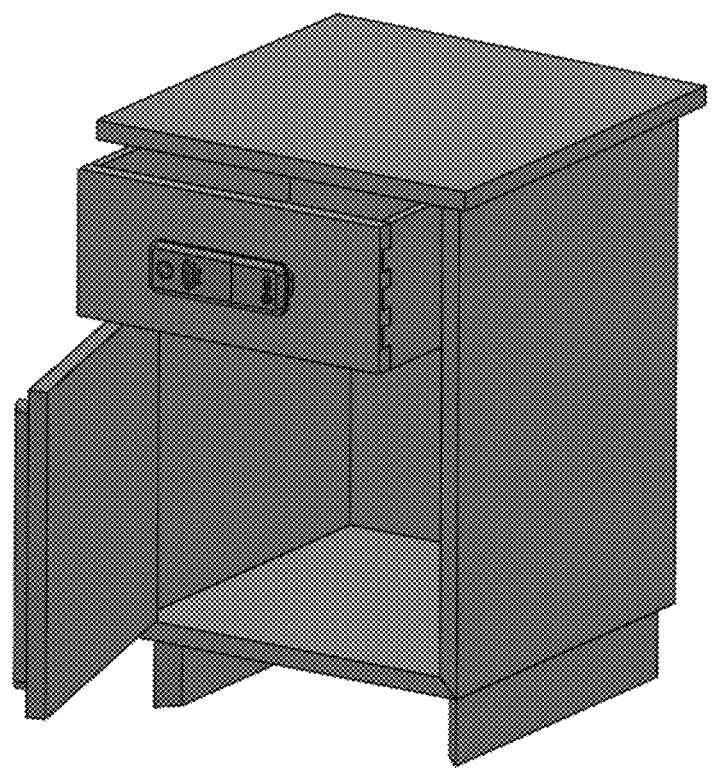
FIG. 17 depicts an example smart lock mounted to a cabinet drawer, according to various aspects of the subject technology.

The smart lock can communicate wirelessly to other devices. The smart lock units can have overlapping features, interlocks and to prevent diversion and indicate tamper evidence. FIG. 17 depicts an example smart lock mounted to a cabinet drawer, according to various aspects of the subject technology.

Secure Modular Bin Array

Another aspect of the disclosure relates to a slimline smart bin array system and methods, which enables safe and secured medication management solution with a focus on optimizing the existing user space and resources ("slimline bin" or "slimline"). According to various implementations, the disclosed system includes configurable smart bins (different sizes), wireless connectivity, and an enclosure to hold the array of bins securely on a wall. The system and method may also include a plurality of user interfaces, along with actuator that unlocks the slimline bin with a secured authorization from a server. The system and method may further implement a machine learning (ML) inference and data analytics to optimize power consumption on the slimline bin based on its awareness of spatial context.

In healthcare settings, there is a need for space & cost optimized enterprise secured medication storage and dispensing solutions. Some solutions use an automated dispensing cabinet (ADC) to control medications. ADC are expensive and take up a significant space. Existing user space such as drawers, cabinets and carts may be used to store and dispense medications. However, drawbacks include a lack of security, poor traceability of the medications, and a very manual process which utilizes more nurses or care giver resources. The disclosed solution includes a slimline with smart bin array transforms the underutilized or unutilized user wall space into a highly optimized enterprise medication management space.

Systems and methods for highly optimized medication storage and dispensing in healthcare settings are disclosed. The systems and methods may include a wall mounted slimline smart bin array system with configurable wirelessly connected smart bins (e.g., in different sizes), a plurality of user interfaces, a server authorized actuator lock, and may include location tracking, and may enable an enterprise solution for inventory tracking.

The disclosed system may include a processor, memory, input/output device, environmental sensor, tamper detection and wireless interface.

Other features may include one or more of the following: E-ink display, microphone, buzzer and multicolor LED for user interface; identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present the current state of the workflow; drive circuitry for piezo electric buzzer to provide audio feedback to the user; microphone interface circuitry for the user to provide wakeup words and or voice prompts; actuator latch drive circuitry and latch state read back methods; memory interface to store state and statistics of slimline bin status; sensor interface to monitor tamper, environmental condition & content sensing; and crypto and secure element interface to safely store public/private keys.

The disclosed system architecture may optimize an existing user space with a wall mounted slimline enclosure and configurable smart bins with wireless connectivity. In some implementations, a slimline enclosure and bin may be placed on a countertop.

In some implementations, the disclosed system architecture may include a latch and electronics to drive the latch as part of the bin. In some implementations, both the latch and electronics may be part of slimline enclosure.

In some implementations, the disclosed system architecture may include a bin that tilts open giving user access to medication and in other implementation bin pops open as a drawer.

In some implementations, the disclosed system architecture may automatically determine a plurality of user authorization methods. The user may then select one of the determined authorization methods to unlock the slimline bin.

An authentication method that securely transmits the user identity to the server and gets authorization to unlock the slimline bin is also disclosed. In some implementations, the system may include, and the authentication method may use, contactless smart card and in other implementations it could use barcode, biometric identification, ECG based wearable device or a mobile phone. In some implementations, the authentication method may include remote authentication. For example, if the user loses their badge or smart phone, a super user can provide remote authentication.

In some implementations, the systems and/or methods may utilize a sensor interface to automatically identify the quantity of contents in the slimline bin and tamper detection of slimline bin or enclosure. For example, the method may include monitoring for tamper detection on slimline enclosure attached to wall (e.g., using one or more sensors), and the slimline bin attached to enclosure, in real time using optics or electromagnetic sensing. In some implementations, the system and/or method includes a sensor interface such as load cell, optics with a led & photodiode, acoustics or RF to sense the quantity of content inside the bin.

A method by which an audible sound indicates user actions such as presenting badge to the slimline or when an actuator command is been executed is also disclosed. In some implementations, the system may include, and the method may use, a piezo beeper with different tones to indicate different actions.

According to various implementations, the system may include communication architecture (CA), which may use plurality of PAN protocols such as (802.15.4/BLE) to talk to the remote device. Accordingly, the disclosed system and/or method may use the CA to achieve one or more of the following features: beacon for asset tracking; real time and offline mode support.

In some implementations, the disclosed slimline bin (e.g., using CA) may bypass hospital IT, thereby reducing implementation time (e.g., implementing a drop ship model based on PAN protocol support).

The system and/or method implementing communication architecture (CA) may support an offline mode. When a network connection to the field hub or gateway is lost the disclosed slimline bin(s) may still allow the user to continue with their action, and the system may store and forward the actions when the network is restored.

In some implementations, the slimline bin(s) have the ability to broadcast beacons to a remote host, with the medication information for asset tracking. In some implementations, users can also read the beacons using a mobile device such as a phone or tablet.

In some implementations, the disclosed system and/or methods may include power architecture that utilizes disposable batteries or, in other implementations, the power architecture may implement rechargeable battery or a supercapacitor as an energy source for each bin. In some implementations, the power architecture (PA) may require one high capacity energy source to power the entire slimline bin array. For different implementations of high capacity energy source (PoE, battery, external power supply) and its interface using wired or docking connector see attached slides and docs.

In some implementations, a slimline bin array may be connected to an external power supply, the external power supply may directly power the slimline bin, or may charge the battery on the bin or enclosure. In some implementations, the disclosed system and method may include power architecture that uses wireless power transfer to access the slimline smart bin.

A method for charging the system using a plurality of wireless energy sources is also disclosed. In some implementations, a near field (such as NFC, Qi, Resonant and inductive) or far field (such as WiFi, UHF) wireless power transfer are used as energy source to access the slimline bin.

In some implementations, a multiplexed wireless charging scheme may be used to charge the secure storage solution. In some implementations, only one storage location may be accessed at a given time inside a slimline.

In some implementations, guided lights or mechanical features are used to dock the secured storage space for wireless charging.

A method for conserving power in battery operated devices based on system factors and user preference is disclosed. In some implementations, the method may include placing devices in low power states (ranging from system off state to various levels of sleep state) and waking up the devices periodically (wake up period) to enable radio communications, and checking in with a gateway/hub for updates or to perform transactions.

The low power state and wake up period may be configured by the gateway/hub for devices based on system usage factors and user preferences.

In some implementations, the system may include, and the method may include using, environmental sensors such as occupancy sensors. In some implementations, the system and/or method may use microphone with key word activation, user action by pushing a button or system usage factors such as user presence, office schedule to wake up the device from deep sleep mode.

A method for energy harvesting using plurality of sources to increase slimline smart bin operation life is also disclosed.

In some implementations, electromagnetic induction from lock actuator action or wireless energy from RF sources may be used to harvest energy.

In some implementations, the e-ink of the user interface of the device may display medication name, dosage and expire date. In other implementations, icons such as loading dock or in transit may be displayed to show the current status of associated medication that is been tracked.

In some implementations, the multicolor LED user interface may act as a glanceable status indicator. For example, the LED color, flash pattern and intensity may indicate different status based on user accessing the secure storage location and workflow.

Example 1: During medication loading workflow the led lighting can guide the user to the medication at a glance.

Example 2: If the medication in the slimline bin expired the LED can flash red.

Example 3: During medication audit the system may guide by lighting the LED's so the user can identify the med easily.

Example 4: If the battery level lower than threshold led can flash.

Figure 18:
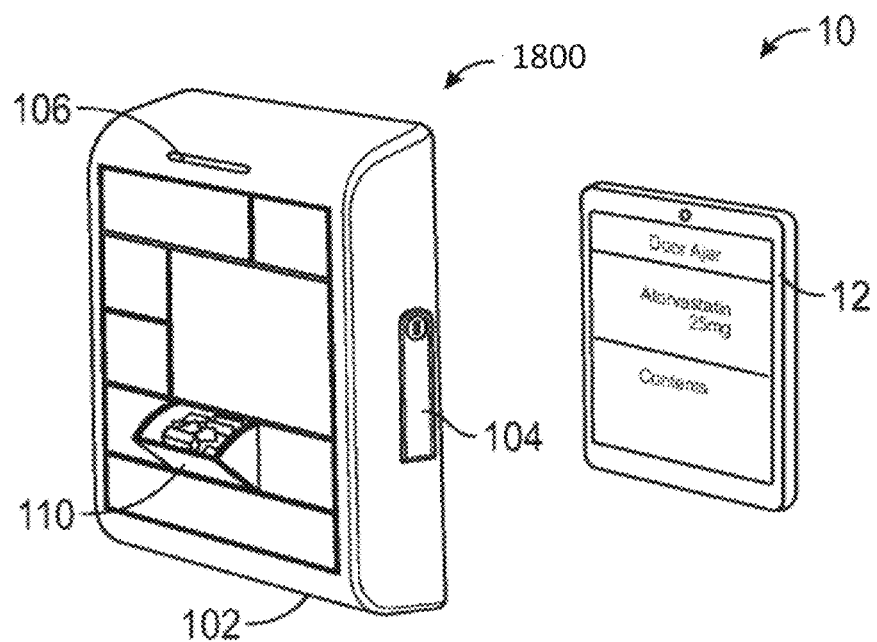
FIG. 18 depicts an array of secure modular bin assemblies for secure item storage and retrieval, according to various aspects of the subject technology.

FIG. 18 depicts an array of secure modular bin assemblies for secure item storage and retrieval, according to various aspects of the subject technology. The bin array 1800 may be placed on the counter top or wall mounted. The assembly array may may include storage bins 110 that may be created by connecting bin subassemblies. The bin assemblies may come in different sizes and may be arranged to create the bin array. In the depicted example, the bin array assembly 1800 can wirelessly communicate with a control panel 12. The control panel 12 can be used to select or identify medication within a medication management system. The control panel 12 can identify a bin 110 containing a desired medication, as well as information regarding the medication. Optionally, the control panel 12 can be used for authentication purposes.

As described previously, the slimline smart bin array system includes configurable smart bins that may be of different sizes, interconnected with each other to form a single unit. A slimline bin may be placed and used anywhere the storage and retrieval of items are needed such as a med-room, caregiver station, and/or patient's bedside.

A wall mounted unit may be locked to the wall by mechanical means 102. A key or electro-mechanical latch 104 may be used to unlock the slimline from the wall. Releasing the unit from the wall gives the user the access to the rear of the unit. A manual release mechanism may be accessible from the rear of the unit. The manual release mechanism may include a color-coded lever that the users uses to unlock all storage bins. All storage units may be unlocked simultaneously using the manual release mechanism, and the user may be given immediate access to all contents.

The slimline assembly may also be placed on a shelf or counter. Also, the unit may be mounted on the wall to keep counter top space clear. The slimline may be configured to use an electrical wall outlet to power units. The slimline assembly may be operated by common batteries.

The slimline assembly may communicate wirelessly to other devices 12. Each bin can contain an e-ink display. The display may indicate information about its contents. Each bin subassembly may have a barcode located on its front face.

The bin subassemblies may all have overlapping features and interlocks to prevent diversion. The unit may be designed to indicate the attempt to divert. For example, material may be deformable such that, when diversion occurs, the material is deformed showing tamper evidence. In some implementations, the bin hook may break and leave a piece in the latch making it unusable thereby indicating a break-in.

The slimline may be used in a refrigerated environment. The material and components may be used at lower temperatures.

Figure 19A:
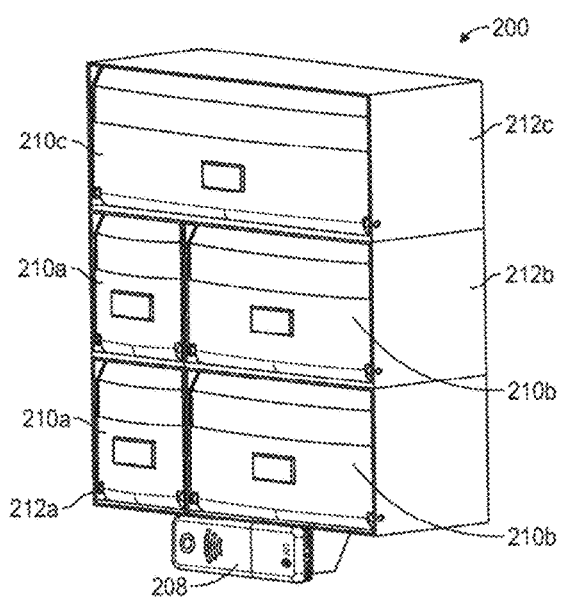
FIGS. 19A and 19B depict a slimline bin assembly with different size bin subassemblies configured for mounting on a wall, according to various aspects of the subject technology.
Figure 19B:
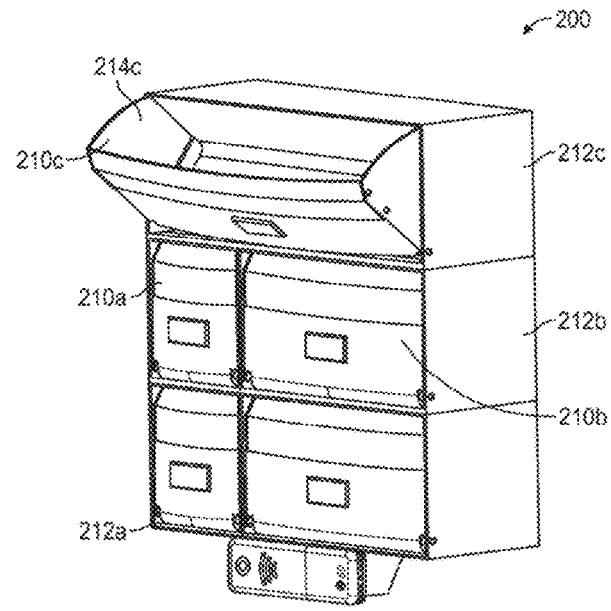
Figure 20:
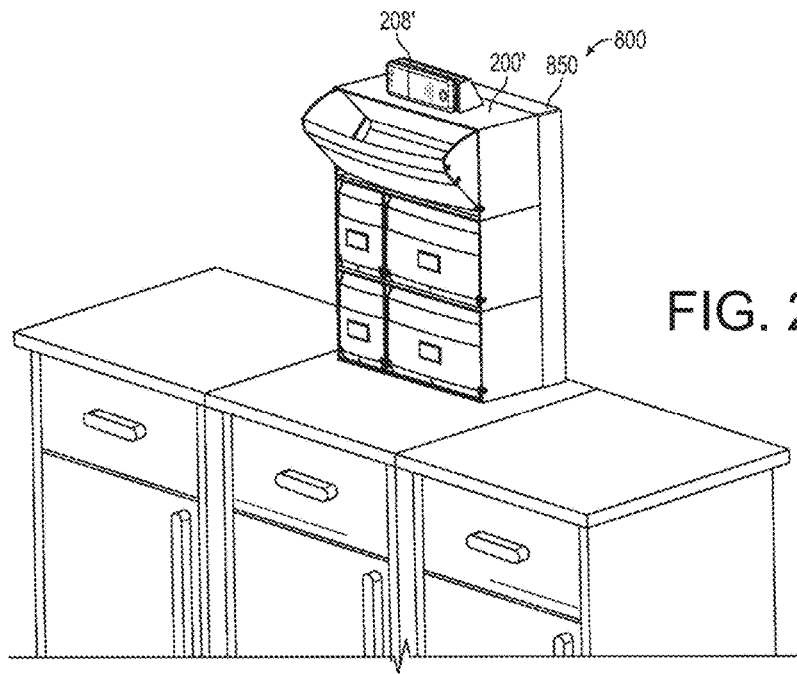
FIG. 20 depicts the bin array placed on a counter top, according to various aspects of the subject technology.

FIGS. 19A and 19B depict a wall-mounted slimline bin assembly with an integrated smartcard reader, according to various aspects of the subject technology. In the depicted example the assembly is created by connecting together different size bin subassemblies 210 (e.g., bins 120). The different size bins 210 may be custom arranged in any pattern. The connection features and hardware 850 to connect the bins are at the rear of the unit. FIG. 20 depicts the bin array placed on a counter top, according to various aspects of the subject technology. In the depicted implementation, the smartcard reader 208' is relocated to the top of the assembly.

As depicted in FIGS. 19A and 19B, the smartcard badge reader may be used for controlled security. The slimline may be accessed using the card reader. Additionally or in the alternative, the bin assembly and/or the smartcard badge reader may be integrated with or accessed using a PC, tablet computer, smartphone, barcode reader. A biometric reader may be part of the bin assembly and/or implemented as the reader, and used for controlled security.

Figure 21:
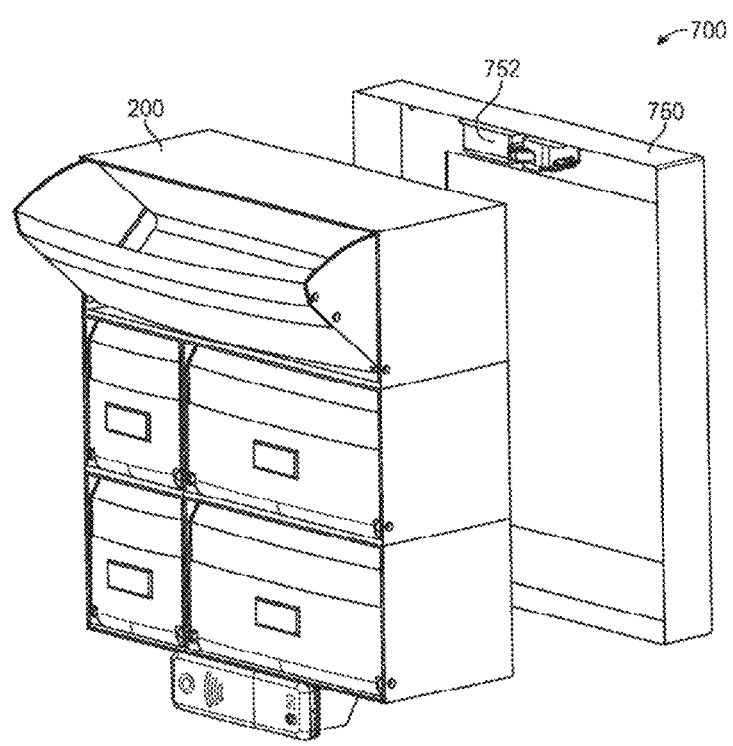
FIG. 21 depicts an example slimline bin assembly mounted to a wall using a mechanical support bracket, according to various aspects of the subject technology.

FIG. 21 depicts an example slimline bin assembly mounted to a wall using a mechanical support bracket 750, according to various aspects of the subject technology. According to various implementations, a wall mounted unit may be locked to the wall by mechanical means. A key or electro-mechanical latch 752 may be used to unlock the assembly from the wall.

In some implementations, the bin subassemblies may may include a storage bin, outer housing, latch, PCBA, battery, cabling, and bin latch hook, spring, window, barcode and features that would indicate tamper evidence. The width of the bin subassemblies may be single wide (1×), double wide (2×) or triple wide (3×). The bin subassemblies may share the same components and geometry except for the width. The outer housing may include features to mount latch, PCBA, LEDs, and battery. Also, features to pivot the storage bin and stops that limit bin rotation. The Outer Housing also may include mounting features that interface with other outer frames (e.g., in order to create a slimline module assembly).

Figure 22:
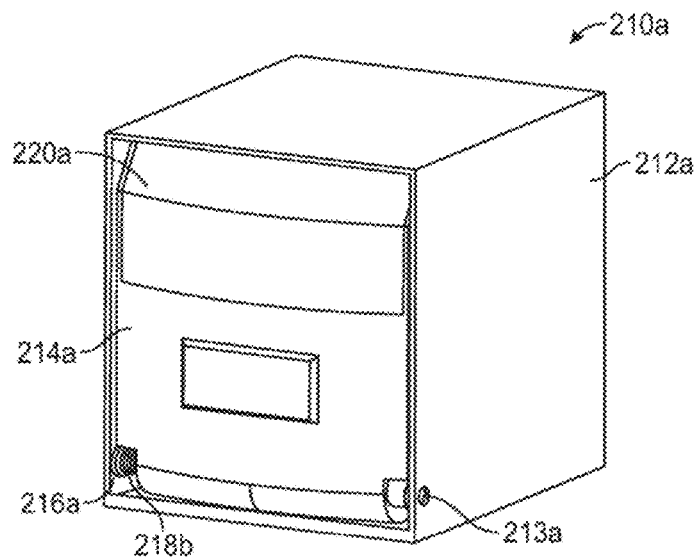
FIG. 22 depicts an example single-width storage bin with a pivoting storage bin, according to various aspects of the subject technology.
Figure 23:
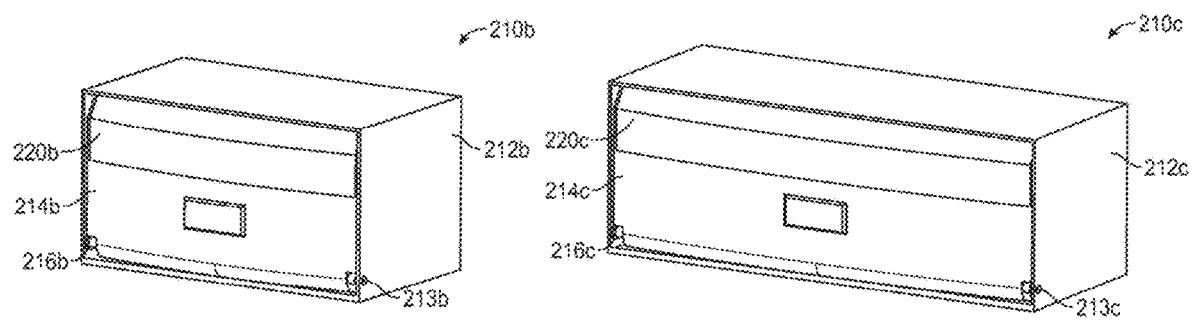
FIG. 23 depicts a double-width and triple-width storage assemblies with pivoting storage bins, according to various aspects of the subject technology.

FIG. 22 depicts an example single-width storage bin 210a with with a pivoting storage bin, according to various aspects of the subject technology. FIG. 23 depicts a double-width and triple-width storage assemblies with pivoting storage bins, according to various aspects of the subject technology. The storage bin may include features to mount a bin hook (that interfaces with the latch), mounting features for a window and spring mounting. The latch may operate from common batteries. It also contains sensors that can interface with indicating open/close status. The latch may include an on-board memory to digitally store content/location information. The latch may be part of the storage bin subassembly. The storage bin may be connected to the outer housing 212a via its pivot feature 216. Spring loaded and locked by latch, when released the storage bin pivots forward allowing the access to its stock. The user may be indicated which bin to access when one of the slimline bins pivot forward for item removal.

FIG. 24 depicts an example outer housing of a bin assembly with an electro-mechanical latch 228a, PCBA 222a, and battery 224a, according to various aspects of the subject technology. In such implementations, the PCBA may be communicated via a wire and operate the latch 228a.

FIGS. 25A and 25B depict cut-away views of an example disclosed storage bin, including a hook 226a that interfaces with the disclosed electro-mechanical latch, according to various aspects of the subject technology. The (tipping) storage bin, when manually being closed, may pivot rearward and the hook passes through an arc and interfaces with the latch. In its locked position, the outer housing protects access to the contents of the storage bin. The storage bin may may include a spring-loaded pivoting feature. The front of the storage bin may include a window. The window may be clear or translucent. The translucent window may be configured to let a user know that the bin contains items but mask the wordings on item labels. The tipping outward of the storage bin allows for the easy retrieval of its contents. The access opening at the max tip angle leaves the user an unobstructed access path to its contents.

Figure 26:
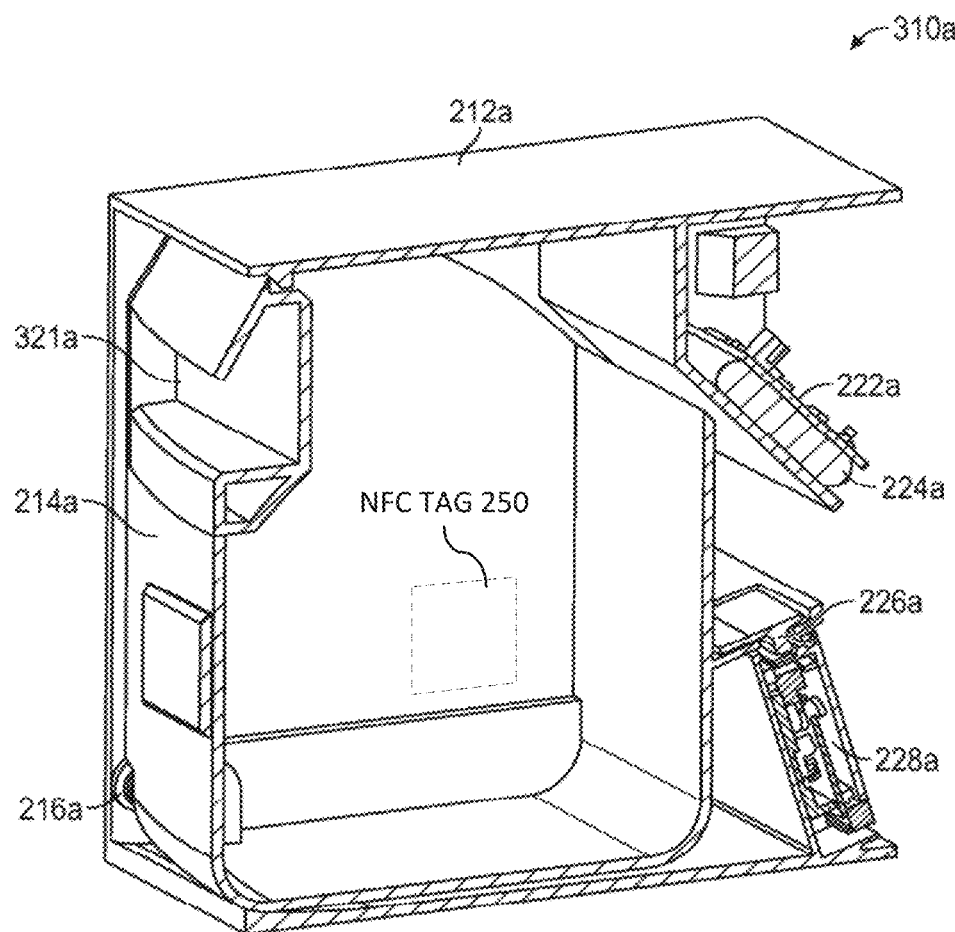
FIG. 26 depicts a cut-away view of an example storage bin with a handle feature, according to various aspects of the subject technology.

FIG. 26 depicts a cut-away view of an example storage bin with a handle feature 321a, according to various aspects of the subject technology. The handle feature may be used with a storage bin without a pivot spring. Additionally or in the alternative, the storage bin may include a window feature. Furthermore, some implementations may also include multi-colored LED lights. The system may activate the LEDs, and the window could become a light pipe and illuminate the LEDs output. The illuminated window would alert the user with the location of the contents. As will be described further, a near field communication (NFC) tag 250 may be affixed to a side of the bin 120, or rear of the bin 120.

In implementations according to FIG. 26, one or more of the following features may be included: (1) The storage bin incorporates a handle. (2) The storage bin pulls out horizontally from the outer housing and eventually hits a stop feature. Once the storage bin the bin hits the stop feature it may be tilted downward and come to a stop. The angled bin allows for easy retrieval of items. (3) The storage bin may be spring loaded and "pop" outward on latch release indicating location of item. (4) The storage bin can use LED's for item location.

Figure 27:
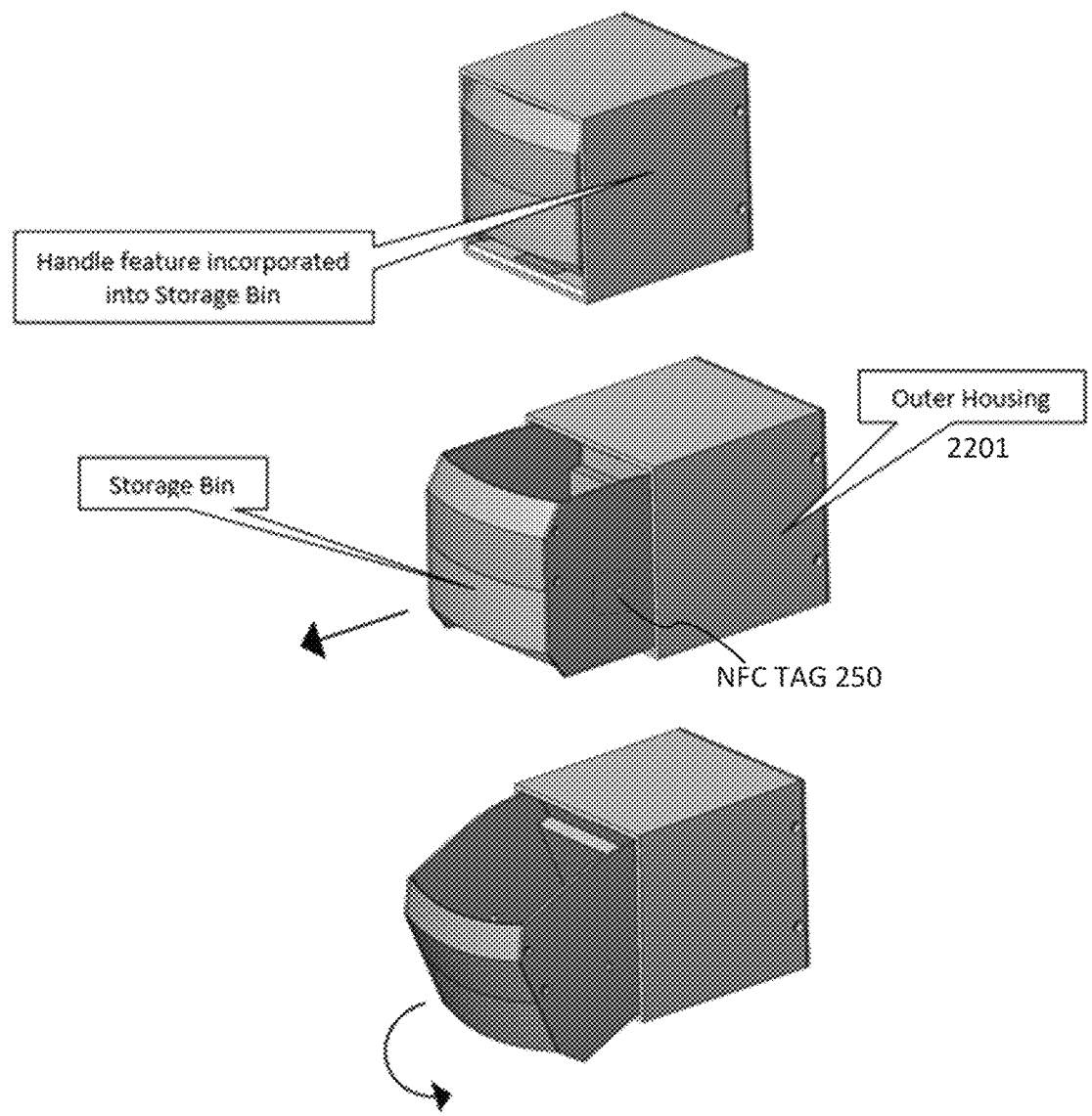
FIG. 27 depicts an example slimline storage assembly, according to various aspects of the subject technology.

FIG. 27 depicts an example slimline storage assembly, according to various aspects of the subject technology. In the depicted example, a handle feature is incorporated into the storage bin. The storage bin may be pulled from the housing, and may tilt and/or rotate after reaching a predetermined location. In implementations according to FIG. 3-10, one or more of the following features may be included: (1) The boarder frame contains the storage bin locking mechanism. (2) The bin subassembly frame does not contain a latch. (3) The storage bin has features that interact with the latch. (4) The bin locking is done by a latching mechanism that is part of the boarder frame. (5) The boarder frame latch can consists of horizontal rotating rod and a vertical rotating rod. A near field communication (NFC) tag 250 is depicted as being affixed to a side of the bin 210.

Figure 28A:
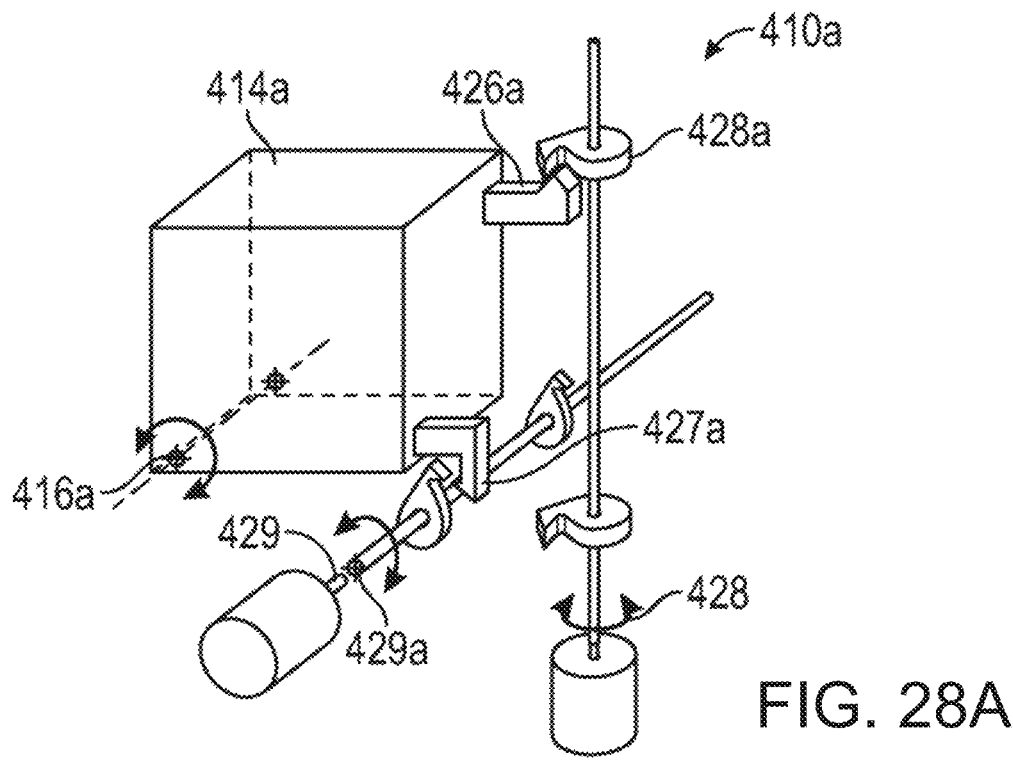
FIGS. 28A and 28B depict an example storage bin latching mechanism, according to various aspects of the subject technology.
Figure 28B:
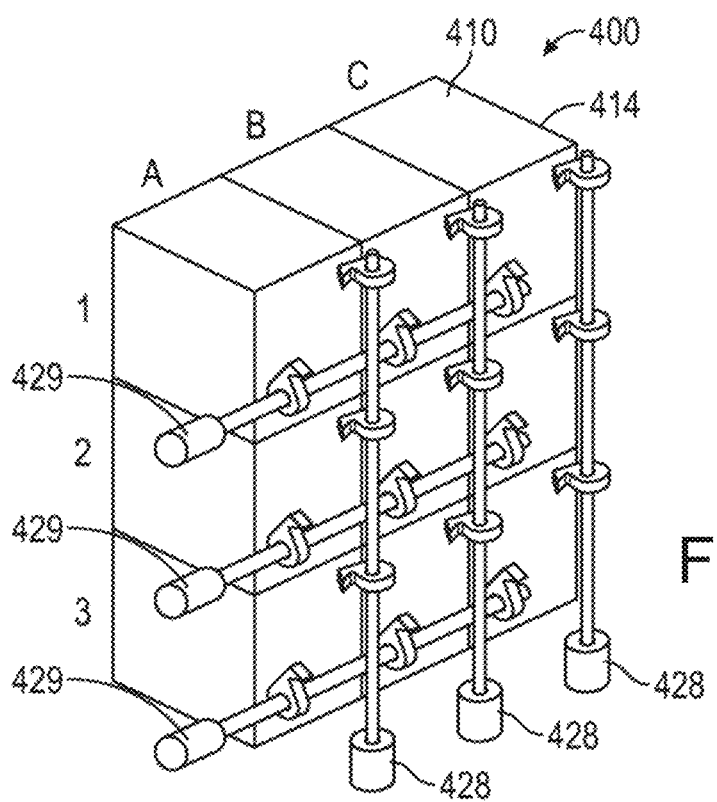

FIGS. 28A and 28B depict an example storage bin latching mechanism, according to various aspects of the subject technology. In the depicted example of FIG. 28A, rods 428, 429 are implemented within the housing 212, and have latch features 428a on them the allow it to lock and unlock the storage bin. In this regard each bin may have one or more corresponding latches 426a, 427a to engage latches 428a. In this regard, the bin may be released when both the horizontal and vertical latches are in the open position.

As depicted in FIG. 28B, the boarder frame assembly may include three horizontal rod assemblies 429 and three vertical rod assemblies 429. Each rod assembly may include three latches 428a and an actuator. A 3×3 array may include nine horizontal latches, nine vertical latches and six actuators. With the depicted example, up to nine storage bins 400 may be independently unlocked with the horizontal and vertical rod assemblies arranged in an 3×3 array.

Figure 29:
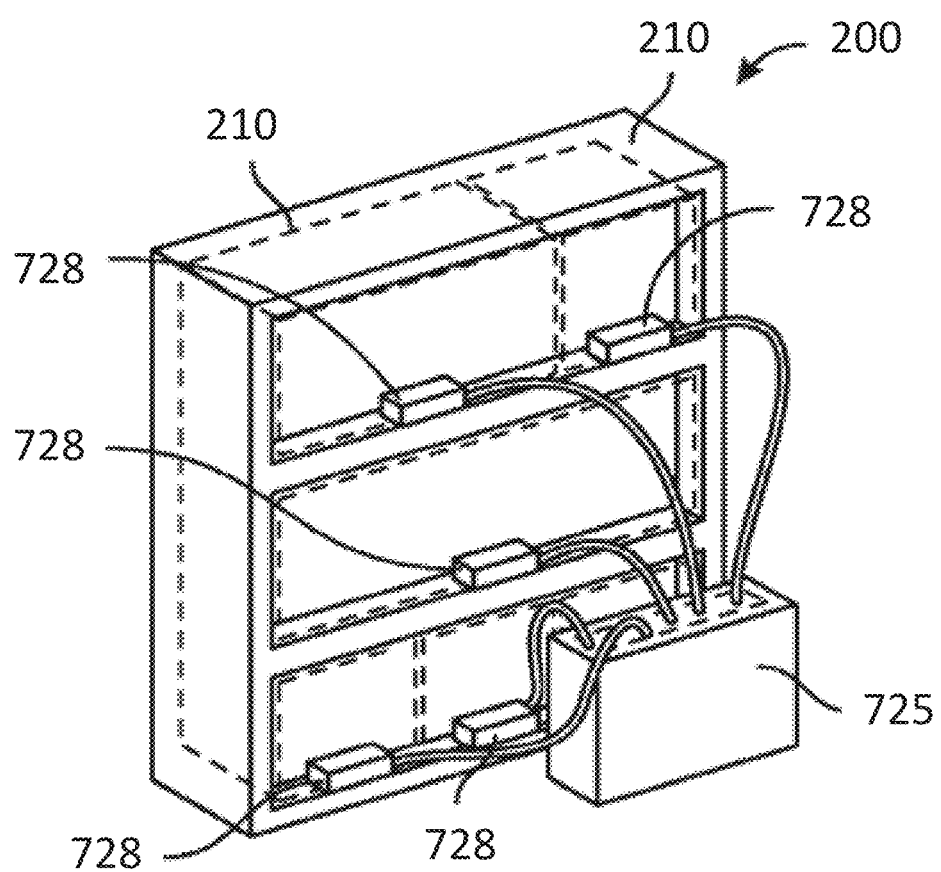
FIG. 29 depicts a rear view of an example slimline frame with a latch control module, according to various aspects of the subject technology.

FIG. 29 depicts a rear view of an example slimline frame 200 with a control module 725, according to various aspects of the subject technology. In implementations according to FIG. 29, one or more of the following features may be included: (1) The bin frame 200 contains the storage bin locking mechanism. (2) The bin subassembly frame 200 does not contain a latch. (3) The bin frame includes a latch controller module. The latch controller module has a connector ports to accommodate up to nine latches 126. The latch control module contains electronic hardware to operate up to nine latches independently. (4) Each latch 126 is positioned and mounted to the frame as needed to control its mating bin. (5) Each storage bin has at least one hook that interfaces with a corresponding latch. (6) Each latch is connected to the latch control module.

Additionally or in the alternative, bin assembly 200 may include a passive near field communication (NFC) antennae 528 for each bin 210 within assembly 200. Likewise, each bin may be configured with a passive NFC tag on a side or rear of the bin that, when the bin is loaded within the bin housing 212 of assembly 200, comes into communicable contact with a respective antennae 728. Control module 725 may be operably connected to a bus the within the bin housing via cabling or by wireless means, and the bus may be operably connected to each latch 126 and/or each NFC antennae. While control module 725 is depicted as a separate device from bin assembly 200, it is understood that control module 725 may be part or integral with bin assembly 200, or may be part of or integral with a smart device 130 associated with or linked to assembly 200. It is also understood that depicted diagram for antennae 728 may also be representative of a respective latch 126 or latch actuator.

Each bin may be associated with a unique identifier, which is stored by its respective NFC tag. The identifiers may be mapped to a particular bin specification (e.g., volume, height, etc.) and particular contents currently stored within the bin. For example, server 114 may keep track of the contents of each bin in a database. When a bin 210 is opened, control module 725, receiving the indication from the NFC tag via antennae 728, may send a signal to server 114 indicating that the module was opened, and may send a close signal with the status of the bin changes from open to closed.

Control module 725 may also send the bin location within the assembly together with the identifier of the bin. This way, if a clinician reconfigures the bins, server 114 will update the new configuration in memory. The stored configuration can then be used to provide an alert to the clinician should the clinician move a bin to an undesirable location, or rearrange the bin assembly in a manner not consistent with a healthcare organization's policy or predetermined rules. If the clinician using an IOT inventory tracker or other smart remote device to open a bin corresponding to a medicine, the server 114 may perform a check to determine which bin holds the requested medicine (e.g., by querying the control module 725), before opening the bin. If the clinician attempts to open the wrong bin, or attempts to place a bin in the wrong assembly location, the control module (via the assembly or smart device 130) may provide an audible and/or visual alert. Control module 725 may also lock a bin from being opened or being inserted into a bin location.

According to some implementations, control module 725 may provide power to the various components of an associated bin assembly 200, including to each bin 210 with the assembly. Power may be daisy chained from control module 725 to one bin location to another, and so on. Control module 725 also includes a central processing system or processor, such as that described with respect to FIG. 5. With reference to FIG. 12, control module 725 may act as a master hub, and operate all bins as slaves in a master/slave configuration. Such configuration may be by way of wired cables or by wireless connection (e.g., BLUETOOTH) between the control module and each bin.

With further reference to FIG. 29, bin assembly 200 may include a near field communication (NFC) antennae within the bin housing 212. An NFC tag may be affixed to a side of a first container 210, located within the housing. The NFC tag is configured to come into communicable contact with the NFC antennae when the first container is loaded into the bin housing. Control module 725 (or a similarly situated processor) may be configured to monitor various bin locations within the housing via corresponding NFC antennae, and detect, responsive to the bin being placed in or removed from the bin housing, a presence of a respective NFC tag via a signal received from the NFC antennae. The control module 725, responsive to the detecting, may then record an open or closed status of the first container responsive to an indication from the NFC tag/antennae that the first container was opened (e.g., removed from the housing) or closed.

In some implementations, the control module 725 is further configured to detect that a container was removed from a first bin location within the housing and inserted into a second bin location within the housing. In this regard, control module 725 may receive a first signal from a first NFC antennae associated with the first bin location. The first signal may include a unique identifier associated with the container and an identifier or location associated with the first bin location. The control module 725 may then receive a signal from a second NFC antennae associated with the second location, the second signal including the unique identifier of the container and an identifier or bin location associated with the second bin location. The control module 725 may then determine that the second location is not a proper location for the bin, for example, by querying a mapping table that maps medications (within the container) to known bin locations. The control module 725 is configured to provide (e.g., via display interface 164) an alert regarding the placement of the bin at the second location. For example, if the location is determined to not be a proper location then the alert may indicate for the user to remove the container and place it back at the first location or a more suitable location. If the second bin location is a correct location for the medication then the alert may indicate the transaction successfully completed.

According to various aspects, the control module is configured to receive a request from a mobile device to provide a medication, and determine a bin location within the bin housing of a container storing the medication. The request may originate form a mobile device associated with a clinician, or may be received via an associated interactive storage device interface 130 (e.g., display interface 164, button 161, or the like). The control module 725 is configured to determine whether the clinician or user associated with the request is authorized to access the container storing the medication, and to send, when the user is authorized to open the first container, a signal to the bin location to enable access to the container storing the medication from the first housing. The authorization may be based on predetermined authorization information stored within a memory of the control module 725, Connected Security Latch Another aspect of the disclosure relates to a wireless activated smart remote manager (waSRM) system and methods that enables secured access to refrigerated medication that already exist in user healthcare settings. This solution provides safe and secured medication management with a focus on optimizing the existing user space and resources. The disclosed system and/or device includes a wireless latch, display and an enclosure that mounts effortlessly to a refrigerator. The system and/or device also includes a plurality of user interfaces along with actuator that unlock the waSRM with a secured authorization from a server. Optionally, the disclosed system, device, and/or method may also implement a machine learning (ML) inference and data analytics to optimize power consumption on waSRM based on its awareness of spatial context.

In the realm of regulated products in healthcare settings there is a need for space & cost optimized enterprise secured medication storage and dispensing solutions. In prior art, one solution is to use a remote manager with wired interfaces to a med station and proprietary message to unlock a refrigerator. The limitations are lock's proximity to med station and take up a significant space. In other implementations there are wireless activated refrigerator lock with temperature sensor but lack user interface, restricts just peer to peer protocol and no support for internet of things (IoT) architecture and hence can't aggregate and provide insight on data using a field hub or gateway. The subject technology involving a waSRM transforms the user experience with lot more insight on its usage using analytics and supports star, mesh, broadcast mode in a highly optimized enterprise medication management space. To the best ability of our knowledge the systems and methods we proposed using waSRM is unique and enables all the shortcomings of the prior art.

A system, device, and method associated with highly optimized medication storage and dispensing solutions in healthcare settings is disclosed.

The solution includes a waSRM with plurality of user interfaces, server authorized actuator lock, location tracking, and enables enterprise solution for inventory tracking.

According to various implementations, the system and/or device includes a processor, memory, input/output device, environmental sensor, tamper detection mechanism, and wireless interface. Other features include one or more of the following: E-ink display, microphone, buzzer and multicolor LED for user interface; identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present the current state of the workflow; drive circuitry for piezo electric buzzer to provide audio feedback to the user; microphone interface circuitry for the user to provide wakeup words and or voice prompts; actuator latch drive circuitry and latch state read back methods; memory interface to store state and statistics of waSRM status; sensor interface to monitor tamper & environmental condition; and crypto and secure element interface to safely store public/private keys.

The disclosed system, device, and/or method may include an authentication system that automatically determines a plurality of user authorization methods. A user may then select one of the determined authorization methods to unlock the waSRM.

The disclosed system, device, and/or method may include a mechanism to securely transmit the user identity to the server and gets authorization to unlock the waSRM.

In some implementations, the authentication system may use contactless smart card. In some implementations, the authentication system may use a barcode, biometric identification, ECG based wearable device, or a mobile phone. The authentication method may include remote authentication. For example, if the user loses their badge or smart phone the super user can provide remote authentication.

The disclosed system, device, and/or method may include an optical or electromagnetic sensor interface that monitors for tamper detection on waSRM attached to refrigerator in real time.

The disclosed system, device, and/or method may include an environmental sensor interface system. In some implementations, the environmental sensor interface system may be capable of monitoring NIST traceable temperature sensors used for cold storage of vaccines.

In some implementations, the environmental sensor interface system may be capable of monitoring plurality of sensors including: temperature, humidity, vibration and acceleration of the waSRM.

The disclosed system, device, and/or method may include a mechanism by which an audible sound indicates user actions such as presenting badge to the waSRM or when an actuator command is been executed. In some implementations, the disclosed system, device, and/or method uses a piezo beeper with different tones to indicate different actions.

The disclosed system, device, and/or method may include a display user interface that functions as a glanceable status indicator and is configurable by the user. In some implementations, the display may provide detail information from the environmental sensors such as temperature and humidity.

Example 1: Display medication names and quantity that is been tracked.
Example 2: Display environmental sensor information inside and outside of the refrigerator.
Example 3: Display icons such as loading truck to indicate the status of the medication being tracked.
Example 4: Display battery level, network connectivity and status of the latch.

The disclosed system, device, and/or method may include a multicolor LED user interface. In some implementations, the LED user interface functions as a glanceable status indicator. The LED color, flash pattern and intensity may indicate different status based on user accessing the secure storage location and workflow.

Example 1: During medication loading workflow the led lighting can guide the user to the medication at a glance.
Example 2: If the medication in the slimline bin expired the LED can flash red.
Example 3: During medication audit the system may guide by lighting the LED's so the user can identify the med easily.
Example 4: If the battery level lower than threshold led can flash.

The disclosed system, device, and/or method may include a communication architecture (CA). In some implementations, the CA may be configured with a plurality of PAN protocols such as (802.15.4/BLE) to talk to a remote device. A method that utilizes the CA may include one or more of the following features: beacon for asset tracking; real time and offline mode support. In some implementations, the waSRM (e.g., using CA) may bypass hospital IT, thereby reducing implementation time (e.g., implementing a drop ship model based on PAN protocol support).

The system and/or method implementing communication architecture (CA) may support an offline mode. When a network connection to the field hub or gateway is lost the waSRM may still allow the user to continue with their action, and the system may store and forward the actions when the network is restored.

In some implementations, the waSRM is configured to broadcast beacons to the remote host with the medication information for asset tracking. In some implementations, users may also read the beacons using a mobile device such as a phone or tablet.

In some implementations, the waSRM may be configured as a companion device for devices placed inside the enclosure to bridge communications. Connected devices placed inside enclosures, such as refrigerators and metal cabinets, may have their radio signals attenuated and have difficulty communicating to hubs located further away. In these cases another device such as waSRM is used as companion device to enable reliable communication to the hub/gateway. smart bin when acting as a companion device may play two roles: (1) A slave role communicating to the hub; and (2) A master role communicating to the devices behind the enclosure. With brief reference to FIG. 12, This may create a multi-level network hierarchy in the network of devices all communicating back to the hub either directly or through another device.

In some implementations, the disclosed system and/or methods may include power architecture (PA) that utilizes disposable batteries or, in other implementations, the power architecture may implement rechargeable battery or a super-capacitor as an energy source for each waSRM.

The PA may use wireless power transfer to access the waSRM.

The system and/or device may be charged using one or more of a plurality of wireless energy sources. In some implementations, the PA is configured to utilize far field (such as WiFi, UHF) wireless power transfer are used as energy source to access the waSRM.

The disclosed system, device, and/or method may be configured to conserve power in battery operated devices based on system factors and user preference. A corresponding method may include placing devices in low power states (ranging from system off state to various levels of sleep state) and waking up the devices periodically (wake up period) to enable radio communications and to check in with a gateway/hub for updates or to perform transactions.

The low power state and wake up period may be configured by the gateway/hub for devices based on system usage factors and user preferences.

In some implementations, the system, device, and/or method uses environmental sensors such as occupancy sensors. In some implementations, the system, device, and/or method may use a microphone with key word activation or system usage factors such as office schedule to wake up the device from deep sleep mode.

In some implementations, the system, device, and/or method may be configured for energy harvesting using a plurality of sources to increase waSRM operation life. In some implementations, the system, device, and/or method may utilize electromagnetic induction from lock actuator action or wireless energy from RF sources to harvest energy.

Figures 31A, 31B:
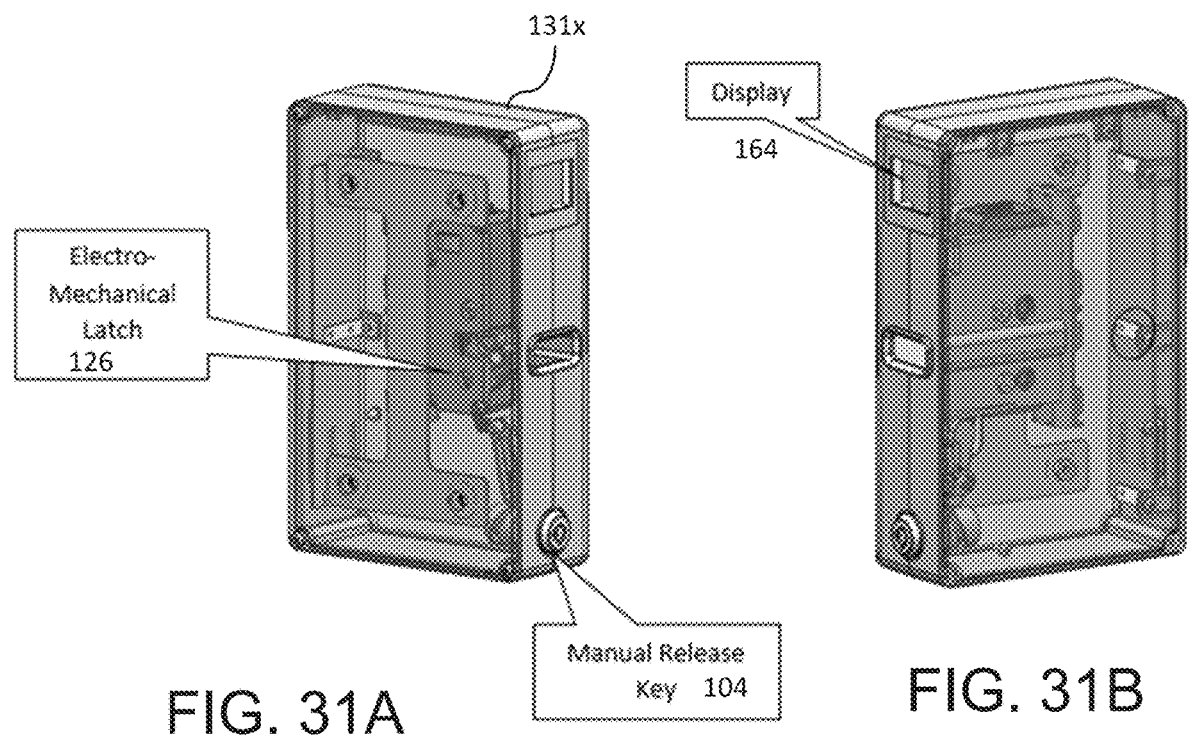
FIGS. 31A and 31B depict a cut-away view of an example IOT (Internet-of-things) smartlock reader module (SRM), according to various aspects of the subject technology.

FIGS. 31A and 31B depict a cut-away view of an example IOT (Internet-of-things) smartlock reader module (SRM) 130x, according to various aspects of the subject technology. According to some implementations, the disclosed IOT SRM includes a device that may be attached to a refrigerator. In this regard, the IOT SRM may incorporate an electro-mechanical lock 126 for secured access to the refrigerator. The IOT SRM may include an (e.g. e-ink) display 164, LED indicator, Temperature readout, and common batteries for ease of replacement. The IOT SRM may be configured to communicate wirelessly with other devices. The IOT SRM may include a manual release key 104 to release lock 126 by mechanical means (e.g., when power has been removed from the lock).

Figure 32:
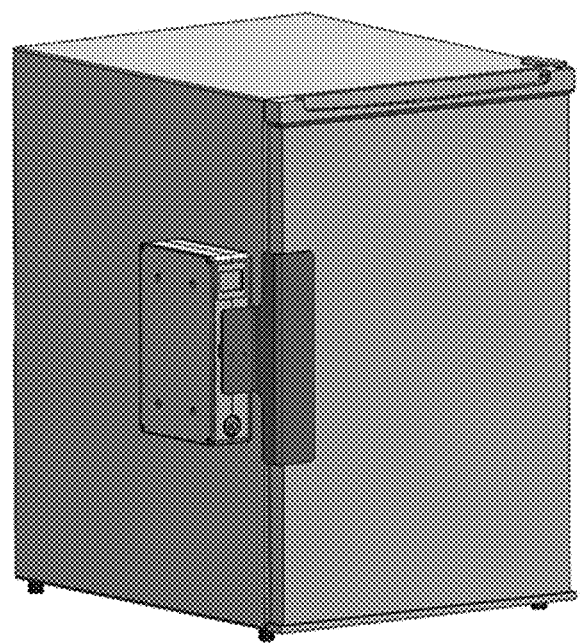
FIG. 32 depicts an example IOT SRM mounted on the exterior surface of a refrigerator, according to various aspects of the subject technology.

FIG. 32 depicts an example IOT SRM 131x mounted on the exterior surface of a refrigerator, according to various aspects of the subject technology. The refrigerator may include an off-the-shelf "dorm" style refrigerator for con-trolled security. The IOT SRM may include a repeater to aid in the communication of IOT devices within the refrigerator. The IOT SRM may include overlapping features, interlocks and materials to indicate tamper evidence. The IOT SRM may include a key lock for manual release.

Modular Dispensing Bin

Another aspect of the disclosure relates to a smart bin or tote system, device, and/or corresponding methods which provide secure access and transport of items including medications and supplies (the "smart bin"). The disclosed smart bin may be configured for controlled, non-controlled, refrigerated and non-refrigerated items in both acute and non-acute health care settings. The disclosed smart bin may be configurable to allow the different authentication requirements of both regulatory bodies and hospitals.

The disclosed smart bin may provided in multiple sizes to accommodate different items and is stackable to optimize storage locations. The disclosed smart bin may be a wireless connected device connected to a gateway and connects to an enterprise level application. According to various implementations, users may authenticate using remote authentication methods (such as a tablet or standalone authentication modules) and a secure and traceable access is provided to the smart bin. The disclosed smart bin may include one or more user interfaces that include multi-color LEDs, E-Ink display, buttons and audible buzzers. In some implementations, smart bin may include a machine learning (ML) inference and data analytics to optimize power consumption on smart bin based on its awareness of usage context. In some implementations, the disclosed system, device, and/or method includes a handheld device or mobile application that can scan multicolor led and identify system status during manufacturing or field.

The disclosed smart bin and related systems and method may include implementation of an enterprise level solution that provides traceability and inventory tracking of item in a multitude of use cases.

Secured storage for controlled medications involve off the shelf keyed or combination lock bins that are placed on countertops or inside cabinets and drawers. Users may use the same key or combination numbers to access medication. However, these solutions are not traceable as to who accessed the medication. Additionally, tracking of inventory in non-acute care settings is performed manually and is not accurate. The smart bin described herein provide secure traceable access to these medications. The smart bin may also provide a display screen to indicate quantity and buttons for users to increment or decrement quantities, and may be connected to an enterprise level medication management software which enables end to end inventory management.

According to some implementations, the disclosed smart bin is configured to be placed inside refrigerators to provide secure access and inventory management to refrigerated medications. In some implementations, the smart bin may be configured as a mobile device which may be used for secure transport of medication. A secure bin may be used on its own or placed inside the previously described smart tote for secure transport. The smart bin may be configured to beacon its unique ID over the wireless interface and is used for location tracking of the bins.

In some implementations, the smart bin is a stationary device located in medication rooms, at a bedside of the patient, or at other care locations. In some implementations, the disclosed smart bin is located inside refrigerators. The disclosed smart bin may be configured to be hardened to withstand refrigerated environments. In some implementations, the disclosed smart bin is a mobile device used for secure transport of items. The disclosed smart bin may include a plurality of user interfaces which enables an enterprise solution for securing one or more items and guide the loading of the item(s).

FIG. 33 depicts example subsystems of the disclosed smart bin system and/or device, according to various aspects of the subject technology. As depicted in FIG. 33, the disclosed system and/or device may include an E-ink user interface. In some implementations, the user interface may display status of the disclosed smart bin using icons such as battery level, network connectivity, and/or status of the latch and door. In some implementations, the user interface may display alerts such as expired medication, below par, tamper detection etc. In some implementations, the user interface may display information collected from an environmental sensor. For example, the user interface may display information such as temperature of medication, monitor tamper evidence sensor signal, humidity, shock and vibration over time. In some implementations, the user interface may display item name and item quantity. In some implementations, the contents of the display is configurable by the user.

In some implementations, the user interface may include one or more buttons that are used to decrement and increment quantity of the item. In some implementations, the user interface may function as a glanceable status indicator. For example, LED color, flash pattern and intensity may indicate different status based on user accessing the secure storage location and workflow.

Example 1: During medication loading workflow the led lighting may guide the user to the medication at a glance.

Example 2: If the medications being secured by the Smart bin has expired the LED can flash red.

Example 3: During medication audit the system may guide by lighting the LED's so the user can identify the med easily.

Example 4: If the battery level lower than threshold led can flash in low intensity Example 5: Led color and flash pattern to indicate authorized user unlocked the latch.

In some implementations, the disclosed smart bin system may include or embody a handheld device that may scan the led color, intensity and flash pattern, and identify its status during manufacturing or in field. In some implementations, the Smart bin system may include inspection equipment or a mobile application, and/or an optical reading device to read the multicolor visual indicator and to obtain the failure modes and conditions on smart bin.

Access to disclosed smart bin may be authenticated via remote authentication. For example, users can enter credentials at tablet or PC or use a standalone authentication module to gain access to the disclosed smart bin. If a user loses their badge or smart phone the super user may provide remote authentication.

In some implementations, the disclosed smart bin may be configured to produce an audible sound that indicates user actions such as when an actuator command is been executed. In some implementations, the disclosed smart bin includes a piezo beeper is used with different tones to indicate different actions.

In some implementations, the disclosed smart bin may include an environmental sensor interface system. In some implementations the environmental sensor interface system may be capable of monitoring NIST traceable temperature sensors used for cold storage of vaccines. In some implementations the environmental sensor interface system may be capable of monitoring plurality of sensors including: temperature, humidity, vibration, orientation and acceleration of the smart bin.

In some implementations, the disclosed smart bin may include a tamper detection system. The tamper detection system may be configured to detect tamper via the foregoing environmental sensors and/or additional sensors (e.g. optical and electromagnetic sensors) located on the latch, drawer and lid which detect unauthorized access to contents of smart bin.

In some implementations, the disclosed smart bin may include a content detection subsystem. The content detection subsystem may utilize the sensor interface to automatically identify the quantity of contents inside smart bin. In some implementations, the disclosed smart bin may support a sensor interface such as load cell, optics with a led & photodiode, acoustics or RF to sense the quantity of content inside the bin. In some implementations, the disclosed smart bin may support a coarse level of identification used for auto-detection PAR levels.

In some implementations, the disclosed smart bin may include a power subsystem. The power subsystem may be configured to support a distributed architecture where each bin has its own wireless communication interface and power source. In some implementations, the power subsystem may include a central architecture where multiple bins are wired to a single controller. The controller may provide wireless communications and power source for multiple bins. Accordingly, the number of wireless communication interfaces, electronics and power sources may be reduced, which may be desirable in cases where many bins are co-located (i.e. multiple bins stacked inside one cabinet).

The disclosed system, device, and/or method may include a communication architecture (CA). In some implementations, the CA may be configured with a plurality of PAN protocols such as (802.15.4/BLE) to talk to a remote device. A method that utilizes the CA may include one or more of the following features: beacon for asset tracking; real time and offline mode support; environmental sensor and tamper detection monitoring; content identification and inventory tracking. In some implementations, the smart bin (e.g., using CA) may bypass hospital IT, thereby reducing implementation time (e.g., implementing a drop ship model based on PAN protocol support).

According to various implementations, the disclosed smart bin may be configured to act as a companion device for devices placed inside the enclosure to bridge communications. Connected devices placed inside enclosures, such as refrigerators and metal cabinets, may have their radio signals attenuated and have difficulty communicating to hubs located further away. Accordingly, the smart bin may be used as companion device to enable reliable communication to a hub/gateway. The smart bin when acting as a companion device may play two roles: (1) A slave role communicating to the hub; and (2) A master role communicating to the devices behind the enclosure. As discussed previously with regard to FIG. 12, the foregoing creates a multi-level network hierarchy in the network of devices all communicating back to the hub either directly or through another device.

In some implementations, the disclosed smart bin system and/or device may include a power architecture (PA). In some implementations, the PA may be configured to use disposable batteries or, in some implementations, rechargeable batteries.

In some implementations, the disclosed smart bin system, device, and/or corresponding method may be configured for energy harvesting using a plurality of sources to increase smart bin operation life. In some implementations, the smart bin may be configured with piezo transducers interfaced to buttons or electromagnetic induction from lock actuator or drawer/door open and close action or wireless energy from RF sources to harvest energy. In some implementations, the disclosed smart bin system and/or device may include a power management subsystem that conserves power in battery operated devices based on system factors and user preference. In this regard, a method for conserving power may include placing devices in various low power states to wake up periodically (wake up period) and enable radio communications and check in with a gateway/hub for updates or to perform transactions. Power saving states may adjust device responsiveness vs power savings. The low power states and wake up period may be configured by the gateway/hub for devices based on system usage factors and user preferences.

In some implementations, power states may be adjusted based on user presence, if users are present the devices are placed in more responsive states in anticipation of the system being used. If users are not present the devices may be put in less responsive states, to maximize power savings In some implementations, the smart bin may detect user presence. For example, smart bin may detect users logging into the system, by occupancy sensors such as motion, radar, and proximity sensors. Occupancy sensors may be configured to be powered devices located in the med room area and interface to the gateway/hub.

In some implementations, the disclosed system may receive user input of office schedule into, and power states may be adjusted based on this schedule. In some implementations, the disclosed system may use microphones with key word activation to wake up the device from deep sleep mode. In some implementations, power states may be adjusted by ML algorithms running on the hub/gateway and/or cloud.

In some implementations, the disclosed smart bin system and/or device may include a monitoring subsystem. The monitoring subsystem may include or interface with sensors which monitor health of the device including the environmental sensors, and/or additional sensors monitoring the operation of the device such as currents on motors, voltages, temperatures of critical components, etc.

In some implementations, the monitoring subsystem may be configured to transmit collected data to the hub/gateway/cloud for analytics. In some implementations, the disclosed smart bin system and/or device may include a secure transport subsystem. The secure transport subsystem may be configured to facilitate use of the smart bin for secure transport of item.

In some implementations, the smart bin may be used as a standalone transport or may be placed inside a tote (e.g., the disclosed smart tote). In some implementations, the smart bin may be configured to play a beacon role, advertising its unique ID, so it may be identified and located for asset tracking by hubs or mobile devices. Unique ID and configuration information, including contents of the smart bin, may be stored locally on the device in a non-volatile memory. This information may also be made available to an online database (e.g., for retrieval view an online network).

In some implementations, the secure transport smart bin may be configured to be tracked by hubs which are in areas of interest. As the device moves. hubs located in the area may be able to read the beacon and identify the device. For example, hubs may be placed in areas of interest such as shipping and receiving, staging areas, hallways etc. In some implementations, the beacons may be read by mobile devices. In some implementations, the secure transport smart bin may be queried directly by hubs or mobile devices for additional information such as contents of smart bin, destination, battery level, environmental sensors etc. Alternatively, the mobile device and/or hubs may be network connected and may be configured to retrieve information about the smart bin from a network database using the beacons unique ID.

In some implementations, the secure transport smart bin may be configure to implement wireless signal characteristics, which may be used to locate and guide a user to the smart bin modules. This may be desirable where a specific device needs to be located and a user may be guided to the unit they are looking for.

Figure 34:
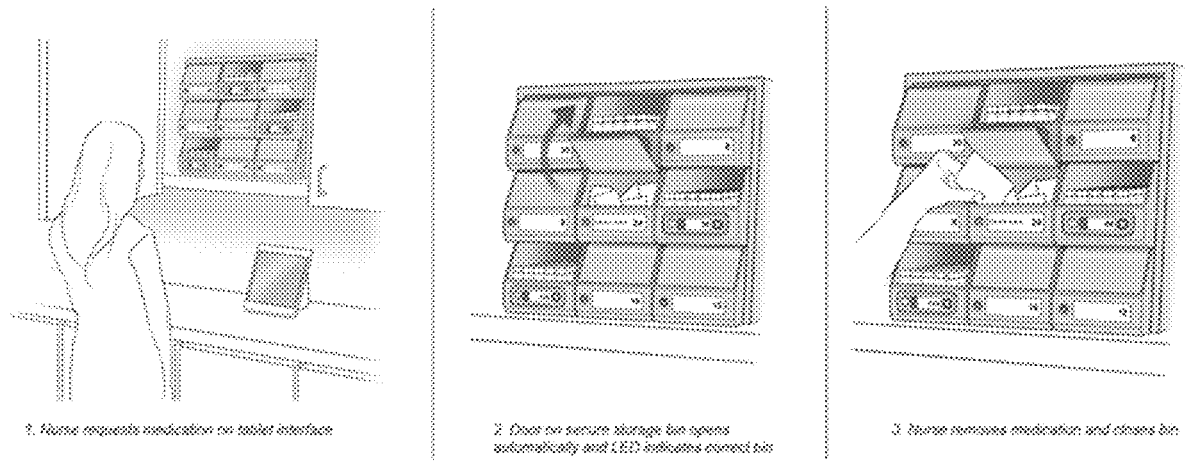
FIG. 34 depicts an example smart bin system for dispensing items, according to various aspects of the subject technology.

FIG. 34 depicts an example smart bin system for dispensing items, according to various aspects of the subject technology. In various implementations, the smart bin system and/or device(s) may be configured as a singular, stackable and secure modular bin, for item storage and retrieval. A smart bin may communicate wirelessly with other devices, and may be configured to record user access.

The smart bin system and/or device(s) may be configured to withstand a refrigerated environment, and may include material and components that may be used at cold temperatures. The smart bin system and/or device(s) may be placed in a refrigerator and may support optional sensors for temperature and humidity. The smart bin system and/or device(s) may be configured with overlapping features and interlocks to prevent diversion. The smart bin system and/or device(s) may be designed to indicate an user's attempt to divert. The smart bin system and/or device(s) may be formed of or include material that may be deformed showing taper evidence. Additionally or in the alternative, the smart bin system and/or device(s) may include a hook configured to break and leave a piece in the latch making it unusable thereby indicating a break-in.

Figure 35A:
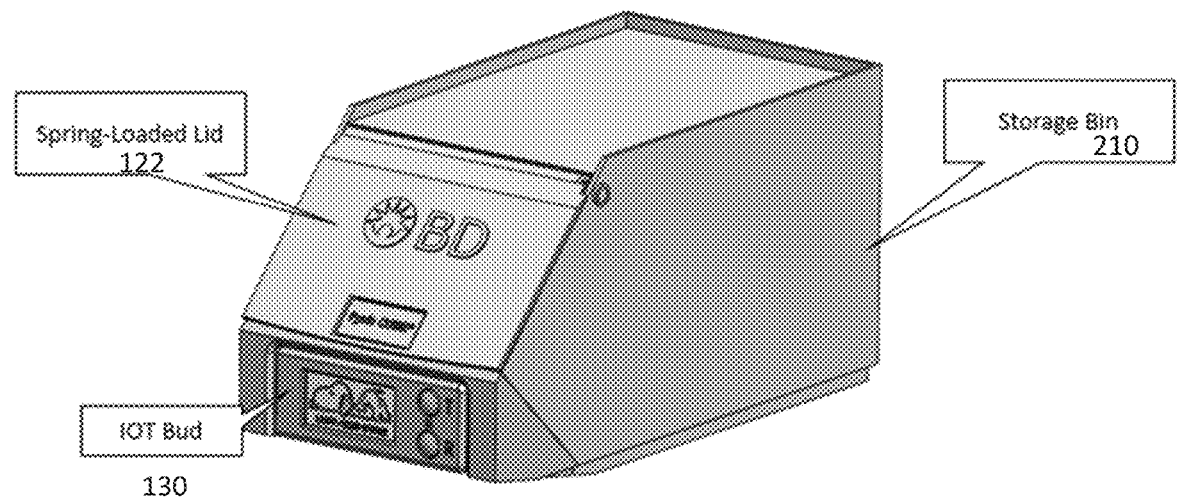
FIGS. 35A, 35B, and 35C depict example stackable smart bins for dispensing items, according to various aspects of the subject technology.
Figure 35B:
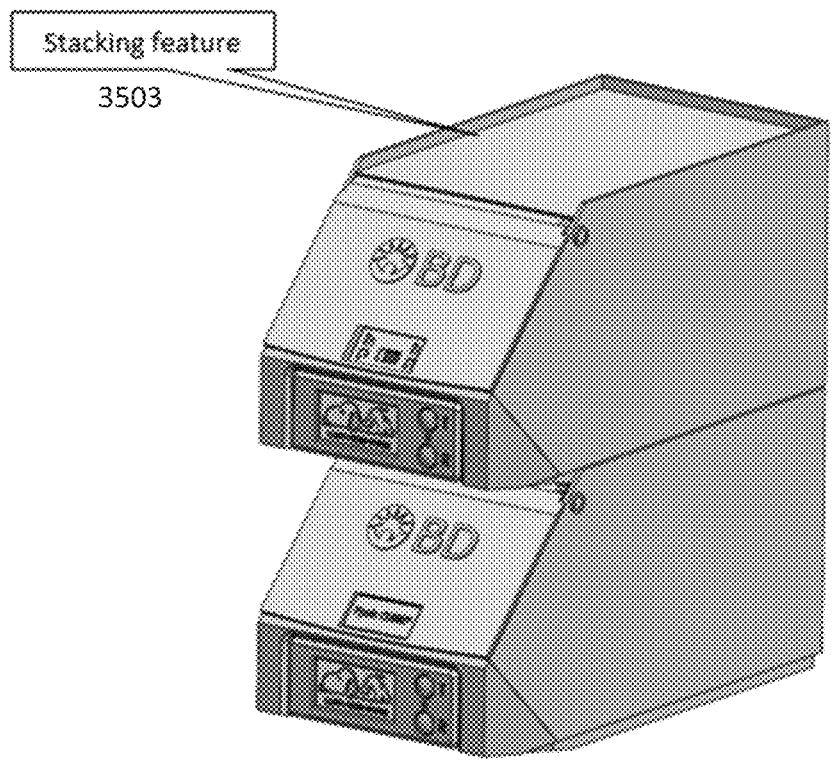
Figure 35C:
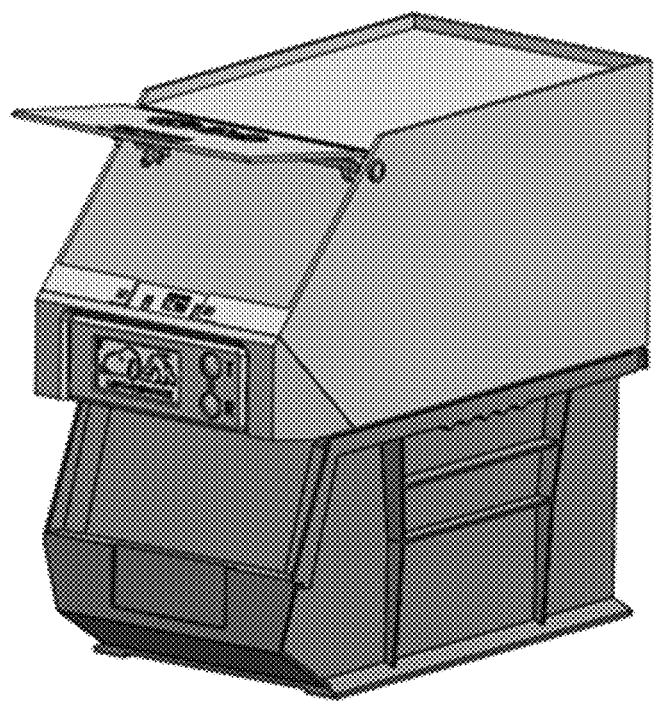

FIGS. 35A, 35B, and 35C depict example stackable smart bins 210 for dispensing items, according to various aspects of the subject technology. According to some implementations, the smart bin system and/or device(s) may be fully enclosed. The smart bin system and/or device(s) may include the five-sided container storage bin, electro-mechanical latch, PCBA, battery, spring-loaded lid 122, one or more LEDs, IOT inventory tracker 130, features that allow it for stacking, features that allow it to be mounted to securing frame, barcode, load cell for take-by-weight. An IOT inventory tracker may be configured to communicate wirelessly to the smart bin system and/or device electronics.

As depicted in FIGS. 35B and 35C, the smart bin may be stacked. The size of the smart bin storage container may be configured (e.g., with a stacking feature 3503) to be stacked on top of or to interconnect with current bin suppliers (see FIG. 35C). As depicted in the figures, smart bin may be stacked on top of each other and may be stacked with current storage bins. The smart bin may be designed to indicate the attempt to divert. The smart bin may include material that may be deformed showing taper evidence. The disclosed latch hook may break and leave a piece in the latch making it unusable thereby indicating a break-in.

Figure 36:
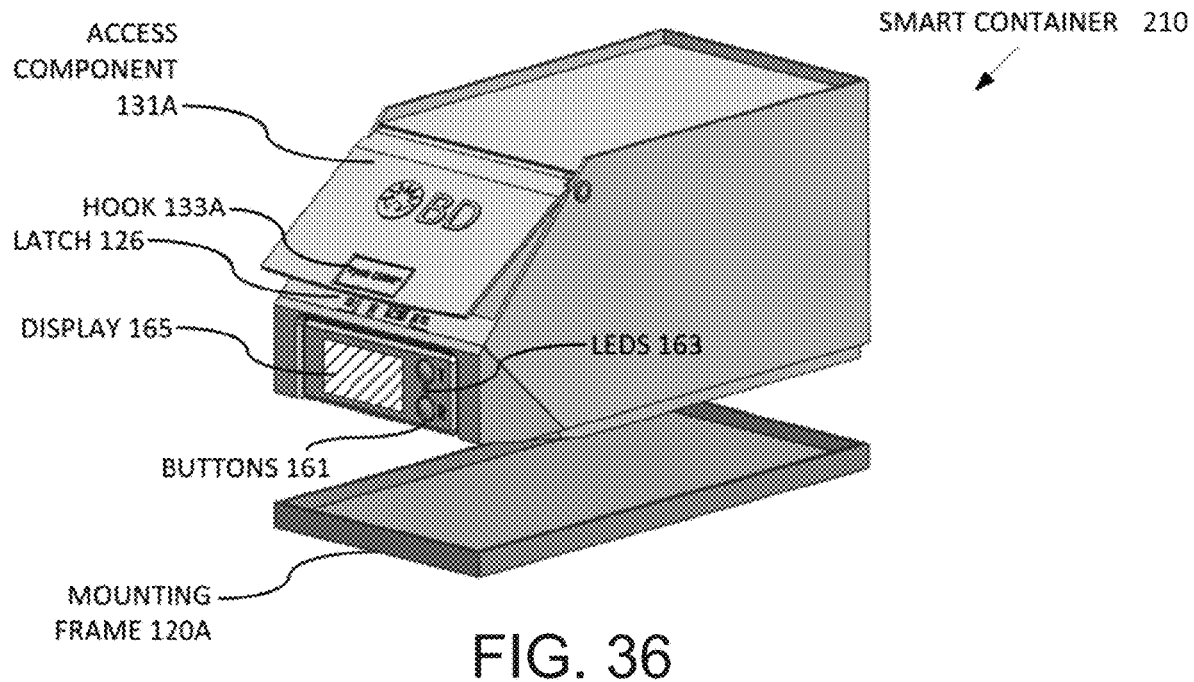
FIG. 36 depicts an example smart bin mechanically attached to an example securing frame, according to various aspects of the subject technology.

FIG. 36 depicts an example smart bin mechanically attached to an example securing frame, according to various aspects of the subject technology. A securing frame may be securely mounted to a counter, cabinet shelf or refrigerator shelf. The securing frame may interface with the smart bin storage bin features. The smart bin 210, 130 may be configured to be locked to the securing frame using a latch or key lock. Locking the smart bin to the securing frame may deter diversion and may indicate tamper evidence.

Figure 37:
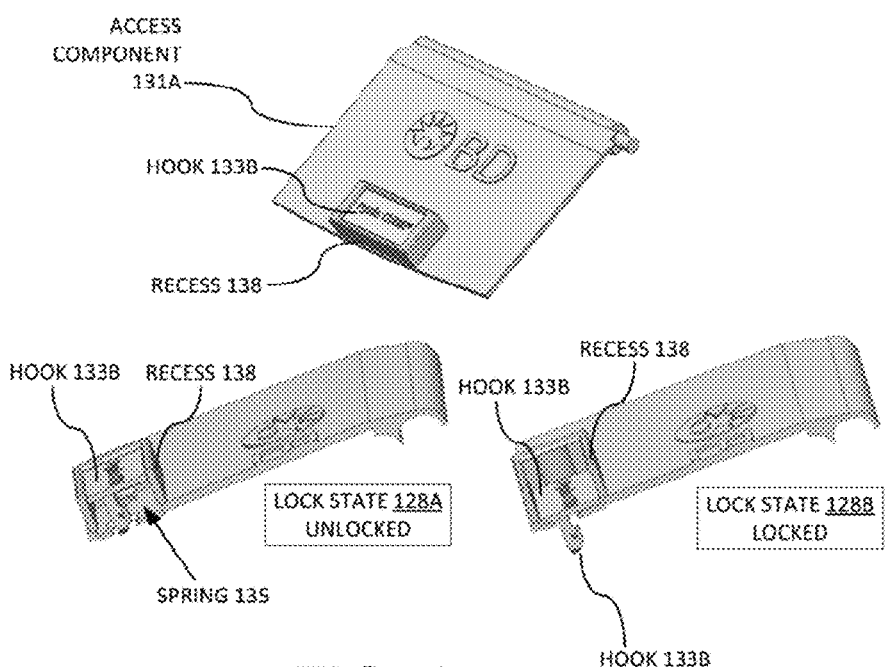
FIG. 37 depicts various examples of a smart bin lid, according to various aspects of the subject technology.

FIG. 37 depicts various examples of a smart bin lid, according to various aspects of the subject technology. In some implementations, the smart bin lid 122 may mount a hook part 133 that interfaces with the latch 126. The hook part 133 may be spring loaded and retract in order to create a clear path for the users hand to content access. The hook part may be used as a "button" do depress in order for it to engage the latch when the lid is closed.

Figure 38A:
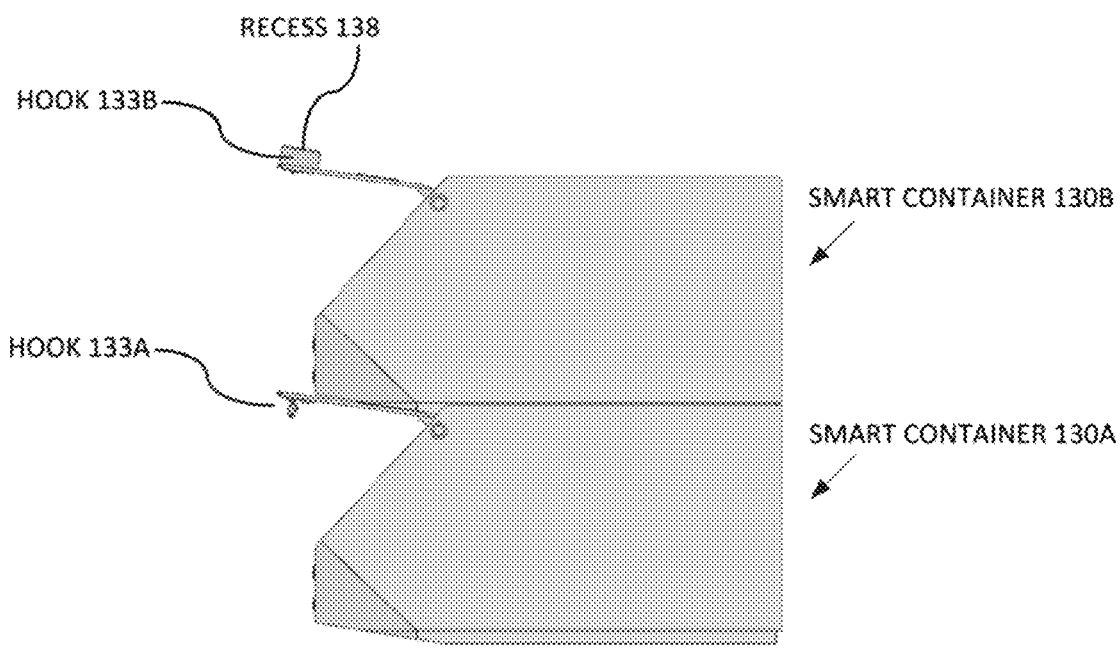
FIGS. 38A and 38B depict cut-away side views of example smart bins and corresponding lids, according to various aspects of the subject technology.
Figure 38B:
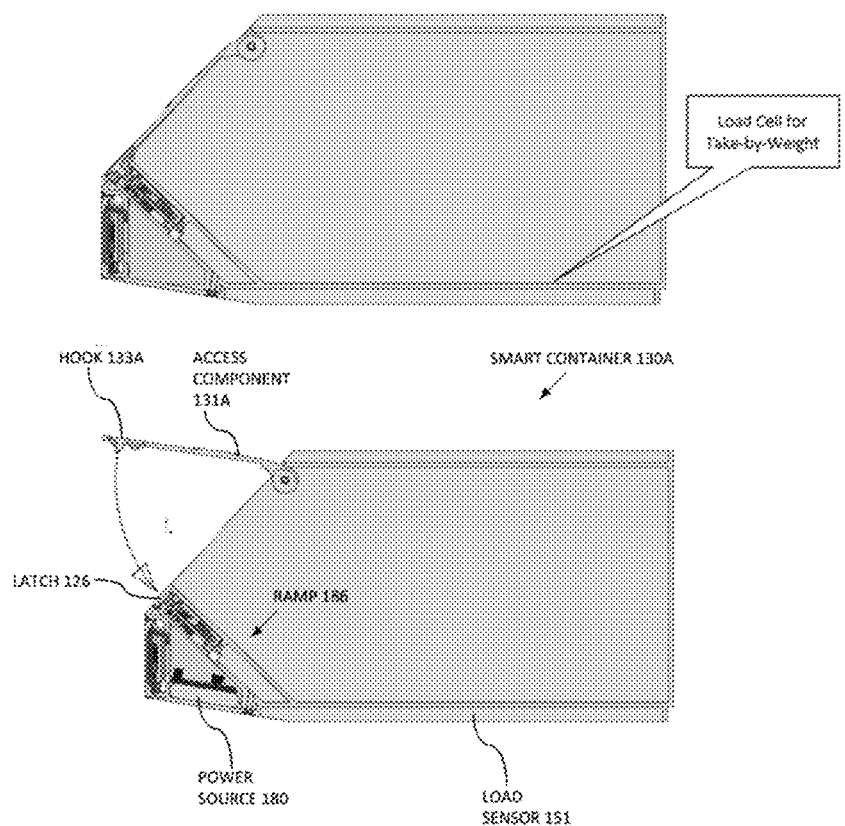

FIGS. 38A and 38B depict cut-away side views of example smart bins and corresponding lids, according to various aspects of the subject technology. FIG. 38A depicts an example difference between a push button retractable lid hook and a non-retractable lid hook. In the example figures, the lid of the smart bin pivots open and closed. Opening the lid provides access to the smart bin's contents. The lid may be spring loaded. In some implementations, the smart bin container may include an electro-mechanical latch. The latch may be battery operated. The battery may be recharged using an electrical wall outlet. The battery may easily be replaced. (See FIG. 38B.) The storage bin may include features on it to mount the latch. The storage bin may incorporate a ramp to help with the containment and removal of items.

FIG. 38B depicts cut-away side views of example smart bins and corresponding lids configured with a lid hook that engages with an electro-mechanical latch, according to various aspects of the subject technology. In addition to the foregoing lidded concept, the smart bin may be further adapted as follows: (1) In some implementations, the smart bin may include a pull-out Drawer that allows the user to easily retrieve and see the contents, and which aids a blind count workflow. (2) In some implementations, the smart bin may not include a lid, but instead include a lockable drawer. In these implementations, the smart bin may include an Outer Housing, Drawer, window, electro-mechanical latch, PCBA, battery, LEDs, spring, IOT inventory tracker, and/or asset tracking subsystem.

Figure 39A:
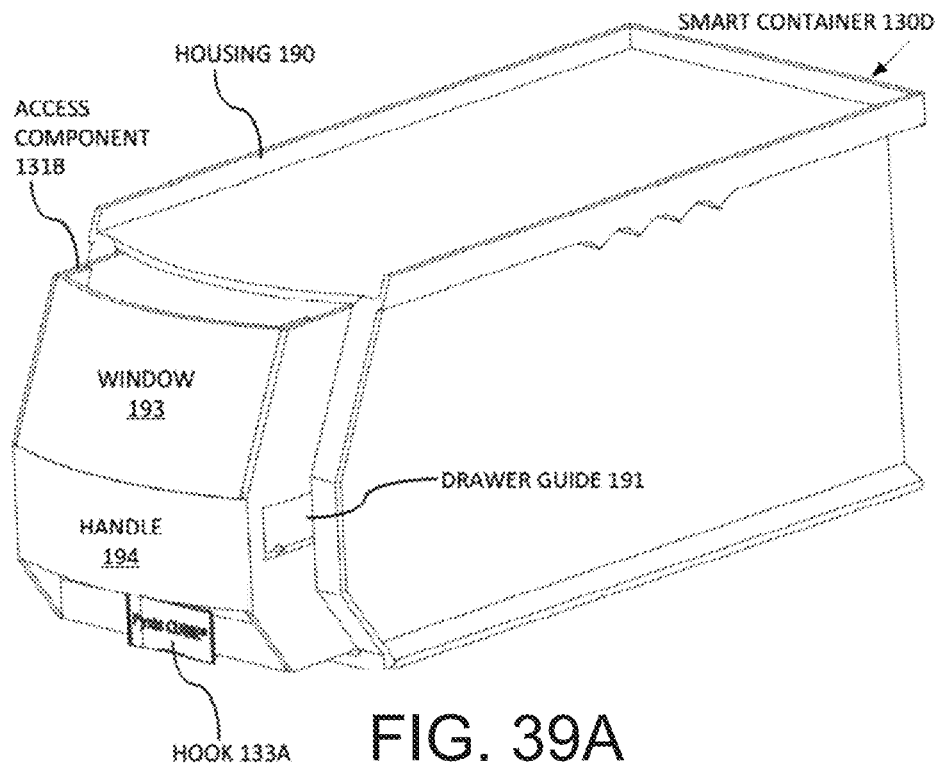
FIGS. 39A and 39B depict example smart bin drawers, according to various aspects of the subject technology.
Figure 39B:
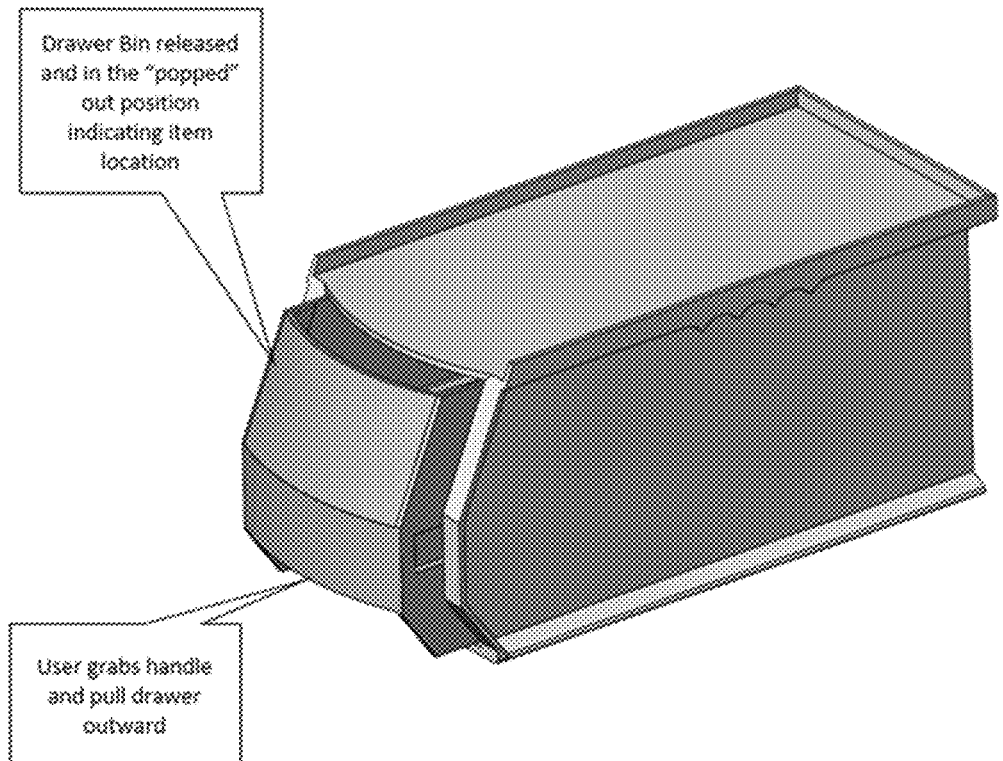

FIGS. 39A and 39B depict example smart bin drawers, according to various aspects of the subject technology. The smart bin may include a drawer base bin that resides in an outer housing. The smart bin may incorporate a handle. The smart bin may be configured to pull out horizontally from the outer housing and eventually hit a stop feature. Once the smart bin hits the stop feature it may be tilted downward. This drawer-based configuration of smart bin may allow for easy retrieval of items and visual accessibility for counting items. The smart bin may be spring loaded and "pop" outward on latch release indicating location of item (See FIG. 39B).

Figure 40A:
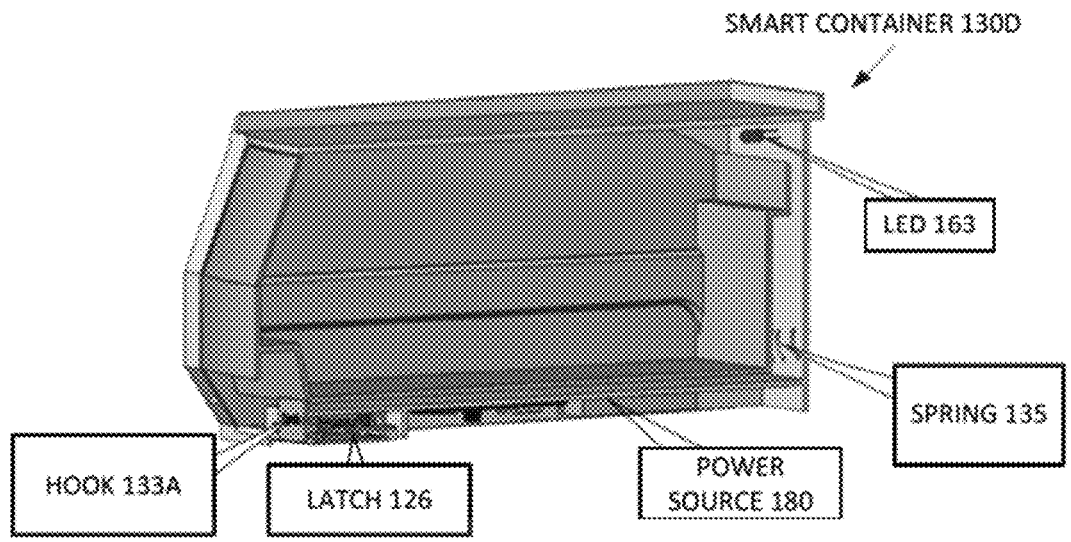
FIGS. 40A and 40B depict cut-away views of the example smart bin drawers, according to various aspects of the subject technology.
Figure 40B:
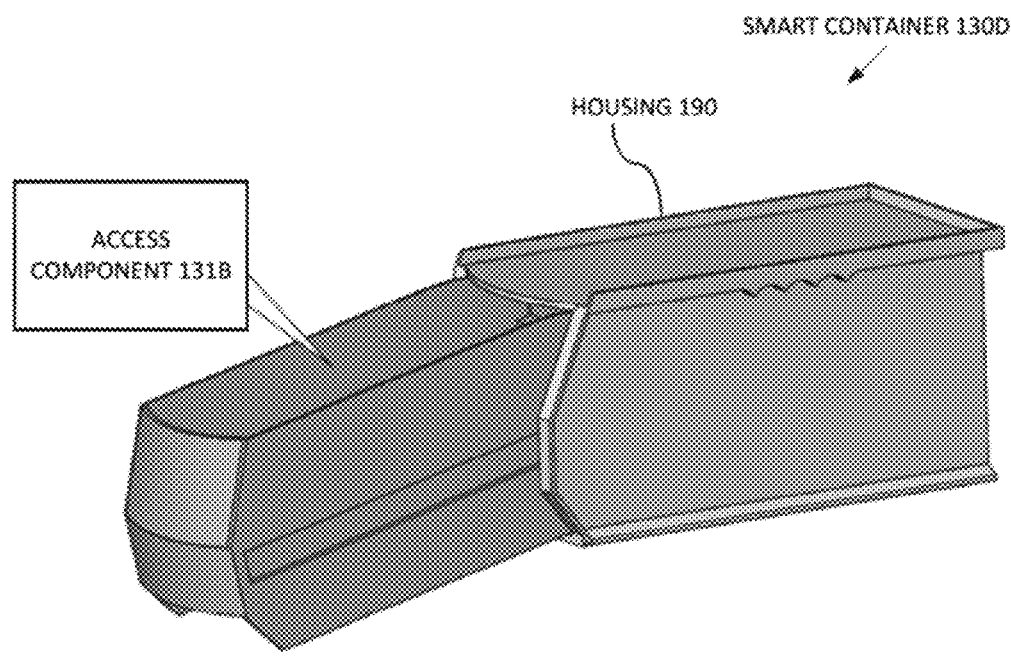

FIGS. 40A and 40B depict cut-away views of the example smart bin drawers, according to various aspects of the subject technology. According to some implementations, the outer housing may include features to mount a latch, PCBA, LEDs, and a battery. In addition, the outer housing may include features to pivot storage bin, stops to limit bin rotation. The smart bin in the drawer-configuration may include features to mount a latch hook, mounting features for the window, and spring. The electro-mechanical latch may be powered by low power. The smart bin may further contains sensors that may interface with the drawer to indicate an open or close status. The latch may have on-board memory to digitally store content/location information.

FURTHER EMBODIMENTS

With reference to FIG. 1A, the energy source 180 utilized to power the devices may be static or dynamically configured to provide energy. Six example configurations are:

Config 1 (Distributed): Disposable batteries.
Config 2 (Distributed): Rechargeable batteries/super capacitor.
Config 3 (Centralized): One high capacity battery interfaced to enclosure with docking type or wired physical connector to redistribute power to storage space.
Config 3 (Centralized): External power supply interfaced to enclosure with docking type or wired physical connector to redistribute power to storage space.
Config 4 (Centralized): Power over Ethernet (PoE) interfaced to enclosure with docking type or wired physical connector to redistribute power to storage space.
Config 5 (Centralized): Wireless power transmitter interfaced to enclosure with docking type or wired physical connector to redistribute power to storage space.
Config 6 (Distributed): Wireless power transmitters on the enclosure interfaced to wireless receiver on each smart container.

One or more aspects or features of the subject matter described herein may be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one specifically configured programmable processor, which may be special or general purpose, coupled to receive data and specific instructions from, and to transmit data and instructions to, a storage system, at least one input device, and at least one output device. The programmable system or computing system may include one or more clients and/or servers. A client and server are generally remote from each other and typically interact through a communication network. The relationship of client and server arises by virtue of computer programs running on the respective computers and having a client-server relationship to each other.

These specific computer programs, which can also be referred to as programs, software, software applications, applications, components, or code, include machine instructions for a programmable processor, and may be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A smart tote controller attachable to a tote, the smart tote controller comprising: a memory including a non-volatile data store; an actuator configured to open and close a lock to secure a lid of the tote; and a processor configured to: receive user credentials for accessing the tote; validate the user credentials for accessing the tote; trigger the actuator to open the lock, thereby allowing the lid to be opened; determine a change in contents of the tote; update, in the non-volatile data store, an inventory according to the change in contents of the tote; trigger the actuator to close the lock after detecting that the lid is closed, thereby securing the lid; and record the user credentials, one or more timestamps, and the change in contents in an access log within the non-volatile data store.

Clause 2. The smart tote controller of Clause 1, wherein the smart tote controller and the lock are disposed within a hasp lid that is attached to the lid of the tote.

Clause 3. The smart tote controller of Clause 2, wherein the smart tote controller is disposed within an upper recess of the hasp lid such that a top surface of the hasp lid is substantially flush with the smart tote controller.

Clause 4. The smart tote controller of Clause 1, further comprising one or more sensors, and wherein the processor is further configured to: record periodic sensor data from the one or more sensors in a condition log within the non-volatile data store.

Clause 5. The smart tote controller of Clause 4, wherein the one or sensors include at least one of a temperature sensor, a shock sensor, a vibration sensor, a tamper sensor, and a location sensor.

Clause 6. The smart tote controller of Clause 4, further comprising an audiovisual element, wherein the processor is further configured to output to the audiovisual element according to the condition log.

Clause 7. The smart tote controller of Clause 6, wherein the audiovisual element includes at least one of an e-ink display, a light emitting diode (LED), and a speaker.

Clause 8. The smart tote controller of Clause 1, further comprising a communications device, and wherein the processor is further configured to synchronize at least a portion of the non-volatile data store with a remote server.

Clause 9. The smart tote controller of Clause 8, wherein the synchronizing utilizes mobile mesh networking to use other smart tote controllers as nodes.

Clause 10. The smart tote controller of Clause 1, further comprising an identity authentication controller including at least one of a smartcard reader and a biometric sensor, and wherein the processor is configured to receive and validate the user credentials using the identity authentication controller.

Clause 11. The smart tote controller of Clause 1, further comprising a human interface device, wherein the processor is configured to determine the change in contents of the tote according to input data from the human interface device.

Clause 12. The smart tote controller of Clause 11, wherein the human interface device includes at least one of a button interface, a touchscreen, and a microphone.

Clause 13. The smart tote controller of Clause 1, further comprising a crypto-processor and a data bus, wherein the crypto-processor is configured to encrypt data transmitted over the data bus and stored in the non-volatile data store.

Clause 14. The smart tote controller of Clause 1, wherein the lock is selected from the group consisting of an electromechanical deadbolt and an electromechanical latch.

Clause 15. A method for secure storage, transport, and dispensing of items within a tote, the method comprising: providing a smart tote controller for attaching to the tote; receiving user credentials for accessing the tote; validating the user credentials for accessing the tote; triggering an actuator to open a lock, thereby allowing a lid of the tote to be opened; determining a change in contents of the tote; updating, in a non-volatile data store, an inventory according to the change in contents of the tote; triggering the actuator to close the lock after detecting that the lid is closed, thereby securing the lid; and recording the user credentials, one or more timestamps, and the change in contents in an access log within the non-volatile data store; and wherein the method is performed by one or more processors.

Clause 16. The method of Clause 15, wherein providing the smart tote controller comprises disposing the smart tote controller and the lock within a hasp lid that is attached to the lid of the tote, wherein the smart tote controller is disposed within an upper recess of the hasp lid such that a top surface of the hasp lid is substantially flush with the smart tote controller.

Clause 17. The method of Clause 15, further comprising: recording periodic sensor data from one or more sensors in a condition log within the non-volatile data store, wherein the one or sensors include at least one of a temperature sensor, a shock sensor, a vibration sensor, a tamper sensor, and a location sensor.

Clause 18. The method of Clause 17, further comprising: outputting to an audiovisual element according to the condition log, wherein the audiovisual element includes at least one of an e-ink display, a light emitting diode (LED), and a speaker.

Clause 19. The method of Clause 15, further comprising: synchronizing at least a portion of the non-volatile data store with a remote server, wherein the synchronizing utilizes mobile mesh networking to use other smart tote controllers as nodes.

Clause 20. A non-transitory storage medium comprising instructions that, when read by one or more processors, cause a method comprising: receiving user credentials for accessing a tote; validating the user credentials for accessing the tote; triggering an actuator to open a lock, thereby allowing a lid of the tote to be opened; determining a change in contents of the tote; updating, in a non-volatile data store, an inventory according to the change in contents of the tote; triggering the actuator to close the lock after detecting the lid is closed, thereby securing the lid; and recording the user credentials, one or more timestamps, and the change in contents in an access log.

Clause 21. An inventory device attachable to a container, the inventory device comprising: a memory including a non-volatile data store containing a local cache storing a local inventory of a container; a communication interface; an audiovisual element; and a processor configured to: output, via the audiovisual element, a visual representation of the local inventory; receive a user input; determine a change to the local inventory according to the user input; update the local inventory in the non-volatile data store according to the change; synchronize the local inventory with one or more nodes via the communication interface; and receive, from the one or more nodes via the communication interface, periodic updates for the local cache comprising locations and inventories of one or more remote bins.

Clause 22. The inventory device of Clause 21, wherein receiving the user input is from a user interface comprising a plurality of buttons including a take button to decrement a quantity of an item in the local inventory, and a receive button to increment the quantity of the item in the local inventory.

Clause 23. The inventory device of Clause 21, wherein receiving the user input is from detecting a radio frequency identification (RFID) tag added to or removed from the container.

Clause 24. The inventory device of Clause 21, wherein the visual representation includes a description and a quantity of items in the container.

Clause 25. The inventory device of Clause 21, further comprising a housing including: a front surface populated with the audiovisual element and the user interface; and a front facing access cover securing a battery compartment formed within the housing.

Clause 26. The inventory device of Clause 25, wherein the housing includes a rear surface populated with a clip recess configured to slide into a retainer slot of the bin or tote for attaching the inventory device to the bin.

Clause 27. The inventory device of Clause 21, further comprising one or more sensors, and wherein the processor is further configured to: record periodic sensor data from the one or more sensors in a condition log within the non-volatile data store.

Clause 28. The inventory device of Clause 27, wherein the one or sensors include at least one of a temperature sensor, a shock sensor, a vibration sensor, a tamper sensor, and a location sensor.

Clause 29. The inventory device of Clause 28, wherein the tamper sensor includes at least one of a mechanical switch, an anti-tamper film, a photodiode, and a proximity sensor to determine whether a housing of the inventory device has been tampered.

Clause 30. The inventory device of Clause 21, wherein audiovisual element includes at least one of an e-ink display, a light emitting diode (LED), and a speaker.

Clause 31. The inventory device of Clause 21, wherein the processor is further configured to: broadcast, via the communication interface, a unique identifier associated with the inventory device.

Clause 32. The inventory device of Clause 21, wherein the communications device is configured to utilize mobile mesh networking to use other inventory devices as nodes.

Clause 33. The inventory device of Clause 21, wherein the processor is further configured to: receive, from the remote server via the communication interface, a request to identify the bin or tote based on a unique identifier associated with the inventory device; and output an alert to the audiovisual element, wherein the alert changes according to a detected proximity to a remote device.

Clause 34. The inventory device of Clause 21, wherein the processor is configured to operate in a refrigerator.

Clause 35. The inventory device of Clause 21, wherein the processor is further configured to: adjust a power state of the processor based on training a machine learning algorithm on usage data collected from a plurality of inventory devices.

Clause 36. The inventory device of Clause 21, further comprising an attachment surface for dynamically affixing to a container;

Clause 37. The inventory device of Clause 36, wherein the attachment surface includes an attachment sensor configured to detect attachment between the attachment surface and the container.

Clause 38. The inventory device of claim 37, wherein the processor is further configured to: receive a message from the attachment sensor indicating detachment from the container; and transmit an alert message indicating the detachment.

Clause 39. The inventory device of claim 38, further comprising an output device, and wherein transmitting the alert message comprises causing emission of a perceivable output from the output device.

Clause 40. The inventory device of claim 38, wherein transmitting the alert message comprises transmitting the alert message via the communication interface to a remote device.

Clause 41. A method for automatic inventory management of items in a bin, the method comprising: providing an inventory device for attaching to the bin; outputting, via an audiovisual element, a visual representation of a local inventory of the bin; receiving, via a user interface, a user input; determining a change to the local inventory according to the user input; updating the local inventory in a non-volatile data store according to the change; synchronizing the local inventory with one or more nodes via a communication interface; and receiving, from one or more nodes via the communication interface, periodic updates for a local cache comprising locations and inventories of one or more remote bins.

Clause 42. The method of claim 41, wherein receiving the user input comprises receiving, via the user interface comprising a plurality of buttons, the user input, wherein the plurality of buttons include a take button to decrement a quantity of an item in the local inventory, and a receive button to increment the quantity of the item in the local inventory.

Clause 43. The method of claim 41, wherein outputting the visual representation comprises outputting a description and a quantity of items in the bin.

Clause 44. The method of claim 41, further comprising: receiving, from the remote server via the communication interface, a request to identify the bin or tote based on a unique identifier associated with the inventory device; and outputting an alert to the audiovisual element.

Clause 45. A non-transitory storage medium comprising instructions that, when read by one or more processors, cause a method comprising: outputting, via an audiovisual element, a visual representation of a local inventory of a bin; receiving, via a user interface, a user input; determining a change to the local inventory according to the user input; updating the local inventory in a non-volatile data store according to the change; synchronizing the local inventory with one or more nodes via a communication interface; and receiving, from one or more nodes via the communication interface, periodic updates for a local cache comprising locations and inventories of one or more remote bins.

Clause 46: The method of Clause 41 or 45, wherein the bin is housed within a bin housing, and wherein the bin housing includes a near field communication (NFC) antennae, and the bin includes an NFC tag affixed to a side of the bin and configured to come into communicable contact with the NFC antennae when the bin is loaded into the bin housing, wherein the method further comprises: detecting, by a control module responsive to the bin being placed in or removed from the bin housing, a presence of the NFC tag via a signal received from the NFC antennae; and recording, by the control module responsive to the detecting, an open or closed status of the bin responsive to a respective opening or closing of the bin.

Clause 47. The method of Clause 45 or 46, wherein the bin housing contains a plurality of bins, and wherein the method further comprises: detecting that the bin was removed from a first bin location within the housing and inserted into a second bin location within the housing; determining that the second location is not a proper location for the bin; and providing an alert regarding the placement of the bin at the second location.

Clause 48. The method of Clause 47, wherein the method further comprises receiving a signal from a mobile device to provide a medication; querying the controller module associated with the bin housing for a bin location of a bin storing the medication; receiving a location of the bin storing the medication; and determining whether a user associated with the request is authorized to open the bin storing the medication; and sending, when the user is authorized to open the bin, a signal to the bin location to open the bin, and wherein the bin storing the medication is automatically opened responsive to the signal.

Clause 49. An inventory storage system, comprising: a bin housing; an audiovisual element associated with the bin housing; one or more containers configured to be placed within and to slidably be removed from within the bin housing; a communication interface associated with the bin housing and the one or more containers within the bin housing; a memory storing a local inventory of at least a first container of the one or more containers; and a processor configured to: output, via the audiovisual element, a visual representation of the local inventory; receive a user input; determine a change to the local inventory according to the user input; update the local inventory in the non-volatile data store according to the change; synchronize the local inventory with one or more nodes via the communication interface; and receive, from the one or more nodes via the communication interface, periodic updates for the local cache comprising locations and inventories of one or more remote bins.

Clause 50. The inventory storage system of Clause 49, further comprising: an actuator configured to open and close a lock to secure a lid of the first container; wherein the processor is further configured to: receive user credentials for accessing the first container; validate the user credentials for accessing the first container; trigger the actuator to open the lock, thereby allowing the lid to be opened; determine a change in contents of the first container; update, in the non-volatile data store, an inventory according to the change in contents of the first container; trigger the actuator to close the lock after detecting that the lid is closed, thereby securing the lid; and record the user credentials, one or more timestamps, and the change in contents in an access log within the non-volatile data store.

Clause 51. The inventory storage system of Clause 49 or 50, further comprising: a near field communication (NFC) antennae within the bin housing; an NFC tag affixed to a side of the first container and configured to come into communicable contact with the NFC antennae when the first container is loaded into the bin housing, wherein the processor is further configured to: detect, responsive to the bin being placed in or removed from the bin housing, a presence of the NFC tag via a signal received from the NFC antennae; and record, responsive to the detecting, an open or closed status of the first container responsive to a respective opening or closing of the first container.

Clause 52. The inventory storage system of Clause 51, wherein the one or more bins includes a plurality of bins, and wherein the processor is further configured to: detect that the bin was removed from a first bin location within the housing and inserted into a second bin location within the housing; determine that the second location is not a proper location for the bin; and provide an alert regarding the placement of the bin at the second location.

Clause 53. The inventory storage system of Clause 52, wherein the processor is further configured to: receive a request from a mobile device to provide a medication; determine a bin location within the bin housing of a container storing the medication; and determine whether a user associated with the request is authorized to access the container storing the medication; and send, when the user is authorized to open the first container, a signal to the bin location to enable access to the container storing the medication from the first housing.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

Features described may include machine learning. Machine learning may include models, equations, artificial neural networks, recurrent neural networks, convolutional neural networks, decision trees, or other machine readable artificial intelligence structure. Examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An inventory storage system, comprising:
    a mobile inventory device comprising a housing enclosure, a processor, non-transitory memory, and communication interface device enclosed within the housing enclosure, wherein the housing enclosure is configured to detachably couple to a storage bin,
    wherein the processor is configured to:
        associate the mobile inventory device with a first storage bin;
        store a local inventory of the first storage bin in the memory;
        receiving, via a user interface associated with the mobile inventory device, a first user input associated with an item type;
        electronically activate the communication interface device;
        wirelessly synchronize, via the activated communication interface device, the local inventory with one or more other inventory devices associated with one or more other respective bins geographically remote from the first storage bin;
        update, based on inventory information wirelessly received during the synchronizing from the one or more other inventory devices, the local inventory to include an identification and at least one inventory of the one or more other respective bins geographically remote from the first storage bin; and
        identify, via a display device associated with the mobile inventory device, based on the updated local inventory, a second storage bin storing the item type.

2. The inventory storage system of claim 1, wherein the processor is further configured to:
    receive, from the one or more other inventory devices via the communication interface device, periodic updates for the local inventory comprising a location of at least one of the other respective bins geographically remote from the first storage bin.

3. The inventory storage system of claim 1, wherein the processor is further configured to:

receive user credentials for accessing the first storage bin;

validate the user credentials for accessing the first storage bin; and cause an actuator of the first storage bin to open a lock associated with the first storage bin, thereby allowing a lid of the first storage bin to be opened.

4. The inventory storage system of claim 3, wherein the processor is further configured to:

determine a change in contents of the first storage bin;

update, in a non-volatile data store, an inventory according to the change in contents of the first storage bin;

trigger the actuator to close the lock after detecting that the lid is closed, thereby securing the lid; and record the user credentials in connection with the change in contents in an access log within the non-volatile data store.

5. The inventory storage system of claim 4, wherein determining the change in contents comprises receiving, at the user interface, a user input indicating the change in contents.

6. The inventory storage system of claim 1, further comprising:

a bin housing containing the first storage bin and comprising a first field communication (NFC) device, wherein the first storage bin comprises a second NFC device configured to come into communicable contact with the first NFC device when the first storage bin is loaded into the bin housing, wherein the processor is further configured to:

detect, responsive to the bin being placed in or removed from the bin housing, a presence of the bin based on the first and second NFC devices being in communicable contact; and record an indication of the detecting and an open or closed status of the bin based on a respective opening or closing of the bin.

7. The inventory storage system of claim 6, further comprising:

a plurality of bins within the bin housing, wherein the processor is further configured to:

detect that the bin was removed from a first bin location within the bin housing and inserted into a second bin location within the bin housing;

determine that the second bin location is not a proper location for the bin; and provide an alert regarding placement of the bin at the second bin location.

8. The inventory storage system of claim 7, wherein the processor is further configured to:

receive, by the mobile inventory device from a mobile device, a request for a medication;

determine, within the bin housing, a location of a bin storing the medication;

determine whether a user associated with the request is authorized to open the bin storing the medication;

send, when the user is authorized to open the bin storing the medication, a signal to an inventory device associated with and coupled to a bin at the location to open the bin;

wherein the bin storing the medication is opened responsive to the signal.

9. The inventory storage system of claim 1, wherein wirelessly synchronizing the local inventory comprises receiving a location of the second storage bin storing the item type, and wherein identifying the second storage bin storing the item type comprises displaying a location of the second storage bin storing the item type on the display device.

10. The inventory storage system of claim 1, wherein the processor is further configured to:

receive, from a remote server via the communication interface device, a request to identify the first storage bin based on a unique identifier associated with the mobile inventory device; and output an alert to the user interface responsive to the request.

11. A method for electronically storing inventory in a storage bin, the method comprising:

associating a mobile inventory device with a first storage bin, the mobile inventory device configured to couple to the first storage bin;

storing a local inventory of the first storage bin in a non-volatile data store of a mobile inventory device;

receiving, via a user interface associated with the mobile inventory device, a first user input associated with an item type;

electronically activating a communication interface device;

wirelessly synchronizing, via the activated communication interface device, the local inventory with one or more other inventory devices associated with one or more other respective bins geographically remote from the first storage bin;

updating, based on inventory information wirelessly received during the synchronizing from the one or more other inventory devices, the local inventory to include an identification and at least one inventory of the one or more other respective bins geographically remote from the first storage bin; and identifying, via a display device associated with the mobile inventory device, based on the updated local inventory, a second storage bin storing the item type.

12. The method of claim 11, further comprising, by the mobile inventory device: receiving user credentials for accessing the first storage bin; validating the user credentials for accessing the first storage bin; causing an actuator of the first storage bin to open a lock associated with the first storage bin, thereby allowing a lid of the first storage bin to be opened.

13. The method of claim 12, further comprising, by the mobile inventory device:

determining a change in contents of the first storage bin;

updating, in a non-volatile data store, an inventory according to the change in contents of the first storage bin;

triggering the actuator to close the lock after detecting that the lid is closed, thereby securing the lid; and recording the user credentials in connection with the change in contents in an access log within the non-volatile data store.

14. The method of claim 13, wherein determining the change in contents comprises receiving, at the user interface, a user input indicating the change in contents.

15. The method of claim 11, wherein the first storage bin is housed within a bin housing, and wherein the bin housing includes a first field communication (NFC) device, and the first storage bin comprises a second NFC device configured to come into communicable contact with the first NFC device when the first storage bin is loaded into the bin housing, wherein the method further comprises:
detecting, responsive to the bin being placed in or removed from the bin housing, a presence of the bin based on the first and second NFC devices being in communicable contact; and
recording an indication of the detecting and an open or closed status of the bin based on a respective opening or closing of the bin.

16. The method of claim 15, wherein the bin housing contains a plurality of bins, and wherein the method further comprises:
detecting that the bin was removed from a first bin location within the bin housing and inserted into a second bin location within the bin housing;
determining that the second bin location is not a proper location for the bin; and
providing an alert regarding placement of the bin at the second bin location.

17. The method of claim 16, wherein the method further comprises:
receiving, by the mobile inventory device from a mobile device, a request for a medication;
determining, within the bin housing, a location of a bin storing the medication;
determining whether a user associated with the request is authorized to open the bin storing the medication;
sending, when the user is authorized to open the bin storing the medication, a signal to an inventory device associated with and coupled to a bin at the location to open the bin;
wherein the bin storing the medication is opened responsive to the signal.

18. The method of claim 11,
wherein wirelessly synchronizing the local inventory comprises receiving a location of the second storage bin storing the item type, and
wherein identifying the second storage bin storing the item type comprises displaying a location of the second storage bin storing the item type on the display device.

19. The method of claim 11, further comprising:
receiving, from a remote server via the communication interface device, a request to identify the first storage bin based on a unique identifier associated with the mobile inventory device; and
outputting an alert to the user interface responsive to the request.

20. A non-transitory machine-readable memory storing instructions thereon that, when executed by one or more processors, causes the one or more processors to perform operations, comprising:
associating a mobile inventory device with a first storage bin, the mobile inventory device configured to couple to the first storage bin;
storing a local inventory of the first storage bin in a non-volatile data store of a mobile inventory device;
receiving, via a user interface associated with the mobile inventory device, a first user input associated with an item type;
electronically activating a communication interface device;
wirelessly synchronizing, via the activated communication interface device, the local inventory with one or more other inventory devices associated with one or more other respective bins geographically remote from the first storage bin;
updating, based on inventory information wirelessly received during the synchronizing from the one or more other inventory devices, the local inventory to include an identification and at least one inventory of the one or more other respective bins geographically remote from the first storage bin; and
identifying, via a display device associated with the mobile inventory device, based on the updated local inventory, a second storage bin storing the item type.

* * * * *